US007816082B2

(12) United States Patent
Han et al.

(10) Patent No.: US 7,816,082 B2
(45) Date of Patent: Oct. 19, 2010

(54) METHODS OF IDENTIFYING PANCREATIC CANCER CELLS

(75) Inventors: Haiyong Han, Chandler, AZ (US);
Robert J Gillies, Tucson, AZ (US);
David L Morse, Tucson, AZ (US);
Victor J Hruby, Tucson, AZ (US)

(73) Assignees: The Arizona Board of Regents on behalf of the University of Arizona, Tucson, AZ (US); The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 12/041,350

(22) Filed: Mar. 3, 2008

(65) Prior Publication Data

US 2008/0261818 A1 Oct. 23, 2008

Related U.S. Application Data

(60) Provisional application No. 60/905,120, filed on Mar. 6, 2007.

(51) Int. Cl.
*C12Q 1/68* (2006.01)
*G01N 33/574* (2006.01)

(52) U.S. Cl. .......................... 435/6; 435/7.21; 435/7.23

(58) Field of Classification Search ........................ None
See application file for complete search history.

(56) References Cited

U.S. PATENT DOCUMENTS

2003/0105000 A1* 6/2003 Pero et al. ...................... 514/12
2004/0180002 A1* 9/2004 Young et al. ................ 424/1.49

OTHER PUBLICATIONS

Greenbaum et al. (Genome Biology, 2003, vol. 4, Issue 9, pp. 117.1-117.8).*
Brennan et al. (J. Autoimmunity, 1989, 2 (suppl.): 177-186).*
Zimmer (Cell Motility and the Cytoskeleton, 1991. 20:325-337).*
Hell et al. (Laboratory Investigation, 1995, 73: 492-496).*
Fu et al. (EMBO J., 1996, 15:43982-4401).*
Vallejo et al. (Biochimie, 2000 82:1129-1133).*
Rudikoff et al. (Proc. Natl. Acad. Sci., USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Burgess et al. (J of Cell Bio. 111:2129-2138, 1990).*
Gura (Science, 1997, 278:1041-1042).*
Kaiser (Science, 2006, 313: 1370).*
Benedict et al. (J. Exp. Medicine, 2001, 193(1) 89-99).*
Jiang et al. (J. Biol. Chem., 2003, 278(7) 4763-4769).*
Matsushita et al. (FEBS Letters, 1999, vol. 443, pp. 348-352).*
Singh et al. (Glycobiology, 2001, vol. 11, pp. 587-592).*
Bowie et al. (Science, 1990, 257:1306-1310).*
Lazar et al (Molecular and Cellular Biology, 1988, 8:1247-1252).*
Jemal A et al, Cancer Statistics, CA Cancer J Clin 56 106-130 (Mar./Apr. 2006).

Hale G, Therapeutic antibodies—Delivering the promise?, Adv Drug Deliv Rev, 58 633-639 (May 2006).
Pegram MD et al, Targeted therapy: wave of the future. J Clin Oncol 23 1776-1781 (2005).
Reichert JM et al, Monoclonal antibody successes in the clinic. Nat Biotechnol 23 1073-1078 (2005).
Richter M and Zhang H, Receptor-targeted cancer therapy. DNA Cell Biol 24 271-282 (2005).
Sawyers C, Targeted cancer therapy, Nature, 432 294-297 (2004).
Vasir JK and V Labhasetwar, Targeted drug delivery in cancer therapy,Technol Cancer Res Treat, 4 363-374 (2005).
Moore MJ, Brief communication: a new combination in the treatment of advanced pancreatic cancer, Semin Oncol 32 5-6 (2005).
Handl HL et al, Hitting multiple targets with multimeric ligands, Expert Opin Ther Targets, 8 565-586 (2004).
Vagner J et al, Novel targeting strategy based on multimeric ligands for drug delivery and molecular imaging: homooligomers of alpha-MSH, Bioorg Med Chem Let 14 211-215 (2004).
Son CG et al, Database of mRNA gene expression profiles of multiple human organs, Genome Res 15 443-450 (2005).
Shyamsundar R et al, A DNA microarray survey of gene expression in normal human tissues, Genome Biol 6 R22.1-R22.7 (2005).
Nocito A et al, Tissue microarrays (TMAs) for high-throughput molecular pathology research, Int J Cancer, 94 1-5 (2001).
Torhorst J et al, Tissue microarrays for rapid linking of molecular changes to clinical endpoints, Am J Pathol 159 2249-2256 (2001).
Kononen J et al, Tissue microarrays for high throughput molecular profiling of tumor specimens, Nat Med 4 844-847 (1998).
Haubner R et al, Noninvasive visualization of the activated alphavbeta3 integrin in cancer patients by positron emission tomography and [18F]Galacto-RGD, PLoS Med, 2, 0244-0252 (2005).
Beer AJ et al, PET-based human dosimetry of 18F-galacto-RGD, a new radiotracer for imaging alpha v beta3 expression, J Nucl Med 47, 763-769 (May 2006).
Goldenberg DM and Sharkey RM. Novel radiolabeled antibody conjugates, Oncogene 26 3734-3744 (May 2007).
Jhanwar YS and Divgi C, Current status of therapy of solid tumors, J Nucl Med 46 141S-150S (2005).
Boturyn et al, Template assembled cyclopeptides as multimeric system for integrin targeting and endocytosis, J Am Chem Soc, 126 5730-5739 (2004).
Laugel B et al, Design of soluble recombinant T cell receptors for antigen targeting and T cell inhibition, J Biol Chem 280 1882-1892 (2005).
Garanger E et al, Multivalent RGD synthetic peptides as potent alphaVbeta3 integrin ligands, Org Biomol Chem, 4 1958-1965 (Apr. 2006).

(Continued)

*Primary Examiner*—Peter J Reddig
(74) *Attorney, Agent, or Firm*—Jeffrey M. Jackson

(57) ABSTRACT

Methods that identify cells as pancreatic cancer cells based on assessing the expression of combinations of target molecules expressed preferentially on pancreatic cancer cells are disclosed. Combinations were initially discovered by microarray analysis and selected based upon tumor specificity, relative lack of cross-reactivity with normal tissues, and applicability as targets of multispecific ligands. The claimed methods encompass measuring the expression of three or more specific target molecules in combination and correlating positive expression of the combination with an identification of the cell as a pancreatic cancer cell.

5 Claims, 4 Drawing Sheets

OTHER PUBLICATIONS

Mammen M et al, Polyvalent Interactions in Biological Systems: Implications for Design and Use of Multivalent Ligands and Inhibitors, Angewandte Chemie 37 2754-2796 (1998).

Boyd RS et al, Proteomic analysis of the cell-surface membrane in chronic lymphocytic leukemia: identification of two novel proteins, BCNP1 and MIG2B, Leukemia 17 1605-1612 (2003).

Zhao Y et al, Proteomic analysis of integral plasma membrane proteins. Anal Chem, 76 1817-1823 (2004).

Loyet KM et al, Proteomic profiling of surface proteins on Th1 and Th2 cells. J Proteome Res, 4 400-409 (2005).

Dougherty ER et al, Inference from clustering with application to gene-expression microarrays, J Comput Biol, 9 105-126 (2002).

Andersen Cl et al, Improved procedure for fluorescence in situ hybridization on tissue microarrays, Cytometry 45 83-86 (2001).

Mousses S et al. Clinical validation of candidate genes associated with prostate cancer progression in the CWR22 model system using tissue microarrays, Cancer Res 62 1256-1260 (2002).

Morse DL et al, Determining suitable internal standards for mRNA quantification of increasing cancer progression in human breast cells by real-time reverse transcriptase polymerase chain reaction, Anal Biochem 342 69-77 (2005).

Lynch RM et al, Modulation of hexokinase association with mitochondria analyzed with quantitative three-dimensional confocal microscopy, J Cell Biol 112 385-395 (1991).

Rose A, The sensitivity performance of the human eye on an absolute scale, J Opt Soc Am 38 196-208 (1948).

\* cited by examiner

SEQUENCE LISTING

<160> NUMBER OF SEQ ID NOS: 58

<210> SEQ ID NO 1
<211> LENGTH: 3284
<212> TYPE: DNA
<213> ORGANISM: Homo sapiens

<400> SEQUENCE: 1

| | | | | | |
|---|---|---|---|---|---|
| gaagacacgg | acagatgaac | ttaaaagaga | agctttagct | gccaaagatt | gggaaaggga | 60 |
| aaggacaaaa | aagaccoctg | ggctacacgg | cgtaggtgca | gggtttccta | ctgctgttct | 120 |
| tttatgctgg | gagctgtggc | tgtaaccaac | taggaaataa | cgtatgcagc | agctatggct | 180 |
| gtcagagagt | tgtgcttccc | aagacaaagg | caagtcctgt | ttcttttct | tttttgggga | 240 |
| gtgtccttgg | caggttctgg | gtttggacgt | tattcggtga | ctgaggaaac | agagaaagga | 300 |
| tcctttgtgg | tcaatctggc | aaaggatctg | ggactagcag | aggggagct | ggctgcaagg | 360 |
| ggaaccaggg | tggtttccga | tgataacaaa | caatacctgc | tcctggattc | acataccggg | 420 |
| aatttgctca | caaatgagaa | actggaccga | gagaagctgt | gtggccctaa | agagccctgt | 480 |
| atgctgtatt | tccaaatttt | aatggatgat | cccttcaga | tttaccgggc | tgagctgaga | 540 |
| gtcagggata | taaatgatca | cgcgccagta | tttcaggaca | aagaaacagt | cttaaaaata | 600 |
| tcagaaaata | cagctgaagg | gacagcattt | agactagaaa | gagcacagga | tccagatgga | 660 |
| ggacttaacg | gtatccaaaa | ctacacgatc | agccccaact | cttttttcca | tattaacatt | 720 |
| agtggcggtg | atgaaggcat | gatatatcca | gagctagtgt | tggacaaagc | actggatcgg | 780 |
| gaggagcagg | gagagctcag | cttaaccctc | acagcgctgg | atggtgggtc | tccatccagg | 840 |
| tctgggacct | ctactgtacg | catcgttgtc | ttggacgtca | atgacaatgc | cccacagttt | 900 |
| gcccaggctc | tgtatgagac | ccaggctcca | gaaaacagcc | ccattgggtt | ccttattgtt | 960 |
| aaggtatggg | cagaagatgt | agactctgga | gtcaacgcgg | aagtatccta | ttcatttttt | 1020 |
| gatgcctcag | aaaatattcg | aacaaccttt | caaatcaatc | cttttctgg | ggaaatcttt | 1080 |
| ctcagagaat | tgcttgatta | tgagttagta | aattcttaca | aaataaatat | acaggcaatg | 1140 |
| gacggtggag | gcctttctgc | aagatgtagg | gttttagtgg | aagtattgga | caccaatgac | 1200 |
| aatcccctg | aactgatcgt | atcatcattt | tccaactctg | ttgctgagaa | ttctcctgag | 1260 |
| acgccgctgg | ctgtttttaa | gattaatgac | agagactctg | gagaaaatgg | aaagatggtt | 1320 |
| tgctacattc | aagagaatct | gccattccta | ctaaaaccctt | ctgtggagaa | ttttttacatc | 1380 |
| ctaattacag | aaggcgcgct | ggacagagag | atcagagccg | agtacaacat | cactatcacc | 1440 |
| gtcactgact | tggggacacc | caggctgaaa | accgagcaca | cataacggtt | cctggtctcc | 1500 |
| gacgtcaatg | acaacgcccc | cgccttcacc | caaacctcct | acaccctgtt | cgtccgcgag | 1560 |
| aacaacagcc | ccgccctgca | catcggcagc | gtcagcgcca | cagacagaga | ctcgggcacc | 1620 |
| aacgcccagg | tcacctactc | gctgctgccg | ccccaagacc | cgcacctgcc | cctcgcctcc | 1680 |
| ctggtctcca | tcaacgcgga | caacggccac | ctgttcgccc | tcaggtcgct | ggactacgag | 1740 |
| gccctgcagg | ctttcgagtt | ccgcgtgggc | gccacagacc | gcggctcccc | cgcgctgagc | 1800 |
| agagaggcgc | tggtgcgcgt | gctggtgctg | acgccaacg | acaactcgcc | cttcgtgctg | 1860 |
| tacccgctgc | agaacggctc | cgcgccctgc | accgagctgg | tgccccgggc | ggccgagccg | 1920 |
| ggctacctgg | tgaccaaggt | ggtggcggtg | acggcgact | cgggccagaa | cgcctggctg | 1980 |
| tcgtaccagc | tgctcaaggc | cacggagccc | gggctgttcg | gtgtgtgggc | gcacaatggg | 2040 |

```
gaggtgcgca ccgccaggct gctgagcgag cgcgacgcag ccaagcacag gctcgtggtg   2100
cttgtcaagg acaatggcga gcctcctcgc tcggccaccg ccacgctgca cttgctcctg   2160
gtggacggct ctcccagcc ctacctgcct ctcccggagg cggccccggc ccaggcccag    2220
gccgaggccg acttgctcac cgtctacctg gtggtggcgt tggcctcggt gtcttcgctc   2280
ttcctcctct cggtgctcct gttcgtggcg gtgcggctgt gcaggaggag cagggcggcc   2340
tcggtgggtc gctgctcggt gcccgagggt cctttccag ggcatctggt ggacgtgagg    2400
ggcgctgaga ccctgtccca gagctaccag tatgaggtgt gtctgacggg aggccccggg   2460
accagtgagt tcaagttctt gaaaccagtt atttcggata ttcaggcaca gggccctggg   2520
aggaagggtg aagaaaattc caccttccga aatagctttg gatttaatat tcagtaaagt   2580
ctgtttttag tttcatatac ttttggtgtg ttacatagcc atgtttctat tagtttactt   2640
ttaaatctca aatttaagtt attatgcaac ttcaagcatt attttcaagt agtatacccc   2700
tgtggtttta caatgtttca tcatttttt gcattaataa caactgggtt taatttaatg    2760
agtatttttt tctaaatgat agtgttaagg ttttaattct ttccaactgc ccaaggaatt   2820
aattactatt atatctcatt acagaaatct gaggttttga ttcatttcag agcttgcatc   2880
tcatgattct aatcacttct gtctatagtg tacttgctct atttaagaag gcatatctac   2940
atttccaaac tcattctaac attctatata ttcgtgtttg aaaaccatgt catttatttc   3000
tacatcatgt atttaaaaag aaatatttct ctactactat gctcatgaca aaatgaaaca   3060
aagcatattg tgagcaatac tgaacatcaa taataccctt agtttatata cttattattt   3120
tatctttaag catgctactt ttacttggcc aatattttct tatgttaact tttgctgatg   3180
tataaaacag actatgcctt ataattgaaa taaaattata atctgcctga aaatgaataa   3240
aaataaaaca ttttgaaatg tgaaaaaaaa aaaaaaaaa aaaa                     3284

<210> SEQ ID NO 2
<211> LENGTH: 800
<212> TYPE: PRT
<213> ORGANISM: Homo sapiens

<400> SEQUENCE: 2

Met Ala Val Arg Glu Leu Cys Phe Pro Arg Gln Arg Gln Val Leu Phe
1               5                   10                  15

Leu Phe Leu Phe Trp Gly Val Ser Leu Ala Gly Ser Gly Phe Gly Arg
            20                  25                  30

Tyr Ser Val Thr Glu Glu Thr Glu Lys Gly Ser Phe Val Val Asn Leu
        35                  40                  45

Ala Lys Asp Leu Gly Leu Ala Glu Gly Glu Leu Ala Ala Arg Gly Thr
    50                  55                  60

Arg Val Val Ser Asp Asp Asn Lys Gln Tyr Leu Leu Leu Asp Ser His
65                  70                  75                  80

Thr Gly Asn Leu Leu Thr Asn Glu Lys Leu Asp Arg Glu Lys Leu Cys
                85                  90                  95

Gly Pro Lys Glu Pro Cys Met Leu Tyr Phe Gln Ile Leu Met Asp Asp
            100                 105                 110

Pro Phe Gln Ile Tyr Arg Ala Glu Leu Arg Val Arg Asp Ile Asn Asp
        115                 120                 125

His Ala Pro Val Phe Gln Asp Lys Glu Thr Val Leu Lys Ile Ser Glu
    130                 135                 140

Asn Thr Ala Glu Gly Thr Ala Phe Arg Leu Glu Arg Ala Gln Asp Pro
```

-continued

```
            145                 150                 155                 160
        Asp Gly Gly Leu Asn Gly Ile Gln Asn Tyr Thr Ile Ser Pro Asn Ser
                        165                 170                 175
        Phe Phe His Ile Asn Ile Ser Gly Gly Asp Glu Gly Met Ile Tyr Pro
                        180                 185                 190
        Glu Leu Val Leu Asp Lys Ala Leu Asp Arg Glu Glu Gln Gly Glu Leu
                        195                 200                 205
        Ser Leu Thr Leu Thr Ala Leu Asp Gly Gly Ser Pro Arg Ser Gly
                        210                 215                 220
        Thr Ser Thr Val Arg Ile Val Leu Asp Val Asn Asp Asn Ala Pro
        225                 230                 235                 240
        Gln Phe Ala Gln Ala Leu Tyr Glu Thr Gln Ala Pro Glu Asn Ser Pro
                        245                 250                 255
        Ile Gly Phe Leu Ile Val Lys Val Trp Ala Glu Asp Val Asp Ser Gly
                        260                 265                 270
        Val Asn Ala Glu Val Ser Tyr Ser Phe Phe Asp Ala Ser Glu Asn Ile
                        275                 280                 285
        Arg Thr Thr Phe Gln Ile Asn Pro Phe Ser Gly Glu Ile Phe Leu Arg
                        290                 295                 300
        Glu Leu Leu Asp Tyr Glu Leu Val Asn Ser Tyr Lys Ile Asn Ile Gln
        305                 310                 315                 320
        Ala Met Asp Gly Gly Leu Ser Ala Arg Cys Arg Val Leu Val Glu
                        325                 330                 335
        Val Leu Asp Thr Asn Asp Asn Pro Pro Glu Leu Ile Val Ser Ser Phe
                        340                 345                 350
        Ser Asn Ser Val Ala Glu Asn Ser Pro Glu Thr Pro Leu Ala Val Phe
                        355                 360                 365
        Lys Ile Asn Asp Arg Asp Ser Gly Glu Asn Gly Lys Met Val Cys Tyr
                        370                 375                 380
        Ile Gln Glu Asn Leu Pro Phe Leu Leu Lys Pro Ser Val Glu Asn Phe
        385                 390                 395                 400
        Tyr Ile Leu Ile Thr Glu Gly Ala Leu Asp Arg Glu Ile Arg Ala Glu
                        405                 410                 415
        Tyr Asn Ile Thr Ile Thr Val Thr Asp Leu Gly Thr Pro Arg Leu Lys
                        420                 425                 430
        Thr Glu His Asn Ile Thr Val Leu Val Ser Asp Val Asn Asp Asn Ala
                        435                 440                 445
        Pro Ala Phe Thr Gln Thr Ser Tyr Thr Leu Phe Val Arg Glu Asn Asn
                        450                 455                 460
        Ser Pro Ala Leu His Ile Gly Ser Val Ser Ala Thr Asp Arg Asp Ser
        465                 470                 475                 480
        Gly Thr Asn Ala Gln Val Thr Tyr Ser Leu Leu Pro Pro Gln Asp Pro
                        485                 490                 495
        His Leu Pro Leu Ala Ser Leu Val Ser Ile Asn Ala Asp Asn Gly His
                        500                 505                 510
        Leu Phe Ala Leu Arg Ser Leu Asp Tyr Glu Ala Leu Gln Ala Phe Glu
                        515                 520                 525
        Phe Arg Val Gly Ala Thr Asp Arg Gly Ser Pro Ala Leu Ser Arg Glu
                        530                 535                 540
        Ala Leu Val Arg Val Leu Val Leu Asp Ala Asn Asp Asn Ser Pro Phe
        545                 550                 555                 560
        Val Leu Tyr Pro Leu Gln Asn Gly Ser Ala Pro Cys Thr Glu Leu Val
                        565                 570                 575
```

-continued

```
Pro Arg Ala Ala Glu Pro Gly Tyr Leu Val Thr Lys Val Val Ala Val
            580                 585                 590
Asp Gly Asp Ser Gly Gln Asn Ala Trp Leu Ser Tyr Gln Leu Leu Lys
        595                 600                 605
Ala Thr Glu Pro Gly Leu Phe Gly Val Trp Ala His Asn Gly Glu Val
        610                 615                 620
Arg Thr Ala Arg Leu Leu Ser Glu Arg Asp Ala Ala Lys His Arg Leu
625                 630                 635                 640
Val Val Leu Val Lys Asp Asn Gly Glu Pro Pro Arg Ser Ala Thr Ala
                645                 650                 655
Thr Leu His Leu Leu Val Asp Gly Phe Ser Gln Pro Tyr Leu Pro
                660                 665                 670
Leu Pro Glu Ala Ala Pro Ala Gln Ala Gln Ala Glu Ala Asp Leu Leu
        675                 680                 685
Thr Val Tyr Leu Val Val Ala Leu Ala Ser Val Ser Ser Leu Phe Leu
        690                 695                 700
Leu Ser Val Leu Phe Val Ala Val Arg Leu Cys Arg Arg Ser Arg
705                 710                 715                 720
Ala Ala Ser Val Gly Arg Cys Ser Val Pro Glu Gly Pro Phe Pro Gly
                725                 730                 735
His Leu Val Asp Val Arg Gly Ala Glu Thr Leu Ser Gln Ser Tyr Gln
                740                 745                 750
Tyr Glu Val Cys Leu Thr Gly Gly Pro Gly Thr Ser Glu Phe Lys Phe
        755                 760                 765
Leu Lys Pro Val Ile Ser Asp Ile Gln Ala Gln Gly Pro Gly Arg Lys
        770                 775                 780
Gly Glu Glu Asn Ser Thr Phe Arg Asn Ser Phe Gly Phe Asn Ile Gln
785                 790                 795                 800

<210> SEQ ID NO 3
<211> LENGTH: 4726
<212> TYPE: DNA
<213> ORGANISM: Homo sapiens

<400> SEQUENCE: 3
tgccgggatc caggtctccg ggtccgcttt tggccagagg cgcggaagga agcagtgccc      60
ggcgacactg cacccatccc ggctgctttt gctgcgccct ctcagcttcc caagaaaggc     120
atcgtcatgt gatcatcacc taagaactag aacatcagca ggccctagaa gcctcactct     180
tgcccctccc tttaatatct caaaggatga cacttctgtg gtgtgtagtg agtctctact     240
tttatggaat cctgcaaagt gatgcctcag aacgctgcga tgactgggga ctagacacca     300
tgaggcaaat ccaagtgttt gaagatgagc agctcgcat caagtgccca ctctttgaac     360
acttcttgaa attcaactac agcacagccc attcagctgg ccttactctg atctggtatt     420
ggactaggca ggaccgggac cttgaggagc aattaactt ccgcctcccc gagaaccgca     480
ttagtaagga gaaagatgtg ctgtggttcc ggcccactct cctcaatgac actggcaact     540
atacctgcat gttaaggaac actacatatt gcagcaaagt tgcatttccc ttggaagttg     600
ttcaaaaaga cagctgtttc aattccccca tgaaactccc agtgcataaa ctgtatatag     660
aatatggcat tcagaggatc acttgtccaa atgtagatgg atattttcct tccagtgtca     720
aaccgactat cacttggtat atgggctgtt ataaaataca gaattttaat aatgtaatac     780
ccgaaggtat gaacttgagt ttcctcattg ccttaatttc aaataatgga aattacacat     840
```

```
gtgttgttac atatccagaa aatggacgta cgtttcatct caccaggact ctgactgtaa    900
aggtagtagg ctctccaaaa aatgcagtgc ccctgtgat ccattcacct aatgatcatg    960
tggtctatga gaaagaacca ggagaggagc tactcattcc ctgtacggtc tattttagtt   1020
ttctgatgga ttctcgcaat gaggtttggt ggaccattga tggaaaaaaa cctgatgaca   1080
tcactattga tgtcaccatt aacgaaagta taagtcatag tagaacagaa gatgaaacaa   1140
gaactcagat tttgagcatc aagaaagtta cctctgagga tctcaagcgc agctatgtct   1200
gtcatgctag aagtgccaaa ggcgaagttg ccaaagcagc caaggtgaag cagaaagtgc   1260
cagctccaag atacacagtg gaactggctt gtggttttgg agccacagtc ctgctagtgg   1320
tgattctcat tgttgtttac catgtttact ggctagagat ggtcctattt taccgggctc   1380
atttggaac agatgaaacc atttagatg gaaaagagta tgatatttat gtatcctatg    1440
caaggaatgc ggaagaagaa gaatttgtat tactgaccct ccgtggagtt ttggagaatg   1500
aatttggata caagctgtgc atctttgacc gagacagtct gcctggggga attgtcacag   1560
atgagacttt gagcttcatt cagaaaagca gacgcctcct ggttgttcta agccccaact   1620
acgtgctcca gggaacccaa gccctcctgg agctcaaggc tggcctagaa aatatggcct   1680
ctcggggcaa catcaacgtc atttttagtac agtacaaagc tgtgaaggaa acgaaggtga   1740
aagagctgaa gagggctaag acggtgctca cggtcattaa atggaaaggg gaaaaatcca   1800
agtatccaca gggcaggttc tggaagcagc tgcaggtggc catgccagtg aagaaaagtc   1860
ccaggcggtc tagcagtgat gagcagggcc tctcgtattc atctttgaaa aatgtatgaa   1920
aggaataatg aaaagggtaa aaagaacaag gggtgctcca ggaagaaaga gtccccccag   1980
tcttcattcg cagtttatgg tttcataggc aaaaataatg gtctaagcct cccaataggg   2040
ataaatttag ggtgactgtg tggctgacta ttctgcttcc tcaggcaaca ctaaagttta   2100
gaaagatatc atcaacgttc tgtcaccagt ctctgatgcc actatgttct ttgcaggcaa   2160
agacttgttc aatgcgaatt tcccttcta cattgtctat ccctgttttt atatgtctcc    2220
attcttttta aaatcttaac atatggagca gcctttccta tgaatttaaa tatgccttta   2280
aaataagtca ctgttgacag ggtcatgagt ttccgagtat agttttcttt ttatcttatt   2340
tttactcgtc cgttgaaaag ataatcaagg cctacatttt agctgaggat aatgaacttt   2400
tttcctcatt cggctgtata atacataacc acagcaagac tgacatccac ttaggatgat   2460
acaaagcagt gtaactgaaa atgtttcttt taattgattt aaaggacttg tcttctatac   2520
caccttgtc ctcatctcag gtaatttatg aaatctatgt aaacttgaaa atatttctt    2580
aattttgtt tttgctccag tcaattcctg attatccaca ggtcaaccca catttttca    2640
ttccttctcc ctatctgctt atatcgcatt gctcatttag agtttgcagg aggctccata   2700
ctaggttcag tctgaaagaa atctcctaat ggtgctatag agagggaggt aacagaaaga   2760
ctcttttagg gcattttttct gactcatgaa aagagcacag aaaaggatgt ttggcaattt   2820
gtcttttaag tcttaacctt gctaatgtga atactgggaa agtgattttt tctcactcgt   2880
ttttgttgct ccattgtaaa gggcggaggt cagtcttagt ggccttgaga gttgcttttg   2940
gcattaatat tctaagagaa ttaactgtat ttcctgtcac ctattcacta gtgcaggaaa   3000
tatacttgct ccaaataagt cagtatgaga agtcactgtc aatgaaagtt gttttgtttg   3060
ttttcagtaa tattttgctg ttttaagac ttggaaaact aagtgcagag tttacagagt    3120
ggtaaatatc tatgttacat gtagattata catatatata cacacgtgta tatgagatat   3180
atatcttata tctccacaaa cacaaattat atatatacat atccacacac atacattaca   3240
```

```
tatatctgtg tatataaatc cacatgcaca tgaaatatat atatatatat aatttgtgtg   3300
tgtgtatgtg tatgtatatg actttaaata gctatgggta caatattaaa aaccactgga   3360
actcttgtcc agttttaaa ttatgttttt actggaatgt ttttgtgtca gtgttttctg    3420
tacatattat ttgttaattc acagctcaca gagtgatagt tgtcatagtt cttgccttcc   3480
ctaagtttat ataaataact taagtattgc tacagtttat ctaggttgca gtggcatctg   3540
ctgtgcacag agcttccatg gtcactgcta agcagtagcc agccatcggg cattaattga   3600
tttcctacta tattcccagc agacacattt agaaactaag ctatgttaac ctcagtgctc   3660
aactatttga actgttgagt gataaaggaa acaaatataa ctgtaaatga atcttggtat   3720
cctgtgaaac agaataattc gtaatttaag aaagccctta tcccggtaac atgaatgttg   3780
atgaacaaat gtaaaattat atcctatatt taagtaccca taataaatca tttccctcta   3840
taagtgttat tgattatttt aaattgaaaa aagtttcact tggatgaaaa agtagaaaa    3900 gtaggtcatt cttggatcta cttttttta gccttattaa tattttccc tattagaaac    3960 cacaattact ccctctatta acccttcact tactagacca gaaagaact tattccagat    4020 aagctttgaa tatcaattct tacataaact ttaggcaaac agggaatagt ctagtcacca   4080
aaggaccatt ctcttgccaa tgctgcattc cttttgcact tttggattcc atatttatcc   4140
caaatgctgt tgggcacccc tagaaatacc ttgatgtttt ttctatttat atgcctgcct   4200
ttggtactta atttttacaaa tgctgtaata taaagcatat caagtttatg tgatacgtat   4260
cattgcaaga gaatttgttt caagattttt ttttaatgtt ccagaagatg gccaatagag   4320
aacattcaag ggaaatgggg aaacataatt tagagaacaa gaacaaacca tgtctcaaat   4380
tttttttaaa aaaattaatg gttttaaata tatgctatag ggacgttcca tgcccaggtt   4440
aacaaagaac tgtgatatat agagtgtcta attacaaaat catatacgat ttatttaatt   4500
ctcttctgta ttgtaactta gatgattccc aaggactcta ataaaaaatc acttcattgt   4560
atttggaaac aaaaacatca ttcattaatt acttattttc tttccatagg ttttaatatt   4620
ttgagagtgt cttttttatt tcattcatga acttttgtat ttttcatttt tcatttgatt   4680
tgtaaattta cttatgttaa aaataaacca tttattttca gctttg                 4726
```

<210> SEQ ID NO 4
<211> LENGTH: 570
<212> TYPE: PRT
<213> ORGANISM: Homo sapiens

<400> SEQUENCE: 4

```
Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110
```

```
Thr Cys Met Leu Arg Asn Thr Thr Tyr Cys Ser Lys Val Ala Phe Pro
        115                 120                 125
Leu Glu Val Val Gln Lys Asp Ser Cys Phe Asn Ser Pro Met Lys Leu
    130                 135                 140
Pro Val His Lys Leu Tyr Ile Glu Tyr Gly Ile Gln Arg Ile Thr Cys
145                 150                 155                 160
Pro Asn Val Asp Gly Tyr Phe Pro Ser Ser Val Lys Pro Thr Ile Thr
                165                 170                 175
Trp Tyr Met Gly Cys Tyr Lys Ile Gln Asn Phe Asn Asn Val Ile Pro
            180                 185                 190
Glu Gly Met Asn Leu Ser Phe Leu Ile Ala Leu Ile Ser Asn Asn Gly
        195                 200                 205
Asn Tyr Thr Cys Val Val Thr Tyr Pro Glu Asn Gly Arg Thr Phe His
    210                 215                 220
Leu Thr Arg Thr Leu Thr Val Lys Val Val Gly Ser Pro Lys Asn Ala
225                 230                 235                 240
Val Pro Pro Val Ile His Ser Pro Asn Asp His Val Val Tyr Glu Lys
                245                 250                 255
Glu Pro Gly Glu Glu Leu Leu Ile Pro Cys Thr Val Tyr Phe Ser Phe
            260                 265                 270
Leu Met Asp Ser Arg Asn Glu Val Trp Trp Thr Ile Asp Gly Lys Lys
        275                 280                 285
Pro Asp Asp Ile Thr Ile Asp Val Thr Ile Asn Glu Ser Ile Ser His
    290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
            340                 345                 350
Ala Pro Arg Tyr Thr Val Glu Leu Ala Cys Gly Phe Gly Ala Thr Val
        355                 360                 365
Leu Leu Val Val Ile Leu Ile Val Val Tyr His Val Tyr Trp Leu Glu
    370                 375                 380
Met Val Leu Phe Tyr Arg Ala His Phe Gly Thr Asp Glu Thr Ile Leu
385                 390                 395                 400
Asp Gly Lys Glu Tyr Asp Ile Tyr Val Ser Tyr Ala Arg Asn Ala Glu
                405                 410                 415
Glu Glu Glu Phe Val Leu Leu Thr Leu Arg Gly Val Leu Glu Asn Glu
            420                 425                 430
Phe Gly Tyr Lys Leu Cys Ile Phe Asp Arg Asp Ser Leu Pro Gly Gly
        435                 440                 445
Ile Val Thr Asp Glu Thr Leu Ser Phe Ile Gln Lys Ser Arg Arg Leu
    450                 455                 460
Leu Val Val Leu Ser Pro Asn Tyr Val Leu Gln Gly Thr Gln Ala Leu
465                 470                 475                 480
Leu Glu Leu Lys Ala Gly Leu Glu Asn Met Ala Ser Arg Gly Asn Ile
                485                 490                 495
Asn Val Ile Leu Val Gln Tyr Lys Ala Val Lys Glu Thr Lys Val Lys
            500                 505                 510
Glu Leu Lys Arg Ala Lys Thr Val Leu Thr Val Ile Lys Trp Lys Gly
        515                 520                 525
```

```
Glu Lys Ser Lys Tyr Pro Gln Gly Arg Phe Trp Lys Gln Leu Gln Val
    530                 535                 540
Ala Met Pro Val Lys Lys Ser Pro Arg Arg Ser Ser Ser Asp Glu Gln
545                 550                 555                 560
Gly Leu Ser Tyr Ser Ser Leu Lys Asn Val
                565                 570

<210> SEQ ID NO 5
<211> LENGTH: 2712
<212> TYPE: DNA
<213> ORGANISM: Homo sapiens

<400> SEQUENCE: 5
gagactttaa catcagaaaa aggatggact tgttgcagtt gctgtagcat tcaaagtcaa      60
ggtgatcatt tcaaaccaag catcagcaac aattaaaaat attcacttgg tatctgtagt     120
ttaataatgg accaacatca acatttgaat aaaacagcag agtcagcatc ttcagagaaa     180
aagaaaacaa gacgctgcaa tggattcaag atgttcttgg cagccctgtc attcagctat     240
attgctaaag cactaggtgg aatcattatg aaaatttcca tcactcaaat agaaaggaga     300
tttgacatat cctcttctct tgctggttta attgatggaa gctttgaaat tggaaatttg     360
cttgtgattg tatttgtaag ttactttgga tctaaactac acagaccgaa gttaattgga     420
attggttgtc tccttatggg aactggaagt attttgacat ctttaccaca tttcttcatg     480
ggatattata ggtattctaa agaaacccat attaatccat cagaaaattc aacatcaagt     540
ttatcaacct gtttaattaa tcaaaccttta tcattcaatg aacatcacc tgagatagta     600 gaaaagatt gtgtaaagga atctgggtca cacatgtgga tctatgtctt catggggaat     660
atgcttcgtg gcataggga aaccccccata gtaccattgg ggatttcata cattgatgat     720
tttgcaaaag aaggacattc ttccttgtat ttaggtagtt tgaatgcaat aggaatgatt     780
ggtccagtca ttggctttgc actgggatct ctgtttgcta aatgtacgt ggatattgga     840 tatgtagatc tgagcactat cagaataact cctaaggact ctcgttgggt tggagcttgg     900
tggcttggtt ccttgtgtc tggactattt tccattattt cttccatacc attttttttc     960
ttgccgaaaa atccaaataa accacaaaaa gaaagaaaaa tttcactatc attgcatgtg    1020
ctgaaaacaa atgatgatag aaatcaaaca gctaatttga ccaaccaagg aaaaaatgtt    1080
accaaaaatg tgactggttt tttccagtct ttgaaaagca tccttaccaa tcccctgtat    1140
gttatatttc tgcttttgac attgttacaa gtaagcagct ttattggttc ttttacttac    1200
gtctttaaat atatggagca acagtacggt cagtctgcat ctcatgctaa cttttttgttg    1260 ggaatcataa ccattcctac ggttgcaact ggaatgtttt taggaggatt tatcattaaa    1320
aaattcaaat tgtctttagt tggaattgcc aaattttcat ttcttacttc gatgatatcc    1380
ttcttgtttc aacttctata tttccctcta atctgcgaaa gcaaatcagt tgccggccta    1440
accttgacct atgatggaaa taattcagtg gcatctcatg tagatgtacc actttcttat    1500
tgcaactcag agtgcaattg tgatgaaagt cagtgggaac cagtctgtgg aacaatgga    1560 ataacttacc tgtcacccttg tctagcagga tgcaaatcct caagtggtat taaaaagcat    1620
acagtgtttt ataactgtag ttgtgtggaa gtaactggtc tccagaacag aaattactca    1680
gcacacttgg gtgaatgccc aagagataat acttgtacaa ggaaattttt catctatgtt    1740
gcaattcaag tcataaactc tttgttctct gcaacaggag gtaccacatt tatccttgttg    1800 actgtgaaga ttgttcaacc tgaattgaaa gcacttgcaa tgggtttcca gtcaatggtt    1860
```

-continued

```
ataagaacac taggaggaat tctagctcca atatattttg gggctctgat tgataaaaca   1920
tgtatgaagt ggtccaccaa cagctgtgga gcacaaggag cttgtaggat atataattcc   1980
gtattttttg gaagggtcta cttgggctta tctatagctt taagattccc agcacttgtt   2040
ttatatattg tttcatttt tgctatgaag aaaaaatttc aaggaaaaga taccaaggca    2100
tcggacaatg aaagaaaagt aatggatgaa gcaaacttag aattcttaaa taatggtgaa   2160
cattttgtac cttctgctgg aacagatagt aaaacatgta atttggacat gcaagacaat   2220
gctgctgcca actaacattg cattgattca ttaagatgtt attttgagg tgttcctggt    2280 ctttcactga caattccaac attctttact tacagtggac caatgaataa gtctatgcat   2340
ctataataaa ctataaaaaa tgggagtacc catggttagg atatagctat gcctttatgg   2400
ttaagattag aatatatgat ccataaaaat ttaaagtgag aggcatggtt agtgtgtgat   2460
acaataaaaa gtaattgttt ggtagttgta actgctaata aaaccagtga ctagaatata   2520
agggaggtaa aaaggacaag atagattaat agcctaaata aagagaaaag cctgatgcct   2580
ttaaaaaaaa tgaaacactt tggatgtatt acttaggcca aatctggcc tggatttatg     2640 ctataatata tattttcatg ttaagttgta tattttcag aaattataaa tattattaat     2700
ttaaaatttg aa                                                       2712
```

<210> SEQ ID NO 6
<211> LENGTH: 702
<212> TYPE: PRT
<213> ORGANISM: Homo sapiens

<400> SEQUENCE: 6

```
Met Asp Gln His Gln His Leu Asn Lys Thr Ala Glu Ser Ala Ser
1               5                   10                  15

Glu Lys Lys Lys Thr Arg Arg Cys Asn Gly Phe Lys Met Phe Leu Ala
            20                  25                  30

Ala Leu Ser Phe Ser Tyr Ile Ala Lys Ala Leu Gly Ile Ile Met
        35                  40                  45

Lys Ile Ser Ile Thr Gln Ile Glu Arg Arg Phe Asp Ile Ser Ser Ser
    50                  55                  60

Leu Ala Gly Leu Ile Asp Gly Ser Phe Glu Ile Gly Asn Leu Leu Val
65                  70                  75                  80

Ile Val Phe Val Ser Tyr Phe Gly Ser Lys Leu His Arg Pro Lys Leu
                85                  90                  95

Ile Gly Ile Gly Cys Leu Leu Met Gly Thr Gly Ser Ile Leu Thr Ser
            100                 105                 110

Leu Pro His Phe Phe Met Gly Tyr Tyr Arg Tyr Ser Lys Glu Thr His
        115                 120                 125

Ile Asn Pro Ser Glu Asn Ser Thr Ser Ser Leu Ser Thr Cys Leu Ile
    130                 135                 140

Asn Gln Thr Leu Ser Phe Asn Gly Thr Ser Pro Glu Ile Val Glu Lys
145                 150                 155                 160

Asp Cys Val Lys Glu Ser Gly Ser His Met Trp Ile Tyr Val Phe Met
                165                 170                 175

Gly Asn Met Leu Arg Gly Ile Gly Glu Thr Pro Ile Val Pro Leu Gly
            180                 185                 190

Ile Ser Tyr Ile Asp Asp Phe Ala Lys Glu Gly His Ser Ser Leu Tyr
        195                 200                 205

Leu Gly Ser Leu Asn Ala Ile Gly Met Ile Gly Pro Val Ile Gly Phe
    210                 215                 220
```

-continued

```
Ala Leu Gly Ser Leu Phe Ala Lys Met Tyr Val Asp Ile Gly Tyr Val
225                 230                 235                 240

Asp Leu Ser Thr Ile Arg Ile Thr Pro Lys Asp Ser Arg Trp Val Gly
                245                 250                 255

Ala Trp Trp Leu Gly Phe Leu Val Ser Gly Leu Phe Ser Ile Ile Ser
            260                 265                 270

Ser Ile Pro Phe Phe Phe Leu Pro Lys Asn Pro Asn Lys Pro Gln Lys
        275                 280                 285

Glu Arg Lys Ile Ser Leu Ser Leu His Val Leu Lys Thr Asn Asp Asp
290                 295                 300

Arg Asn Gln Thr Ala Asn Leu Thr Asn Gln Gly Lys Asn Val Thr Lys
305                 310                 315                 320

Asn Val Thr Gly Phe Phe Gln Ser Leu Lys Ser Ile Leu Thr Asn Pro
                325                 330                 335

Leu Tyr Val Ile Phe Leu Leu Thr Leu Leu Gln Val Ser Ser Phe
            340                 345                 350

Ile Gly Ser Phe Thr Tyr Val Phe Lys Tyr Met Glu Gln Gln Tyr Gly
        355                 360                 365

Gln Ser Ala Ser His Ala Asn Phe Leu Leu Gly Ile Thr Ile Pro
370                 375                 380

Thr Val Ala Thr Gly Met Phe Leu Gly Gly Phe Ile Ile Lys Lys Phe
385                 390                 395                 400

Lys Leu Ser Leu Val Gly Ile Ala Lys Phe Ser Phe Leu Thr Ser Met
                405                 410                 415

Ile Ser Phe Leu Phe Gln Leu Leu Tyr Phe Pro Leu Ile Cys Glu Ser
            420                 425                 430

Lys Ser Val Ala Gly Leu Thr Leu Thr Tyr Asp Gly Asn Asn Ser Val
        435                 440                 445

Ala Ser His Val Asp Val Pro Leu Ser Tyr Cys Asn Ser Glu Cys Asn
450                 455                 460

Cys Asp Glu Ser Gln Trp Glu Pro Val Cys Gly Asn Asn Gly Ile Thr
465                 470                 475                 480

Tyr Leu Ser Pro Cys Leu Ala Gly Cys Lys Ser Ser Gly Ile Lys
                485                 490                 495

Lys His Thr Val Phe Tyr Asn Cys Ser Cys Val Glu Val Thr Gly Leu
            500                 505                 510

Gln Asn Arg Asn Tyr Ser Ala His Leu Gly Glu Cys Pro Arg Asp Asn
        515                 520                 525

Thr Cys Thr Arg Lys Phe Phe Ile Tyr Val Ala Ile Gln Val Ile Asn
530                 535                 540

Ser Leu Phe Ser Ala Thr Gly Gly Thr Thr Phe Ile Leu Leu Thr Val
545                 550                 555                 560

Lys Ile Val Gln Pro Glu Leu Lys Ala Leu Ala Met Gly Phe Gln Ser
                565                 570                 575

Met Val Ile Arg Thr Leu Gly Gly Ile Leu Ala Pro Ile Tyr Phe Gly
            580                 585                 590

Ala Leu Ile Asp Lys Thr Cys Met Lys Trp Ser Thr Asn Ser Cys Gly
        595                 600                 605

Ala Gln Gly Ala Cys Arg Ile Tyr Asn Ser Val Phe Phe Gly Arg Val
610                 615                 620

Tyr Leu Gly Leu Ser Ile Ala Leu Arg Phe Pro Ala Leu Val Leu Tyr
625                 630                 635                 640
```

| Ile | Val | Phe | Ile | Phe | Ala | Met | Lys | Lys | Phe | Gln | Gly | Lys | Asp | Thr |
|---|---|---|---|---|---|---|---|---|---|---|---|---|---|---|
| | | | | 645 | | | | 650 | | | | | 655 | |

| Lys | Ala | Ser | Asp | Asn | Glu | Arg | Lys | Val | Met | Asp | Glu | Ala | Asn | Leu | Glu |
|---|---|---|---|---|---|---|---|---|---|---|---|---|---|---|---|
| | | | 660 | | | | | 665 | | | | | 670 | | |

| Phe | Leu | Asn | Asn | Gly | Glu | His | Phe | Val | Pro | Ser | Ala | Gly | Thr | Asp | Ser |
|---|---|---|---|---|---|---|---|---|---|---|---|---|---|---|---|
| | | | | 675 | | | | 680 | | | | | 685 | | |

| Lys | Thr | Cys | Asn | Leu | Asp | Met | Gln | Asp | Asn | Ala | Ala | Ala | Asn |
|---|---|---|---|---|---|---|---|---|---|---|---|---|---|
| | 690 | | | | | 695 | | | | | 700 | | |

<210> SEQ ID NO 7
<211> LENGTH: 3492
<212> TYPE: DNA
<213> ORGANISM: Homo sapiens

<400> SEQUENCE: 7

```
cagctaagac ccggagaggt ggaatttcac tttgaaattc ccttgcctcg tgagggccgg      60
cgctgggcat gctcagtagc gcggcgctg ctgctgggct gctgggctgg cgcggagtcc     120
accctgccgt ctccgccttg gcttctgggc gtccagaagg ccaggcattt gccgcctctg     180
agcgcttctg ttccccttac ccgcaacctc ctactgctct tcctctctcc ctctcttagg     240
gaggttgaag ctggtgctgg tttctgtcgg cgccacagac tgactgctct gcaaacccca     300
gccgaggacc tgaatcccgg agactagaag acccttggcg gtggctcttt ctaatagcac     360
tttacctgaa gtggggtcgt ggtggagttt ctcctccacc tctcaatgca aacactatgc     420
ggagagcagt ctgcttccct gcgctgtgcc tgctccttaa tcttcacgct gcagggtgct     480
tttcaggaaa caatgatcat ttttttggcaa ttaatcagaa gaagagtggg aagccggtat     540
tcatttataa gcattcacaa gacattgaga gagcctggaa tatagcccca caaaaaatct     600
acagacatag ctaccattcc tcttccgaag ctcaagtaag caaacgccac cagattgtca     660
attcagcatt tcctagaccc gcatatgacc cgtctctcaa tctgctggcc atggatggtc     720
aagatcttga agtggaaaat ctcccaatcc cagcagcaaa tgtaattgtg gtgacactgc     780
aaatggatgt aaacaagctg aacataacct tgcttcggat cttccgccaa ggagtggctg     840
cagctttagg actcttaccc cagcaagtgc acatcaatcg cctcattgga agaagaaca     900
gtattgaact gtttgtgtct cccataaacc gaaaaacagg aatttctgat gctctgccct     960
ctgaggaagt tcttcgttca cttaatatca atgttttgca tcaaagttta tcccagtttg    1020
gaattacaga agtctctcct gagaaaaatg ttttacaagg gcagcatgaa gcggacaaaa    1080
tctggagcaa agaaggattt tatgctgttg tcatttttct cagcatcttt gttattatag    1140
taacgtgttt gatgattctt acagattaa aagaaagatt tcagctttcc ttaagacaag    1200
acaaagagaa aaaccaggag atccacctat cgcccatcac attacagcca gcactgtccg    1260
aggcaaagac agtccacagc atggtccaac ctgagcaggc cccaaaggta ctgaatgttg    1320
tcgtggaccc tcaaggccga ggtgctcctg agatcagagc taccaccgct acctctgttt    1380
gcccttctcc tttcaaaatg aagcccatag acttcaaga gagagagggg tccaacgtat    1440
ctcttacatt ggacatgagt agcttgggga acattgaacc ctttgtgtct ataccaacac    1500
cacgggagaa ggtagcaatg gagtatctgc agtcagccag ccgaattctc acaaggtctc    1560
agctgaggga cgtcgtggca agttcacatt tactccaaag tgaattcatg gaaataccaa    1620
tgaacttttgt ggatcccaaa gaaattgata ttccgcgtca tggaactaaa atcgctata    1680
agaccatttt accaaatccc ctcagcagag tgtgtttaag accaaaaaat gtaaccgatt    1740
cattgagcac ctacattaat gctaattata ttaggggcta cagtggcaag gagaaagcct    1800
```

-continued

```
tcattgccac gcagggcccc atgatcaaca ccgtggatga tttctggcag atggtttggc    1860
aggaagacag ccctgtgatt gttatgatca aaaactcaa agaaaaaaat gagaaatgtg    1920
tgctatactg gccggaaaag agagggatat atggaaaagt tgaggttctg gttatcagtg    1980
taaatgaatg tgataactac accattcgaa accttgtctt aaagcaagga agccacaccc    2040
aacatgtgaa gcattactgg tacacctcat ggcctgatca aagactcca gacagtgccc     2100
agcccctcct acagctcatg ctggatgtag aagaagacag acttgcttcc cagggccgag    2160
ggcctgtggt tgtccactgc agtgcaggaa taggtagaac agggtgtttt attgctacat    2220
ccattggctg tcaacagctg aaagaagaag gagttgtgga tgcactaagc attgtctgcc    2280
agcttcgtat ggatagaggt ggaatggtgc aaaccagtga gcagtatgaa tttgtgcacc    2340
atgctctgtg cctgtatgag agcagacttt cagcagagac tgtccagtga gtcattgaag    2400
acttgtcaga ccatcaatct cttggggtga ttaatcaaat tacccaccca aggcttctag    2460
aaggagcttc ctgcaatgga aggaaggaga agctctgaag cccatgtatg gcatggattg    2520
tggaagactg gcaacatat ttaagatttc cagctccttg tgtatatgaa tgcatttgta    2580
agcatccccc aaattattct gaaggttttt tgatgatgga ggtatgatag gtttatcaca    2640
cagcctaagg cagatttttgt tttgtctgta ctgactctat ctgccacaca gaatgtatgt    2700
atgtaatatt cagtaataaa tgtcatcagg tgatgactgg atgagctgct gaagacattc    2760
gtattatgtg ttagatgctt taatgtttgc aaaatctgtc ttgtgaatgg actgtcagct    2820
gttaaactgt tcctgttttg aagtgctatt acctttctca gttaccagaa tcttgctgct    2880
aaagttgcaa gtgattgata atggattttt aacagagaag tcttttgtttt tgaaaaacaa    2940
aaatcaaaaa cagtaactat tttatatgga atgtgtcttt gataatatta cctattaaat    3000
gtgtatttat agtccctcct atcaaacaat tacagagcac aatgattgtc attgggtata    3060
tatgtattta ctctctatta ttgggcataa aggtggcttc tgctccagaa ctctatccac    3120
tgtatttcca catcgtgagt cattttactt taaaagggaa aaacaaattt gtagcaactc    3180
tgaagtatca agagttttaa ctacttgtct ctcttttgct aagaagggat ttttgaatat    3240
gctatctacc tggaatctct ctctcaacaa aaggtatatg ccttcaggaa tgatataatc    3300
tgtcccattt tcgaggctcc ttataaggac atttccatgt atgtccttac atttctgaaa    3360
gctttcaatc ttcaagagcc aaaaaaaatt aaaataacta ccctcagcaa acactagctg    3420
ttctgctcat atatgaattt ttaatgcagc aatgttgact ttgtttcata ctgccaataa    3480
actcttaata ct                                                        3492
```

<210> SEQ ID NO 8
<211> LENGTH: 657
<212> TYPE: PRT
<213> ORGANISM: Homo sapiens

<400> SEQUENCE: 8

```
Met Arg Arg Ala Val Cys Phe Pro Ala Leu Cys Leu Leu Asn Leu
1               5                   10                  15

His Ala Ala Gly Cys Phe Ser Gly Asn Asn Asp His Phe Leu Ala Ile
            20                  25                  30

Asn Gln Lys Lys Ser Gly Lys Pro Val Phe Ile Tyr Lys His Ser Gln
        35                  40                  45

Asp Ile Glu Lys Ser Leu Asp Ile Ala Pro Gln Lys Ile Tyr Arg His
    50                  55                  60
```

-continued

```
Ser Tyr His Ser Ser Glu Ala Gln Val Ser Lys Arg His Gln Ile
 65                  70                  75                  80

Val Asn Ser Ala Phe Pro Arg Pro Ala Tyr Asp Pro Ser Leu Asn Leu
                 85                  90                  95

Leu Ala Met Asp Gly Gln Asp Leu Glu Val Glu Asn Leu Pro Ile Pro
            100                 105                 110

Ala Ala Asn Val Ile Val Val Thr Leu Gln Met Asp Val Asn Lys Leu
            115                 120                 125

Asn Ile Thr Leu Leu Arg Ile Phe Arg Gln Gly Val Ala Ala Ala Leu
            130                 135                 140

Gly Leu Leu Pro Gln Gln Val His Ile Asn Arg Leu Ile Gly Lys Lys
145                 150                 155                 160

Asn Ser Ile Glu Leu Phe Val Ser Pro Ile Asn Arg Lys Thr Gly Ile
                165                 170                 175

Ser Asp Ala Leu Pro Ser Glu Val Leu Arg Ser Leu Asn Ile Asn
                180                 185                 190

Val Leu His Gln Ser Leu Ser Gln Phe Gly Ile Thr Glu Val Ser Pro
            195                 200                 205

Glu Lys Asn Val Leu Gln Gly Gln His Glu Ala Asp Lys Ile Trp Ser
            210                 215                 220

Lys Glu Gly Phe Tyr Ala Val Ile Phe Leu Ser Ile Phe Val Ile
225                 230                 235                 240

Ile Val Thr Cys Leu Met Ile Leu Tyr Arg Leu Lys Glu Arg Phe Gln
                245                 250                 255

Leu Ser Leu Arg Gln Asp Lys Glu Lys Asn Gln Glu Ile His Leu Ser
                260                 265                 270

Pro Ile Thr Leu Gln Pro Ala Leu Ser Glu Ala Lys Thr Val His Ser
            275                 280                 285

Met Val Gln Pro Glu Gln Ala Pro Lys Val Leu Asn Val Val Asp
            290                 295                 300

Pro Gln Gly Arg Gly Ala Pro Glu Ile Arg Ala Thr Thr Ala Thr Ser
305                 310                 315                 320

Val Cys Pro Ser Pro Phe Lys Met Lys Pro Ile Gly Leu Gln Glu Arg
                325                 330                 335

Arg Gly Ser Asn Val Ser Leu Thr Leu Asp Met Ser Ser Leu Gly Asn
                340                 345                 350

Ile Glu Pro Phe Val Ser Ile Pro Thr Pro Arg Glu Lys Val Ala Met
            355                 360                 365

Glu Tyr Leu Gln Ser Ala Ser Arg Ile Leu Thr Arg Ser Gln Leu Arg
            370                 375                 380

Asp Val Val Ala Ser Ser His Leu Leu Gln Ser Glu Phe Met Glu Ile
385                 390                 395                 400

Pro Met Asn Phe Val Asp Pro Lys Glu Ile Asp Ile Pro Arg His Gly
                405                 410                 415

Thr Lys Asn Arg Tyr Lys Thr Ile Leu Pro Asn Pro Leu Ser Arg Val
            420                 425                 430

Cys Leu Arg Pro Lys Asn Val Thr Asp Ser Leu Ser Thr Tyr Ile Asn
            435                 440                 445

Ala Asn Tyr Ile Arg Gly Tyr Ser Gly Lys Glu Lys Ala Phe Ile Ala
            450                 455                 460

Thr Gln Gly Pro Met Ile Asn Thr Val Asp Asp Phe Trp Gln Met Val
465                 470                 475                 480

Trp Gln Glu Asp Ser Pro Val Ile Val Met Ile Thr Lys Leu Lys Glu
```

|  |  | 485 |  |  |  | 490 |  |  |  | 495 |  |

Lys Asn Glu Lys Cys Val Leu Tyr Trp Pro Glu Lys Arg Gly Ile Tyr
            500                 505                 510

Gly Lys Val Glu Val Leu Val Ile Ser Val Asn Glu Cys Asp Asn Tyr
            515                 520                 525

Thr Ile Arg Asn Leu Val Leu Lys Gln Gly Ser His Thr Gln His Val
            530                 535                 540

Lys His Tyr Trp Tyr Thr Ser Trp Pro Asp His Lys Thr Pro Asp Ser
545                 550                 555                 560

Ala Gln Pro Leu Leu Gln Leu Met Leu Asp Val Glu Glu Asp Arg Leu
                565                 570                 575

Ala Ser Gln Gly Arg Gly Pro Val Val His Cys Ser Ala Gly Ile
            580                 585                 590

Gly Arg Thr Gly Cys Phe Ile Ala Thr Ser Ile Gly Cys Gln Gln Leu
            595                 600                 605

Lys Glu Glu Gly Val Val Asp Ala Leu Ser Ile Val Cys Gln Leu Arg
            610                 615                 620

Met Asp Arg Gly Gly Met Val Gln Thr Ser Glu Gln Tyr Glu Phe Val
625                 630                 635                 640

His His Ala Leu Cys Leu Tyr Glu Ser Arg Leu Ser Ala Glu Thr Val
                645                 650                 655

Gln

<210> SEQ ID NO 9
<211> LENGTH: 2733
<212> TYPE: DNA
<213> ORGANISM: Homo sapiens

<400> SEQUENCE: 9

```
ggtagtttcc aagagagacg ctgagggatg tttagaaagc ctgggacctg cagatgccat      60
gtcaggcacg cttgctcctg cataggagac taaataatct cgatatataa ggatggcagt     120
ctgttgtctt agatcagttt gagaagcagc tctggcagcg ggggtgtag gtgtgttgca     180
ctacactgaa tggaataagg ctaaaaatat gtttagtgtc tgataagaac gccagttttc     240
tcaagctctc atttaacgtc ggactttctg ttttgctttt aaagaaaaat gttttacaag     300
ggcagcatga agcggacaaa atctggagca agaaggatt ttatgctgtt gtcattttc     360
tcagcatctt tgttattata gtaacgtgtt tgatgattct ttacagatta aaagaaagat     420
ttcagctttc cttaagacaa gacaaagaga aaaccagga gatccaccta tcgcccatca     480
cattacagcc agcactgtcc gaggcaaaga cagtccacag catggtccaa cctgagcagg     540
ccccaaaggt actgaatgtt gtcgtggacc tcaaggccg aggtgctcct gagatcagag     600
ctaccaccgc tacctctgtt tgcccttctc ctttcaaaat gaagcccata ggacttcaag     660
agagaagagg gtccaacgta tctcttacat ggacatgag tagcttgggg aacattgaac     720
cctttgtgtc tataccaaca ccacgggaga aggtagcaat ggagtatctg cagtcagcca     780
gccgaattct cacaaggtct cagctgaggg acgtcgtggc aagttcacat ttactccaaa     840
gtgaattcat ggaaatacca atgaactttg tggatcccaa agaaattgat attccgcgtc     900
atggaactaa aaatcgctat aagaccattt taccaaatcc cctcagcaga gtgtgtttaa     960
gaccaaaaaa tgtaaccgat tcattgagca cctacattaa tgctaattat attaggggct    1020
acagtggcaa ggaaaagcc ttcattgcca cgcagggccc catgatcaac accgtggatg    1080
atttctggca gatggtttgg caggaagaca gccctgtgat tgttatgatc acaaaactca    1140
```

```
aagaaaaaaa tgagaaatgt gtgctatact ggccggaaaa gagagggata tatggaaaag    1200
ttgaggttct ggttatcagt gtaaatgaat gtgataacta caccattcga aaccttgtct    1260
taaagcaagg aagccacacc caacatgtga agcattactg gtacacctca tggcctgatc    1320
acaagactcc agacagtgcc cagcccctcc tacagctcat gctggatgta aagaagaca     1380 gacttgcttc ccagggccga gggcctgtgg ttgtccactg cagtgcagga ataggtagaa    1440
cagggtgttt tattgctaca tccattggct gtcaacagct gaaagaagaa ggagttgtgg    1500
atgcactaag cattgtctgc cagcttcgta tggatagagg tggaatggtg caaaccagtg    1560
agcagtatga atttgtgcac catgctctgt gcctgtatga gagcagactt tcagcagaga    1620
ctgtccagtg agtcattgaa gacttgtcag accatcaatc tcttggggtg attaatcaaa    1680
ttacccaccc aaggcttcta gaaggagctt cctgcaatgg aaggaaggag aagctctgaa    1740
gcccatgtat ggcatggatt gtggaagact gggcaacata tttaagattt ccagctcctt    1800
gtgtatatga atgcatttgt aagcatcccc caaattattc tgaaggtttt ttgatgatgg    1860
aggtatgata ggtttatcac acagcctaag gcagattttg ttttgtctgt actgactcta    1920
tctgccacac agaatgtatg tatgtaatat tcagtaataa atgtcatcag gtgatgactg    1980
gatgagctgc tgaagacatt cgtattatgt gttagatgct ttaatgtttg caaaatctgt    2040
cttgtgaatg gactgtcagc tgttaaactg ttcctgtttt gaagtgctat tacctttctc    2100
agttaccaga atcttgctgc taaagttgca agtgattgat aatggatttt taacagagaa    2160
gtctttgttt ttgaaaaaca aaaatcaaaa acagtaacta ttttatatgg aaatgtgtct    2220
tgataatatt acctattaaa tgtgtattta tagtccctcc tatcaaacaa ttacagagca    2280
caatgattgt cattgggtat atatgtattt actctctatt attgggcata aaggtggctt    2340
ctgctccaga actctatcca ctgtatttcc acatcgtgag tcattttact ttaaaaggga    2400
aaaacaaatt tgtagcaact ctgaagtatc aagagtttta actacttgtc tctcttttgc    2460
taagaaggga tttttgaata tgctatctac ctggaatctc tctctcaaca aaaggtatat    2520
gccttcagga atgatataat ctgtcccatt ttcgaggctc cttataagga catttccatg    2580
tatgtcctta catttctgaa agctttcaat cttcaagagc caaaaaaaat taaaataact    2640 acccctcagca aacactagct gttctgctca tatatgaatt tttaatgcag caatgttgac    2700
tttgtttcat actgccaata aactcttaat act                                 2733

<210> SEQ ID NO 10
<211> LENGTH: 412
<212> TYPE: PRT
<213> ORGANISM: Homo sapiens

<400> SEQUENCE: 10

Met Ile Leu Tyr Arg Leu Lys Glu Arg Phe Gln Leu Ser Leu Arg Gln
1               5                   10                  15

Asp Lys Glu Lys Asn Gln Glu Ile His Leu Ser Pro Ile Thr Leu Gln
            20                  25                  30

Pro Ala Leu Ser Glu Ala Lys Thr Val His Ser Met Val Gln Pro Glu
        35                  40                  45

Gln Ala Pro Lys Val Leu Asn Val Val Asp Pro Gln Gly Arg Gly
    50                  55                  60

Ala Pro Glu Ile Arg Ala Thr Thr Ala Thr Ser Val Cys Pro Ser Pro
65                  70                  75                  80

Phe Lys Met Lys Pro Ile Gly Leu Gln Glu Arg Arg Gly Ser Asn Val
```

```
                    85                  90                  95
Ser Leu Thr Leu Asp Met Ser Ser Leu Gly Asn Ile Glu Pro Phe Val
            100                 105                 110
Ser Ile Pro Thr Pro Arg Glu Lys Val Ala Met Glu Tyr Leu Gln Ser
        115                 120                 125
Ala Ser Arg Ile Leu Thr Arg Ser Gln Leu Arg Asp Val Val Ala Ser
    130                 135                 140
Ser His Leu Leu Gln Ser Glu Phe Met Glu Ile Pro Met Asn Phe Val
145                 150                 155                 160
Asp Pro Lys Glu Ile Asp Ile Pro Arg His Gly Thr Lys Asn Arg Tyr
                165                 170                 175
Lys Thr Ile Leu Pro Asn Pro Leu Ser Arg Val Cys Leu Arg Pro Lys
            180                 185                 190
Asn Val Thr Asp Ser Leu Ser Thr Tyr Ile Asn Ala Asn Tyr Ile Arg
        195                 200                 205
Gly Tyr Ser Gly Lys Glu Lys Ala Phe Ile Ala Thr Gln Gly Pro Met
    210                 215                 220
Ile Asn Thr Val Asp Asp Phe Trp Gln Met Val Trp Gln Glu Asp Ser
225                 230                 235                 240
Pro Val Ile Val Met Ile Thr Lys Leu Lys Glu Lys Asn Glu Lys Cys
                245                 250                 255
Val Leu Tyr Trp Pro Glu Lys Arg Gly Ile Tyr Gly Lys Val Glu Val
            260                 265                 270
Leu Val Ile Ser Val Asn Glu Cys Asp Asn Tyr Thr Ile Arg Asn Leu
        275                 280                 285
Val Leu Lys Gln Gly Ser His Thr Gln His Val Lys His Tyr Trp Tyr
    290                 295                 300
Thr Ser Trp Pro Asp His Lys Thr Pro Asp Ser Ala Gln Pro Leu Leu
305                 310                 315                 320
Gln Leu Met Leu Asp Val Glu Glu Asp Arg Leu Ala Ser Gln Gly Arg
                325                 330                 335
Gly Pro Val Val Val His Cys Ser Ala Gly Ile Gly Arg Thr Gly Cys
            340                 345                 350
Phe Ile Ala Thr Ser Ile Gly Cys Gln Gln Leu Lys Glu Glu Gly Val
        355                 360                 365
Val Asp Ala Leu Ser Ile Val Cys Gln Leu Arg Met Asp Arg Gly Gly
    370                 375                 380
Met Val Gln Thr Ser Glu Gln Tyr Glu Phe Val His His Ala Leu Cys
385                 390                 395                 400
Leu Tyr Glu Ser Arg Leu Ser Ala Glu Thr Val Gln
                405                 410

<210> SEQ ID NO 11
<211> LENGTH: 7003
<212> TYPE: DNA
<213> ORGANISM: Homo sapiens

<400> SEQUENCE: 11
ctgccggccc gcggagccgc gtccccccgg gcagccccgg gccctgcccc tatgtcccgc      60
aaggcaagcg agaatgtgga gtacacgctg cggagcctga gcagcctgat gggcgagcgg     120
cgcaggaagc agccggagcc ggacgcggcg agcgcggccg gggagtgcag cctcctggct     180
gccgccgaat cgagcaccag cctgcagagc gcgggcgcgg gcggcggcgg cgtcgggac      240 ctggagcgcg cggcgcggcg gcagttccag caggacgaga ccccgccctt cgtgtacgtg     300
```

-continued

```
gtggccgtct tctccgcgct gggcggcttc ctgtttggct atgacaccgg ggtggtgtca    360
ggggccatgc tgctgctcaa gcggcagctc agtctggacg cgctgtggca ggagctgctg    420
gtgtccagca cggtggggc ggctgccgtc tcggcgctgg ccggaggcgc cctcaacggc    480
gtcttcggcc gccgcgctgc catcctcctg gccagtgccc tcttcaccgc cggctccgcg    540
gtgctggctg cggccaacaa caaggagaca ctgctcgccg gccgcctggt cgtgggactc    600
ggcatcggca ttgcttctat gacagtgcca gtgtacattg cggaggtctc accacccaat    660
ttaagaggcc gattagtcac cattaatacc ctcttcatca caggagggca gttctttgca    720
agtgttgttg atggagcctt cagttatctc agaaggatg gatggaggta catgttggga    780
cttgcagcag ttccggcggt tatacagttt tttggctttc tcttttttgcc tgaaagccct    840 cgatggctta ttcagaaagg acagactcag aaggcccgta gaattttatc tcagatgcgt    900
ggtaaccaga ccattgatga ggaatatgat agcatcaaaa acaacattga agaggaggaa    960
aaagaggttg gctcagctgg acctgtgatc tgcagaatgc tgagttatcc cccaactcgc   1020
cgagctttaa ttgtgggttg tggcctacaa atgttccagc agctctcagg cattaacacc   1080
atcatgtact acagtgcaac cattctgcag atgtctggtg ttgaagatga tagacttgca   1140
atatggctgg cttcagttac agccttcaca aatttcattt tcacacttgt gggagtctgg   1200
cttgttgaga aggtgggccg cagaaagctt acctttggta gtttagcagg taccaccgta   1260
gcactcatta ttcttgcctt gggatttgtg ctatcagccc aagtttcccc acgcatcact   1320
tttaagccaa tagctccgtc aggtcagaac gccacttgca caagatacag ttactgtaat   1380
gaatgtatgt tggatccaga ctgcggtttc tgctacaaga tgaacaaatc aactgtcatt   1440
gactcctcct gtgttccagt taataaagca tctacaaatg aggcagcctg gggcaggtgt   1500
gaaaatgaaa ccaagttcaa aacagaagat atattttggg cttacaattt ctgccctact   1560
ccatactcct ggactgcact tctgggcctt attttatatc ttgtcttctt tgcacctgga   1620
atgggaccaa tgccttggac tgtgaattct gaaatatatc cccttttgggc aagaagtaca   1680 ggaaatgcat gttcatctgg aataaactgg attttcaatg tcctggtttc actaacattt   1740
ttacacacag cagagtatct tacatactat ggagctttct tcctctatgc tggatttgct   1800
gctgtgggac tcctttttcat ctatggctgt cttcctgaga ccaaaggcaa aaaattagag   1860
gaaattgaat cactctttga caacaggcta tgtacatgtg gcacttcaga ttctgatgaa   1920
gggagatata ttgaatatat tcgggtaaag ggaagtaact atcatctttc tgacaatgat   1980
gcttctgatg tggaataatt ttcagctgct catatattta gttatttaaa caaactgggg   2040
ggagaagaac agcaattggt gacttcactg ccctgcttct aatctggttc tttccacagc   2100
ctagttttga ttgacttcat attctagaat acttgattag gaggaagata caaccatgat   2160 gactttttt ttccacaagg aacaatattt taaaaatat ttacagagat tttaatctaa   2220
taattcttaa gcaaatgtgt gtaatgcctt cctgaaatag tctaaaatga atattgtacc   2280
cagtgacttc agtggtatcc ttttttccta agaccattta taattattag tggcaacaga   2340
gtcagtgcta atctagccaa attacatatg tataatatat ttataaagga ttctgggaga   2400
tggtccaagg gtgttctgtg tcaaaagatg gccattggc cctcagtttt cctacagagt   2460
agtggcttat ctctgatcag ctgttacaaa ctaaattcca tgtaagcttt catcaacaaa   2520
ttccaaagtg cctcctacaa gggcacagct gtccgtatct cctttggatt ccatattttt   2580
gtttctctcc aattcagata ttgggagttc ttcagatact gactctgcac actatctttt   2640
```

-continued

```
gaacattatg aaaatataat ctgtcgggtt gttttcatac ttcttttttt tgcatcagtg    2700
ataaggcata catttgcgca gatgagctag gaagttttga gaagtacctt ttatgttcag    2760
aaagtaacag attaaaggtt tttatgggtt ccaaattggt tagtcactta ggtatgcaat    2820
tataaatgca aaatagtgcc agatctttaa ctgtatatca gggtcagttt ttgttcatgc    2880
ccaaatcact acaccttcct cattggcctt ggagtcctac tatttcgtgc cttcatttgt    2940
gttacataca tagctgcaag caaaccattt ttccccttc ttttattcaa acaataattt    3000
ttgaaacaaa aaagaggaag gaaatcagtg gcagaaataa tcctgctgtt attggtgttt    3060
gtttaataaa aataatggga cttttttctt aacttttat tagctcttcc taagggaaat    3120
gtcacatatt attatttaat tgtacttgtc tttttttact ttaagagcat aaactcgttt    3180
ttattttgca cactttctc attttcctga gaatttacca gaaaaaaaaa agatacatag    3240
atttgtctct gtgttttct tattcttggc ttagttttc cttcttgtgt aaaaattgag    3300
attgcctatt ggaacagata attggttcta atatagcacg tctataagaa atgcaggctt    3360
aattatattt ccacaatgtc tttccaaggt attcattggt ttttatggta attcatcact    3420
gaactcttaa ttttgcttt tctattaaga actatatagt atgtacaaaa ttacttgatc    3480
acaaaattac ttgctagttc caggaaaaat atgaatgaat cttctgtggc cagttaggaa    3540
tacatcagtt tgatgcattt ttaaatggct ctaaacatct aataaggtac tgtatttgga    3600
gagaaaaggt ggctatctcc atattcaaaa tatttcttcc agtctccaag atactctatt    3660
cttttaatgt ctggcttgtt cctatcacag ttatcaagct gagaatacag ctgaggaagt    3720
tcattctcta agtcaccaga ggtataatat gtgcttaaac tgtcaattta gtgccctaaa    3780
aatccattaa ccaaaaacaa aaacgttttc tcccttggt catttcatat aataaaaaaa    3840
attaatattt tatagaggtt ttttccttga attaggtgct ttaacaattg atttccaagg    3900
gaatattagt attgatttt tcctcagaaa agcagatatg atttaatagg gaaaattatt    3960
attctattga tatttcttat ctcataagaa atttcttatc taatattta cacaggtaaa    4020 ttgaagtgaa aaataagcta ctatatggta caatcaaaat ataataagga gaaaagtag    4080 accaataaag tgctctctaa aaatttattt tttggactta atcaaaataa ttgcctcaat    4140
ccttctcttt attgtatatg tagccttaac taactatata cttataaact cagctgggct    4200
gatgcacagt aactttatta aaggagaaac tggactcttg ttatttccta aagcagaaca    4260
tggcctgttc tccctgatat aagaaaacaa tgttttcaac tttataacca taaatgcaca    4320
taataacagg gaaaattagc cacagttctc ctcccctact cccctgagcc cctactttaa    4380
aggactattt gttatttata tagtgttaaa gataatattc catatctttg aagtataaga    4440
cagagaggca cagtataaga attatttata acttttaga aacaattact tgaaaaggaa    4500
ccttatacaa ttagggtatt attttagat ttggtgaaca tttatagtat attaaaaatt    4560
aaatgtttaa attttgcagg ttttttata ttaggcacct tttaagttcc cagcatattt    4620
ggctaccact atcaacttgg aaacattcca tttgtagtat catcaaatat atattttgta    4680
ggacaattta tatgatgtg gatttgacct accatattaa agcagacaca gattacgtat    4740
catgctttca accaaaatta cagacttcct ttgaaacatg ctgcagattt gatagaggta    4800
tattatgtct taggaaaata caatgaagaa ggtccaaatc cctattgagg ctggatgtct    4860
gatctgcact agacttaaga ggatatatca tttcatctgc atataaacac atagggctga    4920
atgtgatgtc aaaagggttt gccgttaata attttcttca atgtaaacat tcctaataat    4980
tttgattgtt gctccttagt caatcatttc ccaaaacatg attattttta atatatgtaa    5040
```

```
aatatttaaa taataaataa taaaaggtaa tgtgtccatt ttaaattttg ttcccagcca      5100
tacacagtag ttccctgata caaaatgcta tgagaatacc gactatttt tcataattta       5160
attttaccac tgaacctgat tttagtacat aagagtctaa atattaagtt attcactcta      5220
aaaggggaaa tcagtaaaag caaggaattt atgaaatttt tgctgtaatt tcagtatctg      5280
ttatacaggg gaagaatgat caggaaaaat ataagctgac aacttaccct tttgcttttt      5340
aacaacaaaa taatattgaa aatatattag ataactcac agatccagaa gttggtggaa       5400
atggaagaat gttttagaaa ataccatcca tatgtttatc taagaaagtc tcagaattta     5460
gtgacactaa tacagttcat aaatactgta atacagtgga gagagttgga atgttatttt    5520
ggttttattt catcagcaca attattaaaa acaacaaaat taatgagacg ttttgttata    5580
atcagatttt ttttaccat attgcaagtt ataaaatgtc aacttatact aagtacctaa     5640
caactgactt ttattcactt gttgtgacaa gttttaatt accaaattaa gaccttttca     5700
gtatctatga gtaaaagaaa tagatgatta tatcagacca ggagcagaga atttataata    5760
tgtgctttat agcaaaatgt attaaattgt ggttaaaatt tatagctcat atgtagctgc    5820
tgccaataag aaggctcaga attgttctgt ggattaattt ttacatcctg ttttctgtca    5880
cttttaccaa tcttcttggc ctcatgtaca ataatgtaaa gccaatttga tgaaatggtt    5940
caggttgtag cagtctataa attgtcggta cattcagctc ttctaggtga gcaatactgc    6000
tgctatttt ctagaaatag caatcattta aaaatgccaa atagctaact gctaccaact    6060
ctttcttgta tcttgtctct ttagagaagg aaattttgt gtgccagtaa tcatcaaaga    6120
ggtgtttat aagagtgttg atgttcagaa gttcatgaaa gtattttatc cgtataattt     6180
gctagtgagc taaaacaata taatttatgt aaatctttat atgtacaaaa tatatagtct    6240
gttgtacttg agtaatttgg tctatggaat tttaaatgcc ttcatttagc agtaatattc    6300
acatttttat tttagacagt taagttcatg tgtttgattt tgtcatgtca gcataaatga    6360
gaaaaagaag tggatcatgc agctaatgag taaccaacat tttgtaaagt tttaaagttt    6420
tagcaaacaa cattattcca tctcatttaa aggttaaaaa agaagagaca actctagcca    6480
aagtagaaat ttatattcta cacgtccaaa ctgtctccta gcagcttttg gactatatat    6540
cacttgatgt taaagtatct tttatttgta ataaatattc aaatttctat ttagaagctc    6600
taatgtatac ctagattaaa tcaaatcaca gttttatgct tttaaaatat atgtatttca    6660
aactgtatat tttaatttct gagtgcatgt tatatagtat ttaatacttc agatgtcttg    6720
gcaaattcaa tataagtatt tattcccaca agcgatatat gggatatctc ttaaaaatta    6780
tgaatatgta ccatttcctt caaagtcatc ctagcctatg ctgtatcaaa agtattgtat    6840
attttatgga gatttagtga tatacatgta aatgtttttt aagttatttt attgaagttc    6900
aatctttaca taaattaaa atctttttt aaaaaagtg tcagtgccag aactgtaaat        6960
gaaaataatc aaataaaagt taaaataatt cattactcat taa                       7003
```

<210> SEQ ID NO 12
<211> LENGTH: 629
<212> TYPE: PRT
<213> ORGANISM: Homo sapiens

<400> SEQUENCE: 12

Met Gly Glu Arg Arg Arg Lys Gln Pro Glu Pro Asp Ala Ala Ser Ala
1               5                   10                  15

Ala Gly Glu Cys Ser Leu Leu Ala Ala Ala Glu Ser Ser Thr Ser Leu

```
                20                  25                  30
Gln Ser Ala Gly Ala Gly Gly Gly Val Gly Asp Leu Glu Arg Ala
            35                  40                  45
Ala Arg Arg Gln Phe Gln Gln Asp Glu Thr Pro Ala Phe Val Tyr Val
    50                  55                  60
Val Ala Val Phe Ser Ala Leu Gly Gly Phe Leu Phe Gly Tyr Asp Thr
65                  70                  75                  80
Gly Val Val Ser Gly Ala Met Leu Leu Leu Lys Arg Gln Leu Ser Leu
                85                  90                  95
Asp Ala Leu Trp Gln Glu Leu Leu Val Ser Ser Thr Val Gly Ala Ala
            100                 105                 110
Ala Val Ser Ala Leu Ala Gly Gly Ala Leu Asn Gly Val Phe Gly Arg
        115                 120                 125
Arg Ala Ala Ile Leu Leu Ala Ser Ala Leu Phe Thr Ala Gly Ser Ala
    130                 135                 140
Val Leu Ala Ala Ala Asn Asn Lys Glu Thr Leu Leu Ala Gly Arg Leu
145                 150                 155                 160
Val Val Gly Leu Gly Ile Gly Ile Ala Ser Met Thr Val Pro Val Tyr
                165                 170                 175
Ile Ala Glu Val Ser Pro Pro Asn Leu Arg Gly Arg Leu Val Thr Ile
            180                 185                 190
Asn Thr Leu Phe Ile Thr Gly Gly Gln Phe Phe Ala Ser Val Val Asp
        195                 200                 205
Gly Ala Phe Ser Tyr Leu Gln Lys Asp Gly Trp Arg Tyr Met Leu Gly
    210                 215                 220
Leu Ala Ala Val Pro Ala Val Ile Gln Phe Phe Gly Phe Leu Phe Leu
225                 230                 235                 240
Pro Glu Ser Pro Arg Trp Leu Ile Gln Lys Gly Gln Thr Gln Lys Ala
                245                 250                 255
Arg Arg Ile Leu Ser Gln Met Arg Gly Asn Gln Thr Ile Asp Glu Glu
            260                 265                 270
Tyr Asp Ser Ile Lys Asn Asn Ile Glu Glu Glu Lys Glu Val Gly
        275                 280                 285
Ser Ala Gly Pro Val Ile Cys Arg Met Leu Ser Tyr Pro Pro Thr Arg
    290                 295                 300
Arg Ala Leu Ile Val Gly Cys Gly Leu Gln Met Phe Gln Gln Leu Ser
305                 310                 315                 320
Gly Ile Asn Thr Ile Met Tyr Tyr Ser Ala Thr Ile Leu Gln Met Ser
                325                 330                 335
Gly Val Glu Asp Asp Arg Leu Ala Ile Trp Leu Ala Ser Val Thr Ala
            340                 345                 350
Phe Thr Asn Phe Ile Phe Thr Leu Val Gly Val Trp Leu Val Glu Lys
        355                 360                 365
Val Gly Arg Arg Lys Leu Thr Phe Gly Ser Leu Ala Gly Thr Thr Val
    370                 375                 380
Ala Leu Ile Ile Leu Ala Leu Gly Phe Val Leu Ser Ala Gln Val Ser
385                 390                 395                 400
Pro Arg Ile Thr Phe Lys Pro Ile Ala Pro Ser Gly Gln Asn Ala Thr
                405                 410                 415
Cys Thr Arg Tyr Ser Tyr Cys Asn Glu Cys Met Leu Asp Pro Asp Cys
            420                 425                 430
Gly Phe Cys Tyr Lys Met Asn Lys Ser Thr Val Ile Asp Ser Ser Cys
        435                 440                 445
```

| | | | | | | | | | | | | |
|---|---|---|---|---|---|---|---|---|---|---|---|---|
|Val|Pro|Val|Asn|Lys|Ala|Ser|Thr|Asn|Glu|Ala|Ala|Trp|Gly|Arg|Cys|
| |450| | | |455| | | |460| | | | | | |

Val Pro Val Asn Lys Ala Ser Thr Asn Glu Ala Ala Trp Gly Arg Cys
    450             455             460

Glu Asn Glu Thr Lys Phe Lys Thr Glu Asp Ile Phe Trp Ala Tyr Asn
465             470             475             480

Phe Cys Pro Thr Pro Tyr Ser Trp Thr Ala Leu Leu Gly Leu Ile Leu
                485             490             495

Tyr Leu Val Phe Phe Ala Pro Gly Met Gly Pro Met Pro Trp Thr Val
            500             505             510

Asn Ser Glu Ile Tyr Pro Leu Trp Ala Arg Ser Thr Gly Asn Ala Cys
            515             520             525

Ser Ser Gly Ile Asn Trp Ile Phe Asn Val Leu Val Ser Leu Thr Phe
        530             535             540

Leu His Thr Ala Glu Tyr Leu Thr Tyr Tyr Gly Ala Phe Phe Leu Tyr
545             550             555             560

Ala Gly Phe Ala Ala Val Gly Leu Leu Phe Ile Tyr Gly Cys Leu Pro
                565             570             575

Glu Thr Lys Gly Lys Lys Leu Glu Glu Ile Glu Ser Leu Phe Asp Asn
            580             585             590

Arg Leu Cys Thr Cys Gly Thr Ser Asp Ser Asp Glu Gly Arg Tyr Ile
        595             600             605

Glu Tyr Ile Arg Val Lys Gly Ser Asn Tyr His Leu Ser Asp Asn Asp
    610             615             620

Ala Ser Asp Val Glu
625

<210> SEQ ID NO 13
<211> LENGTH: 2268
<212> TYPE: DNA
<213> ORGANISM: Homo sapiens

<400> SEQUENCE: 13

```
aatatcttgc atgttacaga tttcactgct cccaccagct tggagacaac atgtggttct     60
tgacaactct gctcctttgg gttccagttg atgggcaagt ggacaccaca aaggcagtga    120
tcactttgca gcctccatgg gtcagcgtgt tccaagagga aaccgtaacc ttgcactgtg    180
aggtgctcca tctgcctggg agcagctcta cacagtggtt tctcaatggc acagccactc    240
agacctcgac ccccagctac agaatcacct ctgccagtgt caatgacagt ggtgaataca    300
ggtgccagag aggtctctca gggcgaagtg accccataca gctggaaatc acagagagct    360
ggctactact gcaggtctcc agcagagtct tcacggaagg agaacctctg gccttgaggt    420
gtcatgcgtg gaaggataag ctggtgtaca atgtgcttta ctatcgaaat ggcaaagcct    480
ttaagttttt ccactggaat tctaacctca ccattctgaa aaccaacata agtcacaatg    540
gcacctacca ttgctcaggc atgggaaagc atcgctacac atcagcagga atatctgtca    600
ctgtgaaaga gctatttcca gctccagtgc tgaatgcatc tgtgacatcc ccactcctgg    660
agggaatct ggtcacctg agctgtgaaa caaagttgct cttgcagagg cctggtttgc    720
agctttactt ctccttctac atgggcagca agaccctgcg aggcaggaac acatcctctg    780
aataccaaat actaactgct agaagagaag actctgggtt atactggtgc gaggctgcca    840
cagaggatgg aaatgtcctt aagcgcagcc ctgagttgga gcttcaagtg cttggcctcc    900
agttaccaac tcctgtctgg tttcatgtcc ttttctatct ggcagtggga ataatgtttt    960
tagtgaacac tgttctctgg gtgacaatac gtaaagaact gaaagaaag aaaaagtggg  1020
```

```
atttagaaat ctctttggat tctggtcatg agaagaaggt aatttccagc cttcaagaag    1080
acagacattt agaagaagag ctgaaatgtc aggaacaaaa agaagaacag ctgcaggaag    1140
gggtgcaccg gaaggagccc caggggggcca cgtagcagcg gctcagtggg tggccatcga    1200
tctggaccgt ccctgccca cttgctcccc gtgagcactg cgtacaaaca tccaaaagtt    1260
caacaacacc agaactgtgt gtctcatggt atgtaactct taaagcaaat aaatgaactg    1320
acttcaactg ggatacattt ggaaatgtgg tcatcaaaga tgacttgaaa tgaggcctac    1380
tctaaagaat tcttgaaaaa cttacaagtc aagcctagcc tgataatcct attacatagt    1440
ttgaaaaata gtattttatt tctcagaaca aggtaaaaag gtgagtgggt gcatatgtac    1500
agaagattaa gacagagaaa cagacagaaa gagacacaca cacagccagg agtgggtaga    1560
tttcagggag acaagaggga atagtataga caataaggaa ggaaatagta cttacaaatg    1620
actcctaagg gactgtgaga ctgagagggc tcacgcctct gtgttcagga tacttagttc    1680
atggcttttc tctttgactt tactaaaaga gaatgtctcc atacgcgttc taggcataca    1740 aggggggtaac tcatgatgag aaatggatgt gttattcttg ccctctcttt tgaggctctc    1800
tcataacccc tctatttcta gagacaacaa aaatgctgcc agtcctaggc ccctgccctg    1860
taggaaggca gaatgtaact gttctgtttg tttaacgatt aagtccaaat ctccaagtgc    1920
ggcactgcaa agagacgctt caagtgggga gaagcggcga taccatagag tccagatctt    1980
gcctccagag atttgcttta ccttcctgat tttctggtta ctaattagct tcaggatacg    2040
ctgctctcat acttgggctg tagtttggag acaaaatatt ttcctgccac tgtgtaacat    2100
agctgaggta aaaactgaac tatgtaaatg actctactaa aagtttaggg aaaaaaaaca    2160
ggaggagtat gacacaaaaa aaaaaaaaaa aaaaaaaaaa aaaaaaaaaa aaaaaaaaaa    2220
aaaaaaaaaa aaaaaaaaaa aaaaaaaaaa aaaaaaaaa aaaaaaa                  2268

<210> SEQ ID NO 14
<211> LENGTH: 374
<212> TYPE: PRT
<213> ORGANISM: Homo sapiens

<400> SEQUENCE: 14

Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160
```

```
Ser His Asn Gly Thr Tyr His Cys Ser Gly Met Gly Lys His Arg Tyr
                165                 170                 175
Thr Ser Ala Gly Ile Ser Val Thr Val Lys Glu Leu Phe Pro Ala Pro
            180                 185                 190
Val Leu Asn Ala Ser Val Thr Ser Pro Leu Leu Glu Gly Asn Leu Val
        195                 200                 205
Thr Leu Ser Cys Glu Thr Lys Leu Leu Leu Gln Arg Pro Gly Leu Gln
    210                 215                 220
Leu Tyr Phe Ser Phe Tyr Met Gly Ser Lys Thr Leu Arg Gly Arg Asn
225                 230                 235                 240
Thr Ser Ser Glu Tyr Gln Ile Leu Thr Ala Arg Arg Glu Asp Ser Gly
                245                 250                 255
Leu Tyr Trp Cys Glu Ala Ala Thr Glu Asp Gly Asn Val Leu Lys Arg
            260                 265                 270
Ser Pro Glu Leu Glu Leu Gln Val Leu Gly Leu Gln Leu Pro Thr Pro
        275                 280                 285
Val Trp Phe His Val Leu Phe Tyr Leu Ala Val Gly Ile Met Phe Leu
    290                 295                 300
Val Asn Thr Val Leu Trp Val Thr Ile Arg Lys Glu Leu Lys Arg Lys
305                 310                 315                 320
Lys Lys Trp Asp Leu Glu Ile Ser Leu Asp Ser Gly His Glu Lys Lys
                325                 330                 335
Val Ile Ser Ser Leu Gln Glu Asp Arg His Leu Glu Glu Leu Lys
            340                 345                 350
Cys Gln Glu Gln Lys Glu Glu Gln Leu Gln Glu Gly Val His Arg Lys
        355                 360                 365
Glu Pro Gln Gly Ala Thr
    370

<210> SEQ ID NO 15
<211> LENGTH: 1284
<212> TYPE: DNA
<213> ORGANISM: Homo sapiens

<400> SEQUENCE: 15
ctgtgattct cactatactg gtcctgagga aagggcttct gtgaactgcg gttttagtt      60 tttattgtgg ttcttagttc tcatgagacc cctcttgagg atatgtgcct atctggtgcc    120
tctgctctcc actagttgag tgaaaggaag gaggtaattt accaccatgt ttggttcctg    180
tttataagat gttttaagaa agatctgaaa cagattttct gaagaaagca gaagctctct    240
tcccattatg acttcggaaa tcacttatgc tgaagtgagg ttcaaaaatg aattcaagtc    300
ctcaggcatc aacacagcct cttctgcagc ttccaaggag aggactgccc ctcacaaaag    360
taataccgga ttccccaagc tgcttttgtgc ctcactgttg atattttcc tgctattggc    420 aatctcattc tttattgctt ttgtcatttt ctttcaaaaa tattctcagc ttcttgaaaa    480
aaagactaca aaagagctgg ttcatacaac attggagtgt gtgaaaaaaa atatgcccgt    540
ggaagagaca gcctggagct gttgcccaaa gaattggaag tcatttagtt ccaactgcta    600
ctttatttct actgaatcag catcttggca agacagtgag aaggactgtg ctagaatgga    660
ggctcacctg ctggtgataa acactcaaga agagcaggat ttcatcttcc agaatctgca    720
agaagaatct gcttattttg tggggctctc agatccagaa ggtcagcgac attggcaatg    780
ggttgatcag acaccataca atgaaagttc cacattctgg catccacgtg agcccagtga    840
```

```
tcccaatgag cgctgcgttg tgctaaattt tcgtaaatca cccaaaagat ggggctggaa      900
tgatgttaat tgtcttggtc ctcaaaggtc agtttgtgag atgatgaaga tccacttatg      960
aactgaacat tctccatgaa caggtggttg gattggtatc tgtcattgta gggatagata     1020
ataagctctt cttattcatg tgtaagggag gtccatagaa tttaggtggt ctgtcaacta     1080
ttctacttat gagagaattg gtctgtacat tgactgattc actttttcat aaagtgagca     1140
tttattgagc attttttcat gtgccagagc ctgtactgga ggcccccatt gtgcacacat     1200
ggagagaaca tgagtctctc ttaattttta tctggttgct aaagaattat ttaccaataa     1260
aattatatga tgtggtgtct caaa                                            1284
```

<210> SEQ ID NO 16
<211> LENGTH: 237
<212> TYPE: PRT
<213> ORGANISM: Homo sapiens

<400> SEQUENCE: 16

```
Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Ala Ser Lys Glu Arg
            20                  25                  30

Thr Ala Pro His Lys Ser Asn Thr Gly Phe Pro Lys Leu Leu Cys Ala
        35                  40                  45

Ser Leu Leu Ile Phe Phe Leu Leu Ala Ile Ser Phe Phe Ile Ala
    50                  55                  60

Phe Val Ile Phe Phe Gln Lys Tyr Ser Gln Leu Leu Glu Lys Lys Thr
65                  70                  75                  80

Thr Lys Glu Leu Val His Thr Thr Leu Glu Cys Val Lys Lys Asn Met
                85                  90                  95

Pro Val Glu Glu Thr Ala Trp Ser Cys Cys Pro Lys Asn Trp Lys Ser
            100                 105                 110

Phe Ser Ser Asn Cys Tyr Phe Ile Ser Thr Glu Ser Ala Ser Trp Gln
        115                 120                 125

Asp Ser Glu Lys Asp Cys Ala Arg Met Glu Ala His Leu Leu Val Ile
    130                 135                 140

Asn Thr Gln Glu Glu Gln Asp Phe Ile Phe Gln Asn Leu Gln Glu Glu
145                 150                 155                 160

Ser Ala Tyr Phe Val Gly Leu Ser Asp Pro Glu Gly Gln Arg His Trp
                165                 170                 175

Gln Trp Val Asp Gln Thr Pro Tyr Asn Glu Ser Ser Thr Phe Trp His
            180                 185                 190

Pro Arg Glu Pro Ser Asp Pro Asn Glu Arg Cys Val Val Leu Asn Phe
        195                 200                 205

Arg Lys Ser Pro Lys Arg Trp Gly Trp Asn Asp Val Asn Cys Leu Gly
    210                 215                 220

Pro Gln Arg Ser Val Cys Glu Met Met Lys Ile His Leu
225                 230                 235
```

<210> SEQ ID NO 17
<211> LENGTH: 1167
<212> TYPE: DNA
<213> ORGANISM: Homo sapiens

<400> SEQUENCE: 17

```
ctgtgattct cactatactg gtcctgagga aagggcttct gtgaactgcg gttttagtt       60
```

-continued

```
tttattgtgg ttcttagttc tcatgagacc cctcttgagg atatgtgcct atctggtgcc       120
tctgctctcc actagttgag tgaaaggaag gaggtaattt accaccatgt ttggttcctg       180
tttataagat gttttaagaa agatctgaaa cagattttct gaagaaagca gaagctctct       240
tcccattatg acttcggaaa tcacttatgc tgaagtgagg ttcaaaaatg aattcaagtc       300
ctcaggcatc aacacagcct cttctgcagt tttctttcaa aaatattctc agcttcttga       360
aaaaaagact acaaagagc tggttcatac aacattggag tgtgtgaaaa aaatatgcc        420 cgtggaagag acagcctgga gctgttgccc aaagaattgg aagtcattta gttccaactg       480
ctactttatt tctactgaat cagcatcttg caagacagt gagaaggact gtgctagaat        540
ggaggctcac ctgctggtga taaacactca agaagagcag gatttcatct tccagaatct      600
gcaagaagaa tctgcttatt ttgtggggct ctcagatcca aaggtcagc gacattggca       660 atgggttgat cagacaccat acaatgaaag ttccacattc tggcatccac gtgagcccag       720
tgatcccaat gagcgctgcg ttgtgctaaa ttttcgtaaa tcacccaaaa gatggggctg       780
gaatgatgtt aattgtcttg gtcctcaaag gtcagtttgt gagatgatga agatccactt       840
atgaactgaa cattctccat gaacaggtgg ttggattggt atctgtcatt gtagggatag       900
ataataagct cttcttattc atgtgtaagg gaggtccata gaattaggt ggtctgtcaa        960 ctattctact tatgagagaa ttggtctgta cattgactga ttcactttt cataaagtga       1020 gcatttattg agcatttttt catgtgccag agcctgtact ggaggccccc attgtgcaca     1080
catggagaga acatgagtct ctcttaattt ttatctggtt gctaaagaat tatttaccaa     1140
taaaattata tgatgtggtg tctcaaa                                          1167
```

<210> SEQ ID NO 18
<211> LENGTH: 198
<212> TYPE: PRT
<213> ORGANISM: Homo sapiens

<400> SEQUENCE: 18

```
Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Val Phe Phe Gln Lys
            20                  25                  30

Tyr Ser Gln Leu Leu Glu Lys Lys Thr Thr Lys Glu Leu Val His Thr
        35                  40                  45

Thr Leu Glu Cys Val Lys Lys Asn Met Pro Val Glu Glu Thr Ala Trp
    50                  55                  60

Ser Cys Cys Pro Lys Asn Trp Lys Ser Phe Ser Ser Asn Cys Tyr Phe
65                  70                  75                  80

Ile Ser Thr Glu Ser Ala Ser Trp Gln Asp Ser Glu Lys Asp Cys Ala
                85                  90                  95

Arg Met Glu Ala His Leu Leu Val Ile Asn Thr Gln Glu Glu Gln Asp
            100                 105                 110

Phe Ile Phe Gln Asn Leu Gln Glu Glu Ser Ala Tyr Phe Val Gly Leu
        115                 120                 125

Ser Asp Pro Glu Gly Gln Arg His Trp Gln Trp Val Asp Gln Thr Pro
    130                 135                 140

Tyr Asn Glu Ser Ser Thr Phe Trp His Pro Arg Glu Pro Ser Asp Pro
145                 150                 155                 160

Asn Glu Arg Cys Val Val Leu Asn Phe Arg Lys Ser Pro Lys Arg Trp
                165                 170                 175
```

Gly Trp Asn Asp Val Asn Cys Leu Gly Pro Gln Arg Ser Val Cys Glu
            180                 185                 190

Met Met Lys Ile His Leu
        195

<210> SEQ ID NO 19
<211> LENGTH: 1068
<212> TYPE: DNA
<213> ORGANISM: Homo sapiens

<400> SEQUENCE: 19

| | | | | | |
|---|---|---|---|---|---|
| ctgtgattct | cactatactg | gtcctgagga | aagggcttct | gtgaactgcg | gttttagtt | 60 |
| tttattgtgg | ttcttagttc | tcatgagacc | cctcttgagg | atatgtgcct | atctggtgcc | 120 |
| tctgctctcc | actagttgag | tgaaaggaag | gaggtaattt | accaccatgt | ttggttcctg | 180 |
| tttataagat | gttttaagaa | agatctgaaa | cagattttct | gaagaaagca | gaagctctct | 240 |
| tcccattatg | acttcggaaa | tcacttatgc | tgaagtgagg | ttcaaaaatg | aattcaagtc | 300 |
| ctcaggcatc | aacacagcct | cttctgcaga | gacagcctgg | agctgttgcc | caagaattg | 360 |
| gaagtcattt | agttccaact | gctactttat | ttctactgaa | tcagcatctt | ggcaagacag | 420 |
| tgagaaggac | tgtgctagaa | tggaggctca | cctgctggtg | ataaacactc | aagaagagca | 480 |
| ggatttcatc | ttccagaatc | tgcaagaaga | atctgcttat | tttgtggggc | tctcagatcc | 540 |
| agaaggtcag | cgacattggc | aatgggttga | tcagacacca | tacaatgaaa | gttccacatt | 600 |
| ctggcatcca | cgtgagccca | gtgatcccaa | tgagcgctgc | gttgtgctaa | attttcgtaa | 660 |
| atcacccaaa | agatggggct | ggaatgatgt | taattgtctt | ggtcctcaaa | ggtcagtttg | 720 |
| tgagatgatg | aagatccact | tatgaactga | acattctcca | tgaacaggtg | gttggattgg | 780 |
| tatctgtcat | tgtagggata | gataataagc | tcttcttatt | catgtgtaag | ggaggtccat | 840 |
| agaatttagg | tggtctgtca | actattctac | ttatgagaga | attggtctgt | acattgactg | 900 |
| attcactttt | tcataaagtg | agcatttatt | gagcattttt | tcatgtgcca | gagcctgtac | 960 |
| tggaggcccc | cattgtgcac | acatggagag | aacatgagtc | tctcttaatt | tttatctggt | 1020 |
| tgctaaagaa | ttatttacca | ataaaattat | atgatgtggt | gtctcaaa | | 1068 |

<210> SEQ ID NO 20
<211> LENGTH: 204
<212> TYPE: PRT
<213> ORGANISM: Homo sapiens

<400> SEQUENCE: 20

Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Ala Ser Lys Glu Arg
            20                  25                  30

Thr Ala Pro His Lys Ser Asn Thr Gly Phe Pro Lys Leu Leu Cys Ala
        35                  40                  45

Ser Leu Leu Ile Phe Phe Leu Leu Ala Ile Ser Phe Phe Ile Ala
    50                  55                  60

Phe Val Lys Thr Ala Trp Ser Cys Cys Pro Lys Asn Trp Lys Ser Phe
65                  70                  75                  80

Ser Ser Asn Cys Tyr Phe Ile Ser Thr Glu Ser Ala Ser Trp Gln Asp
                85                  90                  95

Ser Glu Lys Asp Cys Ala Arg Met Glu Ala His Leu Leu Val Ile Asn
            100                 105                 110

```
Thr Gln Glu Glu Gln Asp Phe Ile Phe Gln Asn Leu Gln Glu Glu Ser
        115                 120                 125
Ala Tyr Phe Val Gly Leu Ser Asp Pro Glu Gly Gln Arg His Trp Gln
    130                 135                 140
Trp Val Asp Gln Thr Pro Tyr Asn Glu Ser Ser Thr Phe Trp His Pro
145                 150                 155                 160
Arg Glu Pro Ser Asp Pro Asn Glu Arg Cys Val Val Leu Asn Phe Arg
                165                 170                 175
Lys Ser Pro Lys Arg Trp Gly Trp Asn Asp Val Asn Cys Leu Gly Pro
            180                 185                 190
Gln Arg Ser Val Cys Glu Met Met Lys Ile His Leu
        195                 200
```

```
<210> SEQ ID NO 21
<211> LENGTH: 1185
<212> TYPE: DNA
<213> ORGANISM: Homo sapiens

<400> SEQUENCE: 21
ctgtgattct cactatactg gtcctgagga aagggcttct gtgaactgcg gttttagtt      60
tttattgtgg ttcttagttc tcatgagacc cctcttgagg atatgtgcct atctggtgcc   120
tctgctctcc actagttgag tgaaaggaag gaggtaattt accaccatgt ttggttcctg   180
tttataagat gttttaagaa agatctgaaa cagattttct gaagaaagca gaagctctct   240
tcccattatg acttcggaaa tcacttatgc tgaagtgagg ttcaaaaatg aattcaagtc   300
ctcaggcatc aacacagcct cttctgcagc ttccaaggag aggactgccc ctcacaaaag   360
taataccgga ttccccaagc tgctttgtgc ctcactgttg atattttcc tgctattggc    420
aatctcattc tttattgctt ttgtcaagac agcctggagc tgttgcccaa gaattggaa    480
gtcatttagt tccaactgct actttatttc tactgaatca gcatcttggc aagacagtga   540
gaaggactgt gctagaatgg aggctcacct gctggtgata acactcaag aagagcagga    600
tttcatcttc cagaatctgc aagaagaatc tgcttatttt gtggggctct cagatccaga   660
aggtcagcga cattggcaat gggttgatca gacaccatac aatgaaagtt ccacattctg   720
gcatccacgt gagcccagtg atcccaatga gcgctgcgtt gtgctaaatt ttcgtaaatc   780
acccaaaaga tggggctgga atgatgttaa ttgtcttggt cctcaaaggt cagtttgtga   840
gatgatgaag atccacttat gaactgaaca ttctccatga acaggtggtt ggattggtat   900
ctgtcattgt agggatagat aataagctct tcttattcat gtgtaaggga ggtccataga   960
atttaggtgg tctgtcaact attctactta tgagagaatt ggtctgtaca ttgactgatt  1020
cacttttcca taaagtgagc atttattgag cattttttca tgtgccagag cctgtactgg  1080
aggcccccat tgtgcacaca tggagagaac atgagtctct cttaatttt atctggttgc   1140
taaagaatta tttaccaata aaattatatg atgtggtgtc tcaaa                  1185
```

```
<210> SEQ ID NO 22
<211> LENGTH: 204
<212> TYPE: PRT
<213> ORGANISM: Homo sapiens

<400> SEQUENCE: 22

Met Thr Ser Glu Ile Thr Tyr Ala Glu Val Arg Phe Lys Asn Glu Phe
1               5                   10                  15
Lys Ser Ser Gly Ile Asn Thr Ala Ser Ser Ala Ala Ser Lys Glu Arg
            20                  25                  30
```

```
Thr Ala Pro Leu Lys Ser Asn Thr Gly Phe Pro Lys Leu Leu Cys Ala
            35                  40                  45
Ser Leu Leu Ile Phe Phe Leu Leu Ala Ile Ser Phe Phe Ile Ala
 50                  55                  60
Phe Val Lys Thr Ala Trp Ser Cys Cys Pro Lys Asn Trp Lys Ser Phe
 65                  70                  75                  80
Ser Ser Asn Cys Tyr Phe Ile Ser Thr Glu Ser Ala Ser Trp Gln Asp
                 85                  90                  95
Ser Glu Lys Asp Cys Ala Arg Met Glu Ala His Leu Leu Val Ile Asn
            100                 105                 110
Thr Gln Glu Glu Gln Asp Phe Ile Phe Gln Asn Leu Gln Glu Glu Ser
        115                 120                 125
Ala Tyr Phe Val Gly Leu Ser Asp Pro Glu Gly Gln Arg His Trp Gln
    130                 135                 140
Trp Val Asp Gln Thr Pro Tyr Asn Glu Ser Ser Thr Phe Trp His Pro
145                 150                 155                 160
Arg Glu Pro Ser Asp Pro Asn Glu Arg Cys Val Val Leu Asn Phe Arg
                165                 170                 175
Lys Ser Pro Lys Arg Trp Gly Trp Asn Asp Val Asn Cys Leu Gly Pro
            180                 185                 190
Gln Arg Ser Val Cys Glu Met Met Lys Ile His Leu
        195                 200

<210> SEQ ID NO 23
<211> LENGTH: 1428
<212> TYPE: DNA
<213> ORGANISM: Homo sapiens

<400> SEQUENCE: 23
cttcaggtca gggagaatgt ataaatgtcc attgccatcg aggttctgct attttttgaga      60
agctgaagca actccaagga cacagttcac agaaatttgg ttctcagccc caaaatactg     120
attgaattgg agacaattac aaggactctc tggccaaaaa cccttgaaga ggccccgtga     180
aggaggcagt gaggagcttt tgattgctga cctgtgtcgt accaccccag aatgtgcact     240
gggggctgtg ccagatgcct gggggggacc ctcattcccc ttgcttttt tggcttcctg     300
gctaacatcc tgttattttt tcctggagga aaagtgatag atgacaacga ccacctttcc     360
caagagatct ggttttcgg aggaatatta ggaagcggtg tcttgatgat cttccctgcg     420
ctggtgttct tgggcctgaa gaacaatgac tgctgtgggt gctgcggcaa cgagggctgt     480
gggaagcgat ttgcgatgtt cacctccacg atatttgctg tggttggatt cttgggagct     540
ggatactcgt ttatcatctc agccatttca atcaacaagg gtcctaaatg cctcatggcc     600
aatagtacat ggggctaccc cttccacgac ggggattatc tcaatgatga ggccttatgg     660
aacaagtgcc gagagcctct caatgtggtt ccctggaatc tgaccctctt ctccatcctg     720
ctggtcgtag aggaatccca gatggttctc tgcgccatcc aggtggtcaa tggcctcctg     780
gggacccctct gtgggactg ccagtgttgt ggctgctgtg gggagatggg acccgtttaa     840
acctccgaga tgagctgctc agactctaca gcatgacgac tacaatttct tttcataaaa     900
cttcttctct tcttggaatt attaattcct atctgcttcc tagctgataa agcttagaaa     960
aggcagttat tccttctttc caaccagctt tgctcgagtt agaattttgt tattttcaaa    1020
taaaaaatag tttggccact taacaaattt gattataaaa tctttcaaat tagttccttt    1080
ttagaattta ccaacaggtt caaagcatac ttttcatgat tttttattat caaatgtaaa    1140
```

-continued

```
atgtataaag tcacatgtac tgccatacta cttctttgta tataaagatg tttatatctt    1200
tggaagtttt acataaatca aaggaagaaa gcacatttaa aatgagaaac taagaccaat    1260
ttctgttttt aagaggaaaa agaatgattg atgtatccta agtattgtta tttgttgtct    1320 tttttgctg ccttgcttga gttgcttgtg actgatcttt tgaggctgtc atcatggcta     1380
gggttctttt atgtatgtta aattaaaacc tgaattcaga ggtaacgt                 1428
```

<210> SEQ ID NO 24
<211> LENGTH: 202
<212> TYPE: PRT
<213> ORGANISM: Homo sapiens

<400> SEQUENCE: 24

```
Met Cys Thr Gly Gly Cys Ala Arg Cys Leu Gly Gly Thr Leu Ile Pro
1               5                   10                  15
Leu Ala Phe Phe Gly Phe Leu Ala Asn Ile Leu Leu Phe Phe Pro Gly
            20                  25                  30
Gly Lys Val Ile Asp Asp Asn Asp His Leu Ser Gln Glu Ile Trp Phe
        35                  40                  45
Phe Gly Gly Ile Leu Gly Ser Gly Val Leu Met Ile Phe Pro Ala Leu
    50                  55                  60
Val Phe Leu Gly Leu Lys Asn Asn Asp Cys Cys Gly Cys Cys Gly Asn
65                  70                  75                  80
Glu Gly Cys Gly Lys Arg Phe Ala Met Phe Thr Ser Thr Ile Phe Ala
                85                  90                  95
Val Val Gly Phe Leu Gly Ala Gly Tyr Ser Phe Ile Ile Ser Ala Ile
            100                 105                 110
Ser Ile Asn Lys Gly Pro Lys Cys Leu Met Ala Asn Ser Thr Trp Gly
        115                 120                 125
Tyr Pro Phe His Asp Gly Asp Tyr Leu Asn Asp Glu Ala Leu Trp Asn
    130                 135                 140
Lys Cys Arg Glu Pro Leu Asn Val Val Pro Trp Asn Leu Thr Leu Phe
145                 150                 155                 160
Ser Ile Leu Leu Val Val Gly Gly Ile Gln Met Val Leu Cys Ala Ile
                165                 170                 175
Gln Val Val Asn Gly Leu Leu Gly Thr Leu Cys Gly Asp Cys Gln Cys
            180                 185                 190
Cys Gly Cys Cys Gly Gly Asp Gly Pro Val
        195                 200
```

<210> SEQ ID NO 25
<211> LENGTH: 1285
<212> TYPE: DNA
<213> ORGANISM: Homo sapiens

<400> SEQUENCE: 25

```
ggggcccagg gccctcctat ggaccctgcc cgctcccctc ccattgtcca cggctgtccg     60 cccacccca ttctccaagc ttcagccccc tccttagttc ggcatctgca cagcactgaa     120
gaacctggga atcagaccct gagaccctga gcaatcccag gtccagcgcc agccctatca    180
tgaccaagga gtatcaagac cttcagcatc tggacaatga ggagagtgac caccatcagc    240
tcagaaaagg gccacctcct ccccagcccc tcctgcagcg tctctgctcc ggacctcgcc    300
tcctcctgct ctccctgggc tcagcctcc tgctgcttgt ggttgtctgt gtgatcggat     360 cccaaaaactc ccagctgcag gaggagctgc ggggcctgag agagacgttc agcaacttca    420
```

-continued

```
cagcgagcac ggaggcccag gtcaagggct tgagcaccca gggaggcaat gtgggaagaa      480
agatgaagtc gctagagtcc cagctggaga acagcagaa  ggacctgagt gaagatcact      540
ccagcctgct gctccacgtg aagcagttcg tgtctgacct gcggagcctg agctgtcaga      600
tggcggcgct ccagggcaat ggctcagaaa ggacctgctg cccggtcaac tgggtggagc      660
acgagcgcag ctgctactgg ttctctcgct ccgggaaggc ctgggctgac gccgacaact      720
actgccggct ggaggacgcg cacctggtgg tggtcacgtc ctgggaggag cagaaatttg      780
tccagcacca cataggccct gtgaacacct ggatgggcct ccacgaccaa aacgggccct      840
ggaagtgggt ggacgggacg gactacgaga cgggcttcaa gaactggagg ccggagcagc      900
cggacgactg gtacgccac  gggctcggag gaggcgagga ctgtgcccac ttcaccgacg      960
acggccgctg gaacgacgac gtctgccaga ggccctaccg ctgggtctgc gagacagagc     1020
tggacaaggc cagccaggag ccacctctcc tttaatttat ttcttcaatg cctcgacctg     1080 ccgcagggt  ccgggattgg gaatccgccc atctgggggc ctcttctgct ttctcgggaa     1140
ttttcatcta ggattttaag ggaagggaa  ggatagggtg atgttccgaa ggtgaggagc     1200
ttgaaacccg tggcgctttc tgcagtttgc aggttatcat tgtgaacttt ttttttttt      1260 aagagtaaaa agaaatatac ctaaa                                           1285
```

```
<210> SEQ ID NO 26
<211> LENGTH: 291
<212> TYPE: PRT
<213> ORGANISM: Homo sapiens

<400> SEQUENCE: 26
```

```
Met Thr Lys Glu Tyr Gln Asp Leu Gln His Leu Asp Asn Glu Glu Ser
1               5                   10                  15

Asp His His Gln Leu Arg Lys Gly Pro Pro Pro Gln Pro Leu Leu
            20                  25                  30

Gln Arg Leu Cys Ser Gly Pro Arg Leu Leu Leu Ser Leu Gly Leu
        35                  40                  45

Ser Leu Leu Leu Leu Val Val Val Cys Val Ile Gly Ser Gln Asn Ser
    50                  55                  60

Gln Leu Gln Glu Glu Leu Arg Gly Leu Arg Glu Thr Phe Ser Asn Phe
65                  70                  75                  80

Thr Ala Ser Thr Glu Ala Gln Val Lys Gly Leu Ser Thr Gln Gly Gly
                85                  90                  95

Asn Val Gly Arg Lys Met Lys Ser Leu Glu Ser Gln Leu Glu Lys Gln
            100                 105                 110

Gln Lys Asp Leu Ser Glu Asp His Ser Ser Leu Leu Leu His Val Lys
        115                 120                 125

Gln Phe Val Ser Asp Leu Arg Ser Leu Ser Cys Gln Met Ala Ala Leu
    130                 135                 140

Gln Gly Asn Gly Ser Glu Arg Thr Cys Cys Pro Val Asn Trp Val Glu
145                 150                 155                 160

His Glu Arg Ser Cys Tyr Trp Phe Ser Arg Ser Gly Lys Ala Trp Ala
                165                 170                 175

Asp Ala Asp Asn Tyr Cys Arg Leu Glu Asp Ala His Leu Val Val Val
            180                 185                 190

Thr Ser Trp Glu Glu Gln Lys Phe Val Gln His His Ile Gly Pro Val
        195                 200                 205

Asn Thr Trp Met Gly Leu His Asp Gln Asn Gly Pro Trp Lys Trp Val
```

```
                210                 215                 220
Asp Gly Thr Asp Tyr Glu Thr Gly Phe Lys Asn Trp Arg Pro Glu Gln
225                 230                 235                 240

Pro Asp Asp Trp Tyr Gly His Gly Leu Gly Gly Gly Glu Asp Cys Ala
                245                 250                 255

His Phe Thr Asp Asp Gly Arg Trp Asn Asp Asp Val Cys Gln Arg Pro
            260                 265                 270

Tyr Arg Trp Val Cys Glu Thr Glu Leu Asp Lys Ala Ser Gln Glu Pro
        275                 280                 285

Pro Leu Leu
    290

<210> SEQ ID NO 27
<211> LENGTH: 5330
<212> TYPE: DNA
<213> ORGANISM: Homo sapiens

<400> SEQUENCE: 27 agtattttg gagaagttag taaaaccgaa tctgacatca tcacctagca gttcatgcag      60
ctagcaagtg gtttgttctt agggtaacag aggaggaaat tgttcctcgt ctgataagac    120
aacagtggag aaaggacgca tgctgtttct tagggacacg gctgacttcc agatatgacc    180
atgtatttgt ggcttaaact cttggcattt ggctttgcct ttctggacac agaagtattt    240
gtgacagggc aaagcccaac accttccccc actggattga ctacagcaaa gatgcccagt    300
gttccacttt caagtgaccc cttacctact cacaccactg cattctcacc cgcaagcacc    360
tttgaaagag aaaatgactt ctcagagacc acaacttctc ttagtccaga caatacttcc    420
acccaagtat ccccggactc tttggataat gctagtgctt taataccac aggtgtttca    480 tcagtacaga cgcctcacct tcccacgcac gcagactcgc agacgccctc tgctggaact    540
gacacgcaga cattcagcgg ctccgccgcc aatgcaaaac tcaaccctac cccaggcagc    600
aatgctatct cagatgtccc aggagagagg agtacagcca gcctttcc tacagaccca    660 gtttccccat tgacaaccac cctcagcctt gcacaccaca gctctgctgc cttacctgca    720
cgcacctcca acaccaccat cacagcgaac acctcagatg cctaccttaa tgcctctgaa    780
acaaccactc tgagcccttc tggaagcgct gtcatttcaa ccacaacaat agctactact    840
ccatctaagc aacatgtga tgaaaaatat gcaaacatca ctgtggatta cttatataac    900
aaggaaacta attatttac agcaaagcta aatgttaatg agaatgtgga atgtggaaac    960 atacttgca caaacaatga ggtgcataac cttacagaat gtaaaaatgc gtctgtttcc    1020
atatctcata attcatgtac tgctcctgat aagacattaa tattagatgt gccaccaggg    1080
gttgaaaagt ttcagttaca tgattgtaca caagttgaaa aagcagatac tactattgt    1140 ttaaaatgga aaatattga aacctttact tgtgatacac agaatattac ctacagattt    1200
cagtgtggta atatgatatt tgataataaa gaattaaat tagaaaaccct tgaacccgaa    1260 catgagtata gtgtgactc agaaatactc tataataacc acaagtttac taacgcaagt    1320
aaaattatta aacagattt tgggagtcca ggagagcctc agattatttt ttgtagaagt    1380
gaagctgcac atcaaggagt aattacctgg aatccccctc aaagatcatt tcataatttt    1440
accctctgtt atataaaaga gacagaaaaa gattgcctca atctggataa aaacctgatc    1500
aaatatgatt tgcaaaattt aaaacctttat acgaaatatg tttatatcatt acatgcctac   1560 atcattgcaa aagtgcaacg taatggaagt gctgcaatgt gtcatttcac aactaaaagt    1620
```

```
gctcctccaa gccaggtctg gaacatgact gtctccatga catcagataa tagtatgcat    1680
gtcaagtgta ggcctcccag ggaccgtaat ggcccccatg aacgttacca tttggaagtt    1740
gaagctggaa atactctggt tagaaatgag tcgcataaga attgcgattt ccgtgtaaaa    1800
gatcttcaat attcaacaga ctacactttt aaggcctatt tcacaatgg agactatcct     1860 ggagaaccct ttattttaca tcattcaaca tcttataatt ctaaggcact gatagcattt    1920
ctggcatttc tgattattgt gacatcaata gccctgcttg ttgttctcta caaaatctat    1980
gatctacata agaaaagatc ctgcaattta gatgaacagc aggagcttgt tgaaagggat    2040
gatgaaaaac aactgatgaa tgtggagcca atccatgcag atattttgtt ggaaacttat    2100
aagaggaaga ttgctgatga aggaagactt tttctggctg aatttcagag catcccgcgg    2160
gtgttcagca agtttcctat aaaggaagct cgaaagccct taaccagaa taaaaaccgt     2220 tatgttgaca ttcttcctta tgattataac cgtgttgaac tctctgagat aaacggagat    2280
gcagggtcaa actacataaa tgccagctat attgatggtt tcaaagaacc caggaaatac    2340
attgctgcac aaggtcccag ggatgaaact gttgatgatt tctggaggat gatttgggaa    2400
cagaaagcca cagttattgt catggtcact cgatgtgaag aaggaaacag gaacaagtgt    2460
gcagaatact ggccgtcaat ggaagagggc actcgggctt ttggagatgt tgttgtaaag    2520
atcaaccagc acaaaagatg tccagattac atcattcaga aattgaacat tgtaaataaa    2580
aaagaaaaag caactggaag agaggtgact cacattcagt tcaccagctg ccagaccac    2640 ggggtgcctg aggatcctca cttgctcctc aaactgagaa ggagagtgaa tgccttcagc    2700
aatttcttca gtggtcccat tgtggtgcac tgcagtgctg tgttgggcg cacaggaacc     2760 tatatcggaa ttgatgccat gctagaaggc ctggaagccg agaacaaagt ggatgtttat    2820
ggttatgttg tcaagctaag gcgacagaga tgcctgatgg ttcaagtaga ggcccagtac    2880
atcttgatcc atcaggcttt ggtggaatac aatcagtttg gagaaacaga agtgaatttg    2940
tctgaattac atccatatct acataacatg aagaaaggg atccacccag tgagccgtct    3000
ccactagagg ctgaattcca gagacttcct tcatatagga gctggaggac acagcacatt    3060
ggaaatcaag aagaaaataa aagtaaaaac aggaattcta atgtcatccc atatgactat    3120
aacagagtgc cacttaaaca tgagctggaa atgagtaaag agagtgagca tgattcagat    3180
gaatcctctg atgatgacag tgattcagag gaaccaagca aatacatcaa tgcatctttt    3240
ataatgagct actggaaacc tgaagtgatg attgctgctc agggaccact gaaggagacc    3300
attggtgact tttggcagat gatcttccaa agaaagtca aagttattgt tatgctgaca    3360
gaactgaaac atggagacca ggaaatctgt gctcagtact ggggagaagg aaagcaaaca    3420 tatgagata ttgaagttga cctgaaagac acagacaaat cttcaactta tacccttcgt    3480
gtctttgaac tgagacattc caagaggaaa gactctcgaa ctgtgtacca gtaccaatat    3540
acaaactgga gtgtggagca gcttcctgca gaacccaagg aattaatctc tatgattcag    3600
gtcgtcaaac aaaaacttcc ccagaagaat tcctctgaag ggaacaagca tcacaagagt    3660
acacctctac tcattcactg cagggatgga tctcagcaaa cgggaatatt ttgtgctttg    3720
ttaaatctct tagaaagtgc ggaaacagaa gaggtagtgg atatttttca agtggtaaaa    3780
gctctacgca aagctaggcc aggcatggtt tccacattcg agcaatatca attcctatat    3840
gacgtcattg ccagcaccta ccctgctcag aatggacaag taaagaaaaa caaccatcaa    3900
gaagataaaa ttgaatttga taatgaagtg acaaagtaa agcaggatgc taattgtgtt    3960
aatccacttg gtgccccaga aaagctccct gaagcaaagg aacaggctga aggttctgaa    4020
```

```
cccacgagtg gcactgaggg gccagaacat tctgtcaatg gtcctgcaag tccagcttta    4080
aatcaaggtt cataggaaaa gacataaatg aggaaactcc aaacctcctg ttagctgtta    4140
tttctatttt tgtagaagta ggaagtgaaa ataggtatac agtggattaa ttaaatgcag    4200
cgaaccaata tttgtagaag ggttatattt tactactgtg gaaaatatt taagatagtt    4260 ttgccagaac agtttgtaca gacgtatgct tattttaaaa ttttatctct tattcagtaa    4320
aaaacaactt ctttgtaatc gttatgtgtg tatatgtatg tgtgtatggg tgtgtgtttg    4380
tgtgagagac agagaaagag agagaattct ttcaagtgaa tctaaaagct tttgcttttc    4440
ctttgttttt atgaagaaaa aatacatttt atattagaag tgttaactta gcttgaagga    4500
tctgttttta aaaatcataa actgtgtgca gactcaataa aatcatgtac atttctgaaa    4560
tgacctcaag atgtcctcct tgttctactc atatatatct atcttatata gtttactatt    4620
ttacttctag agatagtaca taaaggtggt atgtgtgtgt atgctactac aaaaaagttg    4680
ttaactaaat taacattggg aaatcttata ttccatatat tagcatttag tccaatgtct    4740
ttttaagctt atttaattaa aaaatttcca gtgagcttat catgctgtct ttacatgggg    4800
ttttcaattt tgcatgctcg attattccct gtacaatatt taaaatttat tgcttgatac    4860
ttttgacaac aaattaggtt ttgtacaatt gaacttaaat aaatgtcatt aaaataaata    4920
aatgcaatat gtattaatat tcattgtata aaaatagaag aatacaaaca tatttgttaa    4980
atatttacat atgaaattta atatagctat ttttatggaa ttttttcattg atatgaaaaa    5040 tatgatattg catatgcata gttcccatgt taaatcccat tcataacttt cattaaagca    5100
tttactttga atttctccaa tgcttagaat gttttttacca ggaatggatg tcgctaatca    5160
taataaaatt caaccattat tttttttcttg tttataaac attgtgttat atgttcaaat    5220
atgaaatgtg tatgcaccta ttgaaatatg tttaatgcat ttattaacat ttgcaggaca    5280
cttttacagg ccccaattat ccaatagtct aataattgtt taagatctag    5330
```

<210> SEQ ID NO 28
<211> LENGTH: 1304
<212> TYPE: PRT
<213> ORGANISM: Homo sapiens

<400> SEQUENCE: 28

| | | | | | | | | | | | | | | |
|---|---|---|---|---|---|---|---|---|---|---|---|---|---|---|
| Met | Tyr | Leu | Trp | Leu | Lys | Leu | Leu | Ala | Phe | Gly | Phe | Ala | Phe | Leu | Asp |
| 1 | | | | 5 | | | | | 10 | | | | | 15 | |
| Thr | Glu | Val | Phe | Val | Thr | Gly | Gln | Ser | Pro | Thr | Pro | Ser | Pro | Thr | Gly |
| | | | 20 | | | | | 25 | | | | | 30 | | |
| Leu | Thr | Thr | Ala | Lys | Met | Pro | Ser | Val | Pro | Leu | Ser | Ser | Asp | Pro | Leu |
| | | | 35 | | | | | 40 | | | | | 45 | | |
| Pro | Thr | His | Thr | Thr | Ala | Phe | Ser | Pro | Ala | Ser | Thr | Phe | Glu | Arg | Glu |
| | | | 50 | | | | | 55 | | | | | 60 | | |
| Asn | Asp | Phe | Ser | Glu | Thr | Thr | Thr | Ser | Leu | Ser | Pro | Asp | Asn | Thr | Ser |
| 65 | | | | | 70 | | | | | 75 | | | | | 80 |
| Thr | Gln | Val | Ser | Pro | Asp | Ser | Leu | Asp | Asn | Ala | Ser | Ala | Phe | Asn | Thr |
| | | | | 85 | | | | | 90 | | | | | 95 | |
| Thr | Gly | Val | Ser | Ser | Val | Gln | Thr | Pro | His | Leu | Pro | Thr | His | Ala | Asp |
| | | | | 100 | | | | | 105 | | | | | 110 | |
| Ser | Gln | Thr | Pro | Ser | Ala | Gly | Thr | Asp | Thr | Gln | Thr | Phe | Ser | Gly | Ser |
| | | | 115 | | | | | 120 | | | | | 125 | | |
| Ala | Ala | Asn | Ala | Lys | Leu | Asn | Pro | Thr | Pro | Gly | Ser | Asn | Ala | Ile | Ser |
| | | 130 | | | | | 135 | | | | | 140 | | | |

-continued

```
Asp Val Pro Gly Glu Arg Ser Thr Ala Ser Thr Phe Pro Thr Asp Pro
145                 150                 155                 160

Val Ser Pro Leu Thr Thr Thr Leu Ser Leu Ala His His Ser Ser Ala
            165                 170                 175

Ala Leu Pro Ala Arg Thr Ser Asn Thr Thr Ile Thr Ala Asn Thr Ser
        180                 185                 190

Asp Ala Tyr Leu Asn Ala Ser Glu Thr Thr Thr Leu Ser Pro Ser Gly
            195                 200                 205

Ser Ala Val Ile Ser Thr Thr Thr Ile Ala Thr Thr Pro Ser Lys Pro
210                 215                 220

Thr Cys Asp Glu Lys Tyr Ala Asn Ile Thr Val Asp Tyr Leu Tyr Asn
225                 230                 235                 240

Lys Glu Thr Lys Leu Phe Thr Ala Lys Leu Asn Val Asn Glu Asn Val
                245                 250                 255

Glu Cys Gly Asn Asn Thr Cys Thr Asn Asn Glu Val His Asn Leu Thr
                260                 265                 270

Glu Cys Lys Asn Ala Ser Val Ser Ile Ser His Asn Ser Cys Thr Ala
            275                 280                 285

Pro Asp Lys Thr Leu Ile Leu Asp Val Pro Pro Gly Val Glu Lys Phe
        290                 295                 300

Gln Leu His Asp Cys Thr Gln Val Glu Lys Ala Asp Thr Thr Ile Cys
305                 310                 315                 320

Leu Lys Trp Lys Asn Ile Glu Thr Phe Thr Cys Asp Thr Gln Asn Ile
                325                 330                 335

Thr Tyr Arg Phe Gln Cys Gly Asn Met Ile Phe Asp Asn Lys Glu Ile
            340                 345                 350

Lys Leu Glu Asn Leu Glu Pro Glu His Glu Tyr Lys Cys Asp Ser Glu
        355                 360                 365

Ile Leu Tyr Asn Asn His Lys Phe Thr Asn Ala Ser Lys Ile Ile Lys
    370                 375                 380

Thr Asp Phe Gly Ser Pro Gly Glu Pro Gln Ile Ile Phe Cys Arg Ser
385                 390                 395                 400

Glu Ala Ala His Gln Gly Val Ile Thr Trp Asn Pro Pro Gln Arg Ser
                405                 410                 415

Phe His Asn Phe Thr Leu Cys Tyr Ile Lys Glu Thr Glu Lys Asp Cys
            420                 425                 430

Leu Asn Leu Asp Lys Asn Leu Ile Lys Tyr Asp Leu Gln Asn Leu Lys
        435                 440                 445

Pro Tyr Thr Lys Tyr Val Leu Ser Leu His Ala Tyr Ile Ile Ala Lys
    450                 455                 460

Val Gln Arg Asn Gly Ser Ala Ala Met Cys His Phe Thr Thr Lys Ser
465                 470                 475                 480

Ala Pro Pro Ser Gln Val Trp Asn Met Thr Val Ser Met Thr Ser Asp
                485                 490                 495

Asn Ser Met His Val Lys Cys Arg Pro Pro Arg Asp Arg Asn Gly Pro
            500                 505                 510

His Glu Arg Tyr His Leu Glu Val Glu Ala Gly Asn Thr Leu Val Arg
        515                 520                 525

Asn Glu Ser His Lys Asn Cys Asp Phe Arg Val Lys Asp Leu Gln Tyr
    530                 535                 540

Ser Thr Asp Tyr Thr Phe Lys Ala Tyr Phe His Asn Gly Asp Tyr Pro
545                 550                 555                 560
```

-continued

```
Gly Glu Pro Phe Ile Leu His His Ser Thr Ser Tyr Asn Ser Lys Ala
            565                 570                 575
Leu Ile Ala Phe Leu Ala Phe Leu Ile Ile Val Thr Ser Ile Ala Leu
        580                 585                 590
Leu Val Val Leu Tyr Lys Ile Tyr Asp Leu His Lys Lys Arg Ser Cys
    595                 600                 605
Asn Leu Asp Glu Gln Gln Leu Val Glu Arg Asp Asp Glu Lys Gln
610                 615                 620
Leu Met Asn Val Glu Pro Ile His Ala Asp Ile Leu Leu Glu Thr Tyr
625                 630                 635                 640
Lys Arg Lys Ile Ala Asp Glu Gly Arg Leu Phe Leu Ala Glu Phe Gln
                645                 650                 655
Ser Ile Pro Arg Val Phe Ser Lys Phe Pro Ile Lys Glu Ala Arg Lys
            660                 665                 670
Pro Phe Asn Gln Asn Lys Asn Arg Tyr Val Asp Ile Leu Pro Tyr Asp
        675                 680                 685
Tyr Asn Arg Val Glu Leu Ser Glu Ile Asn Gly Asp Ala Gly Ser Asn
    690                 695                 700
Tyr Ile Asn Ala Ser Tyr Ile Asp Gly Phe Lys Glu Pro Arg Lys Tyr
705                 710                 715                 720
Ile Ala Ala Gln Gly Pro Arg Asp Glu Thr Val Asp Asp Phe Trp Arg
                725                 730                 735
Met Ile Trp Glu Gln Lys Ala Thr Val Ile Val Met Val Thr Arg Cys
            740                 745                 750
Glu Glu Gly Asn Arg Asn Lys Cys Ala Glu Tyr Trp Pro Ser Met Glu
        755                 760                 765
Glu Gly Thr Arg Ala Phe Gly Asp Val Val Lys Ile Asn Gln His
    770                 775                 780
Lys Arg Cys Pro Asp Tyr Ile Ile Gln Lys Leu Asn Ile Val Asn Lys
785                 790                 795                 800
Lys Glu Lys Ala Thr Gly Arg Glu Val Thr His Ile Gln Phe Thr Ser
                805                 810                 815
Trp Pro Asp His Gly Val Pro Glu Asp Pro His Leu Leu Leu Lys Leu
            820                 825                 830
Arg Arg Arg Val Asn Ala Phe Ser Asn Phe Phe Ser Gly Pro Ile Val
        835                 840                 845
Val His Cys Ser Ala Gly Val Gly Arg Thr Gly Thr Tyr Ile Gly Ile
    850                 855                 860
Asp Ala Met Leu Glu Gly Leu Glu Ala Glu Asn Lys Val Asp Val Tyr
865                 870                 875                 880
Gly Tyr Val Val Lys Leu Arg Arg Gln Arg Cys Leu Met Val Gln Val
                885                 890                 895
Glu Ala Gln Tyr Ile Leu Ile His Gln Ala Leu Val Glu Tyr Asn Gln
            900                 905                 910
Phe Gly Glu Thr Glu Val Asn Leu Ser Glu Leu His Pro Tyr Leu His
        915                 920                 925
Asn Met Lys Lys Arg Asp Pro Pro Ser Glu Pro Ser Pro Leu Glu Ala
    930                 935                 940
Glu Phe Gln Arg Leu Pro Ser Tyr Arg Ser Trp Arg Thr Gln His Ile
945                 950                 955                 960
Gly Asn Gln Glu Glu Asn Lys Ser Lys Asn Arg Asn Ser Asn Val Ile
                965                 970                 975
Pro Tyr Asp Tyr Asn Arg Val Pro Leu Lys His Glu Leu Glu Met Ser
```

|     |     |     |     |     |     |     | 980 |     |     |     |     | 985 |     |     |     |     | 990 |     |
| --- | --- | --- | --- | --- | --- | --- | --- | --- | --- | --- | --- | --- | --- | --- | --- | --- | --- | --- |

Lys Glu Ser Glu His Asp Ser Asp Glu Ser Ser Asp Asp Ser Asp
               995                      1000                    1005

Ser Glu Glu Pro Ser Lys Tyr Ile Asn Ala Ser Phe Ile Met Ser
   1010                      1015                    1020

Tyr Trp Lys Pro Glu Val Met Ile Ala Ala Gln Gly Pro Leu Lys
   1025                      1030                    1035

Glu Thr Ile Gly Asp Phe Trp Gln Met Ile Phe Gln Arg Lys Val
   1040                      1045                    1050

Lys Val Ile Val Met Leu Thr Glu Leu Lys His Gly Asp Gln Glu
   1055                      1060                    1065

Ile Cys Ala Gln Tyr Trp Gly Glu Gly Lys Gln Thr Tyr Gly Asp
   1070                      1075                    1080

Ile Glu Val Asp Leu Lys Asp Thr Asp Lys Ser Ser Thr Tyr Thr
   1085                      1090                    1095

Leu Arg Val Phe Glu Leu Arg His Ser Lys Arg Lys Asp Ser Arg
   1100                      1105                    1110

Thr Val Tyr Gln Tyr Gln Tyr Thr Asn Trp Ser Val Glu Gln Leu
   1115                      1120                    1125

Pro Ala Glu Pro Lys Glu Leu Ile Ser Met Ile Gln Val Val Lys
   1130                      1135                    1140

Gln Lys Leu Pro Gln Lys Asn Ser Ser Glu Gly Asn Lys His His
   1145                      1150                    1155

Lys Ser Thr Pro Leu Leu Ile His Cys Arg Asp Gly Ser Gln Gln
   1160                      1165                    1170

Thr Gly Ile Phe Cys Ala Leu Leu Asn Leu Leu Glu Ser Ala Glu
   1175                      1180                    1185

Thr Glu Glu Val Val Asp Ile Phe Gln Val Val Lys Ala Leu Arg
   1190                      1195                    1200

Lys Ala Arg Pro Gly Met Val Ser Thr Phe Glu Gln Tyr Gln Phe
   1205                      1210                    1215

Leu Tyr Asp Val Ile Ala Ser Thr Tyr Pro Ala Gln Asn Gly Gln
   1220                      1225                    1230

Val Lys Lys Asn Asn His Gln Glu Asp Lys Ile Glu Phe Asp Asn
   1235                      1240                    1245

Glu Val Asp Lys Val Lys Gln Asp Ala Asn Cys Val Asn Pro Leu
   1250                      1255                    1260

Gly Ala Pro Glu Lys Leu Pro Glu Ala Lys Glu Gln Ala Glu Gly
   1265                      1270                    1275

Ser Glu Pro Thr Ser Gly Thr Glu Gly Pro Glu His Ser Val Asn
   1280                      1285                    1290

Gly Pro Ala Ser Pro Ala Leu Asn Gln Gly Ser
   1295                      1300

<210> SEQ ID NO 29
<211> LENGTH: 4847
<212> TYPE: DNA
<213> ORGANISM: Homo sapiens

<400> SEQUENCE: 29

```
agtattttg gagaagttag taaaaccgaa tctgacatca tcacctagca gttcatgcag      60
ctagcaagtg gtttgttctt agggtaacag aggaggaaat gttcctcgt ctgataagac     120 aacagtggag aaaggacgca tgctgtttct tagggacacg gctgacttcc agatatgacc    180
```

```
atgtatttgt ggcttaaact cttggcattt ggctttgcct ttctggacac agaagtattt      240
gtgacagggc aaagcccaac accttccccc actgatgcct accttaatgc ctctgaaaca      300
accactctga gcccttctgg aagcgctgtc atttcaacca caacaatagc tactactcca      360
tctaagccaa catgtgatga aaatatgca acatcactg tggattactt atataacaag        420
gaaactaaat tatttacagc aaagctaaat gttaatgaga atgtggaatg tggaaacaat      480
acttgcacaa acaatgaggt gcataacctt acagaatgta aaaatgcgtc tgtttccata      540
tctcataatt catgtactgc tcctgataag acattaatat tagatgtgcc accaggggtt      600
gaaaagtttc agttacatga ttgtacacaa gttgaaaaag cagatactac tatttgttta      660
aaatggaaaa atattgaaac ctttacttgt gatacacaga atattaccta cagatttcag      720
tgtggtaata tgatatttga taataaagaa attaaattag aaaaccttga acccgaacat      780
gagtataagt gtgactcaga atactctat aataaccaca gtttactaa cgcaagtaaa        840 attattaaaa cagattttgg gagtccagga gagcctcaga ttattttttg tagaagtgaa      900
gctgcacatc aaggagtaat tacctggaat ccccctcaaa gatcatttca taattttacc      960
ctctgttata taaagagac agaaaaagat tgcctcaatc tggataaaaa cctgatcaaa      1020
tatgatttgc aaaatttaaa accttatacg aaatatgttt tatcattaca tgcctacatc     1080
attgcaaaag tgcaacgtaa tggaagtgct gcaatgtgtc atttcacaac taaaagtgct     1140
cctccaagcc aggtctggaa catgactgtc tccatgacat cagataatag tatgcatgtc     1200
aagtgtaggc ctcccaggga ccgtaatggc ccccatgaac gttaccattt ggaagttgaa     1260
gctggaaata ctctggttag aaatgagtcg cataagaatt gcgatttccg tgtaaaagat     1320
cttcaatatt caacagacta cacttttaag gcctattttc acaatggaga ctatcctgga     1380
gaacccttta ttttacatca ttcaacatct tataattcta aggcactgat agcatttctg     1440
gcatttctga ttattgtgac atcaatagcc ctgcttgttg ttctctacaa aatctatgat     1500
ctacataaga aaagatcctg caatttagat gaacagcagg agcttgttga agggatgat     1560 gaaaaacaac tgatgaatgt ggagccaatc catgcagata ttttgttgga aacttataag     1620
aggaagattg ctgatgaagg aagactttt ctggctgaat tcagagcat cccgcgggtg      1680 ttcagcaagt ttcctataaa ggaagctcga aagcccttta accagaataa aaaccgttat     1740
gttgacattc ttccttatga ttataaccgt gttgaactct ctgagataaa cggagatgca     1800
gggtcaaact acataaatgc cagctatatt gatggtttca aagaacccag gaaatacatt     1860
gctgcacaag gtcccaggga tgaaactgtt gatgattct ggaggatgat ttgggaacag      1920
aaagccacag ttattgtcat ggtcactcga tgtgaagaag aaacaggaa caagtgtgca     1980 gaatactggc cgtcaatgga agagggcact cgggcttttg gagatgttgt tgtaaagatc     2040
aaccagcaca aaagatgtcc agattacatc attcagaaat tgaacattgt aaataaaaaa     2100
gaaaaagcaa ctgaagagaa ggtgactcac attcagttca ccagctggcc agaccacggg     2160
gtgcctgagg atcctcactt gctcctcaaa ctgagaagga gagtgaatgc cttcagcaat     2220
ttcttcagtg gtcccattgt ggtgcactgc agtgctggtg ttgggcgcac aggaacctat     2280
atcggaattg atgccatgct agaaggcctg gaagccgaga acaaagtgga tgtttatggt     2340
tatgttgtca agctaaggcg acagagatgc ctgatggttc aagtagaggc ccagtacatc     2400
ttgatccatc aggctttggt ggaatacaat cagtttggag aaacagaagt gaatttgtct     2460
gaattacatc catatctaca taacatgaag aaaagggatc cacccagtga gccgtctcca     2520
ctagaggctg aattccagag acttcccttca tataggagct ggaggacaca gcacattgga     2580
```

```
aatcaagaag aaaataaaag taaaaacagg aattctaatg tcatcccata tgactataac    2640
agagtgccac ttaaacatga gctggaaatg agtaaagaga gtgagcatga ttcagatgaa    2700
tcctctgatg atgacagtga ttcagaggaa ccaagcaaat acatcaatgc atcttttata    2760
atgagctact ggaaacctga agtgatgatt gctgctcagg gaccactgaa ggagaccatt    2820
ggtgactttt ggcagatgat cttccaaaga aaagtcaaag ttattgttat gctgacagaa    2880
ctgaaacatg agaccagga atctgtgct cagtactggg gagaaggaaa gcaaacatat     2940
ggagatattg aagttgacct gaaagacaca gacaaatctt caacttatac ccttcgtgtc    3000
tttgaactga acattccaa gaggaaagac tctcgaactg tgtaccagta ccaatataca    3060
aactggagtg tggagcagct tcctgcagaa cccaaggaat taatctctat gattcaggtc    3120
gtcaaacaaa aacttcccca gaagaattcc tctgaaggga caagcatca aagagtaca     3180
cctctactca ttcactgcag ggatggatct cagcaaacgg gaatattttg tgctttgtta    3240
aatctcttag aaagtgcgga aacagaagag gtagtggata ttttttcaagt ggtaaaagct   3300
ctacgcaaag ctaggccagg catggttccc acattcgagc aatatcaatt cctatatgac    3360
gtcattgcca gcacctaccc tgctcagaat ggacaagtaa agaaaaacaa ccatcaagaa    3420
gataaaattg aatttgataa tgaagtggac aaagtaaagc aggatgctaa ttgtgttaat    3480
ccacttggtg ccccagaaaa gctccctgaa gcaaaggaac aggctgaagg ttctgaaccc    3540
acgagtggca ctgaggggcc agaacattct gtcaatggtc ctgcaagtcc agctttaaat    3600
caaggttcat aggaaaagac ataaatgagg aaactccaaa cctcctgtta gctgttattt    3660
ctatttttgt agaagtagga agtgaaaata ggtatacagt ggattaatta aatgcagcga    3720
accaatattt gtagaagggt tatattttac tactgtggaa aaatatttaa gatagttttg    3780
ccagaacagt ttgtacagac gtatgcttat tttaaaattt tatctcttat tcagtaaaaa    3840
acaacttctt tgtaatcgtt atgtgtgtat atgtatgtgt gtatgggtgt gtgtttgtgt    3900
gagagacaga gaaagagaga gaattctttc aagtgaatct aaaagctttt gcttttcctt    3960
tgtttttatg aagaaaaaat acattttata ttagaagtgt taacttagct tgaaggatct    4020
gtttttaaaa atcataaact gtgtgcagac tcaataaaat catgtacatt tctgaaatga    4080
cctcaagatg tcctccttgt tctactcata tatctatc ttatatagtt tactatttta     4140
cttctagaga tagtacataa aggtggtatg tgtgtgtatg ctactacaaa aaagttgtta    4200
actaaattaa cattgggaaa tcttatattc catatattag catttagtcc aatgtctttt    4260
taagcttatt taattaaaaa atttccagtg agcttatcat gctgtcttta catggggttt    4320
tcaatttgc atgctcgatt attccctgta caatatttaa aatttattgc ttgatacttt     4380
tgacaacaaa ttaggttttg tacaattgaa cttaaataaa tgtcattaaa ataaataaat    4440
gcaatatgta ttaatattca ttgtataaaa atagaagaat acaaacatat ttgttaaata    4500
tttacatatg aaatttaata tagctatttt tatggaattt ttcattgata tgaaaaatat    4560
gatattgcat atgcatagtt cccatgttaa atcccattca taactttcat taaagcatttt  4620
actttgaatt tctccaatgc ttagaatgtt tttaccagga atggatgtcg ctaatcataa    4680
taaaattcaa ccattatttt tttcttgttt ataatacatt gtgttatatg ttcaaatatg    4740
aaaatgtgtat gcacctattg aaaatatgttt aatgcatttta ttaacatttg caggacactt   4800
ttacaggccc caattatcca atagtctaat aattgtttaa gatctag                 4847
```

<210> SEQ ID NO 30

<211> LENGTH: 1143
<212> TYPE: PRT
<213> ORGANISM: Homo sapiens

<400> SEQUENCE: 30

```
Met Tyr Leu Trp Leu Lys Leu Leu Ala Phe Gly Phe Ala Phe Leu Asp
1               5                   10                  15

Thr Glu Val Phe Val Thr Gly Gln Ser Pro Thr Pro Ser Pro Thr Asp
            20                  25                  30

Ala Tyr Leu Asn Ala Ser Glu Thr Thr Thr Leu Ser Pro Ser Gly Ser
        35                  40                  45

Ala Val Ile Ser Thr Thr Thr Ile Ala Thr Thr Pro Ser Lys Pro Thr
    50                  55                  60

Cys Asp Glu Lys Tyr Ala Asn Ile Thr Val Asp Tyr Leu Tyr Asn Lys
65                  70                  75                  80

Glu Thr Lys Leu Phe Thr Ala Lys Leu Asn Val Asn Glu Asn Val Glu
                85                  90                  95

Cys Gly Asn Asn Thr Cys Thr Asn Asn Glu Val His Asn Leu Thr Glu
            100                 105                 110

Cys Lys Asn Ala Ser Val Ser Ile Ser His Asn Ser Cys Thr Ala Pro
        115                 120                 125

Asp Lys Thr Leu Ile Leu Asp Val Pro Pro Gly Val Glu Lys Phe Gln
130                 135                 140

Leu His Asp Cys Thr Gln Val Glu Lys Ala Asp Thr Thr Ile Cys Leu
145                 150                 155                 160

Lys Trp Lys Asn Ile Glu Thr Phe Thr Cys Asp Thr Gln Asn Ile Thr
                165                 170                 175

Tyr Arg Phe Gln Cys Gly Asn Met Ile Phe Asp Asn Lys Glu Ile Lys
            180                 185                 190

Leu Glu Asn Leu Glu Pro Glu His Glu Tyr Lys Cys Asp Ser Glu Ile
        195                 200                 205

Leu Tyr Asn Asn His Lys Phe Thr Asn Ala Ser Lys Ile Ile Lys Thr
    210                 215                 220

Asp Phe Gly Ser Pro Gly Glu Pro Gln Ile Ile Phe Cys Arg Ser Glu
225                 230                 235                 240

Ala Ala His Gln Gly Val Ile Thr Trp Asn Pro Pro Gln Arg Ser Phe
                245                 250                 255

His Asn Phe Thr Leu Cys Tyr Ile Lys Glu Thr Glu Lys Asp Cys Leu
            260                 265                 270

Asn Leu Asp Lys Asn Leu Ile Lys Tyr Asp Leu Gln Asn Leu Lys Pro
        275                 280                 285

Tyr Thr Lys Tyr Val Leu Ser Leu His Ala Tyr Ile Ile Ala Lys Val
    290                 295                 300

Gln Arg Asn Gly Ser Ala Ala Met Cys His Phe Thr Thr Lys Ser Ala
305                 310                 315                 320

Pro Pro Ser Gln Val Trp Asn Met Thr Val Ser Met Thr Ser Asp Asn
                325                 330                 335

Ser Met His Val Lys Cys Arg Pro Pro Arg Asp Arg Asn Gly Pro His
            340                 345                 350

Glu Arg Tyr His Leu Glu Val Glu Ala Gly Asn Thr Leu Val Arg Asn
        355                 360                 365

Glu Ser His Lys Asn Cys Asp Phe Arg Val Lys Asp Leu Gln Tyr Ser
    370                 375                 380

Thr Asp Tyr Thr Phe Lys Ala Tyr Phe His Asn Gly Asp Tyr Pro Gly
```

-continued

```
            385                 390                 395                 400
Glu Pro Phe Ile Leu His His Ser Thr Ser Tyr Asn Ser Lys Ala Leu
                    405                 410                 415
Ile Ala Phe Leu Ala Phe Leu Ile Ile Val Thr Ser Ile Ala Leu Leu
                420                 425                 430
Val Val Leu Tyr Lys Ile Tyr Asp Leu His Lys Lys Arg Ser Cys Asn
            435                 440                 445
Leu Asp Glu Gln Gln Glu Leu Val Arg Asp Asp Glu Lys Gln Leu
        450                 455                 460
Met Asn Val Glu Pro Ile His Ala Asp Ile Leu Leu Glu Thr Tyr Lys
465                 470                 475                 480
Arg Lys Ile Ala Asp Glu Gly Arg Leu Phe Leu Ala Glu Phe Gln Ser
                485                 490                 495
Ile Pro Arg Val Phe Ser Lys Phe Pro Ile Lys Glu Ala Arg Lys Pro
                500                 505                 510
Phe Asn Gln Asn Lys Asn Arg Tyr Val Asp Ile Leu Pro Tyr Asp Tyr
                515                 520                 525
Asn Arg Val Glu Leu Ser Glu Ile Asn Gly Asp Ala Gly Ser Asn Tyr
            530                 535                 540
Ile Asn Ala Ser Tyr Ile Asp Gly Phe Lys Glu Pro Arg Lys Tyr Ile
545                 550                 555                 560
Ala Ala Gln Gly Pro Arg Asp Glu Thr Val Asp Asp Phe Trp Arg Met
                565                 570                 575
Ile Trp Glu Gln Lys Ala Thr Val Ile Val Met Val Thr Arg Cys Glu
                580                 585                 590
Glu Gly Asn Arg Asn Lys Cys Ala Glu Tyr Trp Pro Ser Met Glu Glu
            595                 600                 605
Gly Thr Arg Ala Phe Gly Asp Val Val Lys Ile Asn Gln His Lys
        610                 615                 620
Arg Cys Pro Asp Tyr Ile Ile Gln Lys Leu Asn Ile Val Asn Lys Lys
625                 630                 635                 640
Glu Lys Ala Thr Gly Arg Glu Val Thr His Ile Gln Phe Thr Ser Trp
                645                 650                 655
Pro Asp His Gly Val Pro Glu Asp Pro His Leu Leu Leu Lys Leu Arg
                660                 665                 670
Arg Arg Val Asn Ala Phe Ser Asn Phe Phe Ser Gly Pro Ile Val Val
            675                 680                 685
His Cys Ser Ala Gly Val Gly Arg Thr Gly Thr Tyr Ile Gly Ile Asp
        690                 695                 700
Ala Met Leu Glu Gly Leu Glu Ala Glu Asn Lys Val Asp Val Tyr Gly
705                 710                 715                 720
Tyr Val Val Lys Leu Arg Arg Gln Arg Cys Leu Met Val Gln Val Glu
                725                 730                 735
Ala Gln Tyr Ile Leu Ile His Gln Ala Leu Val Glu Tyr Asn Gln Phe
                740                 745                 750
Gly Glu Thr Glu Val Asn Leu Ser Glu Leu His Pro Tyr Leu His Asn
            755                 760                 765
Met Lys Lys Arg Asp Pro Pro Ser Glu Pro Ser Pro Leu Glu Ala Glu
        770                 775                 780
Phe Gln Arg Leu Pro Ser Tyr Arg Ser Trp Arg Thr Gln His Ile Gly
785                 790                 795                 800
Asn Gln Glu Glu Asn Lys Ser Lys Asn Arg Asn Ser Asn Val Ile Pro
                805                 810                 815
```

Tyr Asp Tyr Asn Arg Val Pro Leu Lys His Glu Leu Glu Met Ser Lys
            820                 825                 830

Glu Ser Glu His Asp Ser Asp Glu Ser Ser Asp Asp Ser Asp Ser
            835                 840                 845

Glu Glu Pro Ser Lys Tyr Ile Asn Ala Ser Phe Ile Met Ser Tyr Trp
850                 855                 860

Lys Pro Glu Val Met Ile Ala Ala Gln Gly Pro Leu Lys Glu Thr Ile
865                 870                 875                 880

Gly Asp Phe Trp Gln Met Ile Phe Gln Arg Lys Val Lys Val Ile Val
                885                 890                 895

Met Leu Thr Glu Leu Lys His Gly Asp Gln Glu Ile Cys Ala Gln Tyr
            900                 905                 910

Trp Gly Glu Gly Lys Gln Thr Tyr Gly Asp Ile Glu Val Asp Leu Lys
            915                 920                 925

Asp Thr Asp Lys Ser Ser Thr Tyr Thr Leu Arg Val Phe Glu Leu Arg
930                 935                 940

His Ser Lys Arg Lys Asp Ser Arg Thr Val Tyr Gln Tyr Gln Tyr Thr
945                 950                 955                 960

Asn Trp Ser Val Glu Gln Leu Pro Ala Glu Pro Lys Glu Leu Ile Ser
                965                 970                 975

Met Ile Gln Val Val Lys Gln Lys Leu Pro Gln Lys Asn Ser Ser Glu
            980                 985                 990

Gly Asn Lys His His Lys Ser Thr Pro Leu Leu Ile His Cys Arg Asp
            995                 1000                1005

Gly Ser Gln Gln Thr Gly Ile Phe Cys Ala Leu Leu Asn Leu Leu
    1010                1015                1020

Glu Ser Ala Glu Thr Glu Glu Val Val Asp Ile Phe Gln Val Val
    1025                1030                1035

Lys Ala Leu Arg Lys Ala Arg Pro Gly Met Val Ser Thr Phe Glu
    1040                1045                1050

Gln Tyr Gln Phe Leu Tyr Asp Val Ile Ala Ser Thr Tyr Pro Ala
    1055                1060                1065

Gln Asn Gly Gln Val Lys Lys Asn Asn His Gln Glu Asp Lys Ile
    1070                1075                1080

Glu Phe Asp Asn Glu Val Asp Lys Val Lys Gln Asp Ala Asn Cys
    1085                1090                1095

Val Asn Pro Leu Gly Ala Pro Glu Lys Leu Pro Glu Ala Lys Glu
    1100                1105                1110

Gln Ala Glu Gly Ser Glu Pro Thr Ser Gly Thr Glu Gly Pro Glu
    1115                1120                1125

His Ser Val Asn Gly Pro Ala Ser Pro Ala Leu Asn Gln Gly Ser
    1130                1135                1140

<210> SEQ ID NO 31
<211> LENGTH: 5186
<212> TYPE: DNA
<213> ORGANISM: Homo sapiens

<400> SEQUENCE: 31 agtattttg gagaagttag taaaaccgaa tctgacatca tcacctagca gttcatgcag      60
ctagcaagtg gtttgttctt agggtaacag aggaggaaat tgttcctcgt ctgataagac     120
aacagtggag aaaggacgca tgctgttttct taggacacg gctgacttcc agatatgacc    180 atgtattgt ggcttaaact cttggcattt ggctttgcct ttctggacac agaagtattt      240

|  |  |
|---|---|
| gtgacagggc aaagcccaac accttccccc actggattga ctacagcaaa gatgcccagt | 300 |
| gttccacttt caagtgaccc cttacctact cacaccactg cattctcacc cgcaagcacc | 360 |
| tttgaaagag aaaatgactt ctcagagacc acaacttctc ttagtccaga caatacttcc | 420 |
| acccaagtat cccggactc tttggataat gctagtgctt ttaataccac aggtgtttca | 480 |
| tcagtacaga cgcctcacct tcccacgcac gcagactcgc agacgccctc tgctggaact | 540 |
| gacacgcaga cattcagcgg ctccgccgcc aatgcaaaac tcaaccctac cccaggcagc | 600 |
| aatgctatct cagatgccta ccttaatgcc tctgaaacaa ccactctgag cccttctgga | 660 |
| agcgctgtca tttcaaccac aacaatagct actactccat ctaagccaac atgtgatgaa | 720 |
| aaatatgcaa acatcactgt ggattactta tataacaagg aaactaaatt atttacagca | 780 |
| aagctaaatg ttaatgagaa tgtggaatgt ggaaacaata cttgcacaaa caatgaggtg | 840 |
| cataacctta cagaatgtaa aaatgcgtct gtttccatat ctcataattc atgtactgct | 900 |
| cctgataaga cattaatatt agatgtgcca ccagggggttg aaaagtttca gttacatgat | 960 |
| tgtacacaag ttgaaaaagc agatactact atttgtttaa atggaaaaa tattgaaacc | 1020 |
| tttacttgtg atacacagaa tattacctac agatttcagt gtggtaatat gatatttgat | 1080 |
| aataagaaa ttaaattaga aaaccttgaa cccgaacatg agtataagtg tgactcagaa | 1140 |
| atactctata ataaccacaa gtttactaac gcaagtaaaa ttattaaaac gattttggg | 1200 |
| agtccaggag agcctcagat tatttttgt agaagtgaag ctgcacatca aggagtaatt | 1260 |
| acctggaatc ccctcaaag atcatttcat aattttaccc tctgttatat aaaagagaca | 1320 |
| gaaaaagatt gcctcaatct ggataaaaac ctgatcaaat atgatttgca aaatttaaaa | 1380 |
| ccttatacga aatatgttttt atcattacat gcctacatca ttgcaaaagt gcaacgtaat | 1440 |
| ggaagtgctg caatgtgtca tttcacaact aaaagtgctc ctccaagcca ggtctggaac | 1500 |
| atgactgtct ccatgacatc agataatagt atgcatgtca agtgtaggcc tcccagggac | 1560 |
| cgtaatggcc cccatgaacg ttaccatttg gaagttgaag ctggaaatac tctggttaga | 1620 |
| aatgagtcgc ataagaattg cgatttccgt gtaaaagatc ttcaatattc aacagactac | 1680 |
| acttttaagg cctatttttca caatggagac tatcctggag aacccttat tttacatcat | 1740 |
| tcaacatctt ataattctaa ggcactgata gcatttctgg catttctgat tattgtgaca | 1800 |
| tcaatagccc tgcttgttgt tctctacaaa atctatgatc tacataagaa aagatcctgc | 1860 |
| aatttagatg aacagcagga gcttgttgaa agggatgatg aaaaacaact gatgaatgtg | 1920 |
| gagccaatcc atgcagatat tttgttggaa acttataaga ggaagattgc tgatgaagga | 1980 |
| agactttttc tggctgaatt tcagagcatc ccgcgggtgt tcagcaagtt tcctataaag | 2040 |
| gaagctcgaa agcccttaa ccagaataaa aaccgttatg ttgacattct tccttatgat | 2100 |
| tataaccgtg ttgaactctc tgagataaac ggagatgcag ggtcaaacta cataaatgcc | 2160 |
| agctatattg atggtttcaa agaacccagg aaatacattg ctgcacaagg tcccagggat | 2220 |
| gaaactgttg atgatttctg gaggatgatt tgggaacaga agccacagt tattgtcatg | 2280 |
| gtcactcgat gtgaagaagg aaacaggaac aagtgtgcag aatactggcc gtcaatggaa | 2340 |
| gagggcactc gggcttttgg agatgttgtt gtaaagatca accagcacaa agatgtccca | 2400 |
| gattacatca ttcagaaatt gaacattgta aataaaaaag aaaagcaac tggaagagag | 2460 |
| gtgactcaca ttcagttcac cagctggcca gaccacgggg tgcctgagga tcctcacttg | 2520 |
| ctcctcaaac tgagaaggag agtgaatgcc ttcagcaatt tcttcagtgg tcccattgtg | 2580 |

```
gtgcactgca gtgctggtgt tgggcgcaca ggaacctata tcggaattga tgccatgcta    2640
gaaggcctgg aagccgagaa caaagtggat gtttatggtt atgttgtcaa gctaaggcga    2700
cagagatgcc tgatggttca agtagaggcc cagtacatct tgatccatca ggctttggtg    2760
gaatacaatc agtttggaga aacagaagtg aatttgtctg aattacatcc atatctacat    2820
aacatgaaga aaagggatcc acccagtgag ccgtctccac tagaggctga attccagaga    2880
cttccttcat ataggagctg gaggacacag cacattggaa atcaagaaga aaataaaagt    2940
aaaaacagga attctaatgt catcccatat gactataaca gagtgccact taaacatgag    3000
ctggaaatga gtaaagagag tgagcatgat tcagatgaat cctctgatga tgacagtgat    3060
tcagaggaac caagcaaata catcaatgca tcttttataa tgagctactg gaaacctgaa    3120
gtgatgattg ctgctcaggg accactgaag gagaccattg gtgacttttg gcagatgatc    3180
ttccaaagaa aagtcaaagt tattgttatg ctgacagaac tgaaacatgg agaccaggaa    3240
atctgtgctc agtactgggg agaaggaaag caaacatatg gagatattga agttgacctg    3300
aaagacacag acaaatcttc aacttatacc cttcgtgtct ttgaactgag acattccaag    3360
aggaaagact ctcgaactgt gtaccagtac caatatacaa actggagtgt ggagcagctt    3420
cctgcagaac ccaaggaatt aatctctatg attcaggtcg tcaaacaaaa acttccccag    3480
aagaattcct ctgaagggaa caagcatcac aagagtacac ctctactcat tcactgcagg    3540
gatggatctc agcaaacggg aatattttgt gctttgttaa atctcttaga aagtgcggaa    3600
acagaagagg tagtggatat ttttcaagtg gtaaaagctc tacgcaaagc taggccaggc    3660
atggtttcca cattcgagca atatcaattc ctatatgacg tcattgccag cacctaccct    3720
gctcagaatg gacaagtaaa gaaaaacaac catcaagaag ataaaattga atttgataat    3780
gaagtggaca aagtaaagca ggatgctaat tgtgttaatc cacttggtgc cccagaaaag    3840
ctccctgaag caaaggaaca ggctgaaggt tctgaaccca cgagtggcac tgaggggcca    3900
gaacattctg tcaatggtcc tgcaagtcca gctttaaatc aaggttcata ggaaaagaca    3960
taaatgagga aactccaaac ctcctgttag ctgttatttc tattttgta gaagtaggaa    4020 gtgaaaatag gtatacagtg gattaattaa atgcagcgaa ccaatatttg tagaagggtt    4080
atattttact actgtggaaa aatatttaag atagttttgc cagaacagtt tgtacagacg    4140
tatgcttatt ttaaaatttt atctcttatt cagtaaaaaa caacttcttt gtaatcgtta    4200
tgtgtgtata tgtatgtgtg tatgggtgtg tgtttgtgtg agagacagag aaagagagag    4260
aattctttca agtgaatcta aaagcttttg cttttccttt gttttatga agaaaaaata    4320 cattttatat tagaagtgtt aacttagctt gaaggatctg ttttaaaaa tcataaactg    4380 tgtgcagact caataaaatc atgtacattt ctgaaatgac ctcaagatgt cctccttgtt    4440
ctactcatat atatctatct tatatagttt actatttac ttctagagat agtacataaa    4500
ggtggtatgt gtgtgtatgc tactacaaaa aagttgttaa ctaaattaac attgggaaat    4560
cttatattcc atatattagc atttagtcca atgtcttttt aagcttattt aattaaaaaa    4620
tttccagtga gcttatcatg ctgtctttac atgggttttt caattttgca tgctcgatta    4680
ttccctgtac aatatttaaa atttattgct tgatacttttt gacaacaaat taggttttgt    4740
acaattgaac ttaaataaat gtcattaaaa taaataaatg caatatgtat taatattcat    4800
tgtataaaaa tagaagaata caaacatatt tgttaaatat ttacatatga aatttaatat    4860
agctattttt atgaattttt tcattgatat gaaaaatatg atattgcata tgcatagttc    4920
ccatgttaaa tcccattcat aactttcatt aaagcattta ctttgaattt ctccaatgct    4980
```

-continued

```
tagaatgttt ttaccaggaa tggatgtcgc taatcataat aaaattcaac cattatttt    5040 ttcttgttta taatacattg tgttatatgt tcaaatatga aatgtgtatg cacctattga    5100
aatatgttta atgcatttat taacatttgc aggacacttt tacaggcccc aattatccaa    5160
tagtctaata attgtttaag atctag                                         5186
```

<210> SEQ ID NO 32
<211> LENGTH: 1256
<212> TYPE: PRT
<213> ORGANISM: Homo sapiens

<400> SEQUENCE: 32

```
Met Tyr Leu Trp Leu Lys Leu Leu Ala Phe Gly Phe Ala Phe Leu Asp
1               5                   10                  15

Thr Glu Val Phe Val Thr Gly Gln Ser Pro Thr Pro Ser Pro Thr Gly
            20                  25                  30

Leu Thr Thr Ala Lys Met Pro Ser Val Pro Leu Ser Ser Asp Pro Leu
        35                  40                  45

Pro Thr His Thr Thr Ala Phe Ser Pro Ala Ser Thr Phe Glu Arg Glu
    50                  55                  60

Asn Asp Phe Ser Glu Thr Thr Thr Ser Leu Ser Pro Asp Asn Thr Ser
65                  70                  75                  80

Thr Gln Val Ser Pro Asp Ser Leu Asp Asn Ala Ser Ala Phe Asn Thr
                85                  90                  95

Thr Gly Val Ser Ser Val Gln Thr Pro His Leu Pro Thr His Ala Asp
            100                 105                 110

Ser Gln Thr Pro Ser Ala Gly Thr Asp Thr Gln Thr Phe Ser Gly Ser
        115                 120                 125

Ala Ala Asn Ala Lys Leu Asn Pro Thr Pro Gly Ser Asn Ala Ile Ser
130                 135                 140

Asp Ala Tyr Leu Asn Ala Ser Glu Thr Thr Thr Leu Ser Pro Ser Gly
145                 150                 155                 160

Ser Ala Val Ile Ser Thr Thr Thr Ile Ala Thr Thr Pro Ser Lys Pro
                165                 170                 175

Thr Cys Asp Glu Lys Tyr Ala Asn Ile Thr Val Asp Tyr Leu Tyr Asn
            180                 185                 190

Lys Glu Thr Lys Leu Phe Thr Ala Lys Leu Asn Val Asn Glu Asn Val
        195                 200                 205

Glu Cys Gly Asn Asn Thr Cys Thr Asn Asn Glu Val His Asn Leu Thr
    210                 215                 220

Glu Cys Lys Asn Ala Ser Val Ser Ile Ser His Asn Ser Cys Thr Ala
225                 230                 235                 240

Pro Asp Lys Thr Leu Ile Leu Asp Val Pro Pro Gly Val Glu Lys Phe
                245                 250                 255

Gln Leu His Asp Cys Thr Gln Val Glu Lys Ala Asp Thr Thr Ile Cys
            260                 265                 270

Leu Lys Trp Lys Asn Ile Glu Thr Phe Thr Cys Asp Thr Gln Asn Ile
        275                 280                 285

Thr Tyr Arg Phe Gln Cys Gly Asn Met Ile Phe Asp Asn Lys Glu Ile
    290                 295                 300

Lys Leu Glu Asn Leu Glu Pro Glu His Glu Tyr Lys Cys Asp Ser Glu
305                 310                 315                 320

Ile Leu Tyr Asn Asn His Lys Phe Thr Asn Ala Ser Lys Ile Ile Lys
                325                 330                 335
```

-continued

```
Thr Asp Phe Gly Ser Pro Gly Glu Pro Gln Ile Ile Phe Cys Arg Ser
        340                 345                 350
Glu Ala Ala His Gln Gly Val Ile Thr Trp Asn Pro Pro Gln Arg Ser
            355                 360                 365
Phe His Asn Phe Thr Leu Cys Tyr Ile Lys Glu Thr Glu Lys Asp Cys
        370                 375                 380
Leu Asn Leu Asp Lys Asn Leu Ile Lys Tyr Asp Leu Gln Asn Leu Lys
385                 390                 395                 400
Pro Tyr Thr Lys Tyr Val Leu Ser Leu His Ala Tyr Ile Ile Ala Lys
                405                 410                 415
Val Gln Arg Asn Gly Ser Ala Ala Met Cys His Phe Thr Thr Lys Ser
            420                 425                 430
Ala Pro Pro Ser Gln Val Trp Asn Met Thr Val Ser Met Thr Ser Asp
        435                 440                 445
Asn Ser Met His Val Lys Cys Arg Pro Pro Arg Asp Arg Asn Gly Pro
    450                 455                 460
His Glu Arg Tyr His Leu Glu Val Glu Ala Gly Asn Thr Leu Val Arg
465                 470                 475                 480
Asn Glu Ser His Lys Asn Cys Asp Phe Arg Val Lys Asp Leu Gln Tyr
                485                 490                 495
Ser Thr Asp Tyr Thr Phe Lys Ala Tyr Phe His Asn Gly Asp Tyr Pro
            500                 505                 510
Gly Glu Pro Phe Ile Leu His His Ser Thr Ser Tyr Asn Ser Lys Ala
        515                 520                 525
Leu Ile Ala Phe Leu Ala Phe Leu Ile Ile Val Thr Ser Ile Ala Leu
    530                 535                 540
Leu Val Val Leu Tyr Lys Ile Tyr Asp Leu His Lys Lys Arg Ser Cys
545                 550                 555                 560
Asn Leu Asp Glu Gln Gln Glu Leu Val Glu Arg Asp Asp Glu Lys Gln
                565                 570                 575
Leu Met Asn Val Glu Pro Ile His Ala Asp Ile Leu Leu Glu Thr Tyr
            580                 585                 590
Lys Arg Lys Ile Ala Asp Glu Gly Arg Leu Phe Leu Ala Glu Phe Gln
        595                 600                 605
Ser Ile Pro Arg Val Phe Ser Lys Phe Pro Ile Lys Glu Ala Arg Lys
    610                 615                 620
Pro Phe Asn Gln Asn Lys Asn Arg Tyr Val Asp Ile Leu Pro Tyr Asp
625                 630                 635                 640
Tyr Asn Arg Val Glu Leu Ser Glu Ile Asn Gly Asp Ala Gly Ser Asn
                645                 650                 655
Tyr Ile Asn Ala Ser Tyr Ile Asp Gly Phe Lys Glu Pro Arg Lys Tyr
            660                 665                 670
Ile Ala Ala Gln Gly Pro Arg Asp Glu Thr Val Asp Asp Phe Trp Arg
        675                 680                 685
Met Ile Trp Glu Gln Lys Ala Thr Val Ile Val Met Val Thr Arg Cys
    690                 695                 700
Glu Glu Gly Asn Arg Asn Lys Cys Ala Glu Tyr Trp Pro Ser Met Glu
705                 710                 715                 720
Glu Gly Thr Arg Ala Phe Gly Asp Val Val Lys Ile Asn Gln His
                725                 730                 735
Lys Arg Cys Pro Asp Tyr Ile Ile Gln Lys Leu Asn Ile Val Asn Lys
        740                 745                 750
```

-continued

```
Lys Glu Lys Ala Thr Gly Arg Glu Val Thr His Ile Gln Phe Thr Ser
        755                 760                 765

Trp Pro Asp His Gly Val Pro Glu Asp Pro His Leu Leu Lys Leu
        770                 775                 780

Arg Arg Arg Val Asn Ala Phe Ser Asn Phe Phe Ser Gly Pro Ile Val
785                 790                 795                 800

Val His Cys Ser Ala Gly Val Gly Arg Thr Gly Thr Tyr Ile Gly Ile
                805                 810                 815

Asp Ala Met Leu Glu Gly Leu Glu Ala Glu Asn Lys Val Asp Val Tyr
                820                 825                 830

Gly Tyr Val Val Lys Leu Arg Arg Gln Arg Cys Leu Met Val Gln Val
        835                 840                 845

Glu Ala Gln Tyr Ile Leu Ile His Gln Ala Leu Val Glu Tyr Asn Gln
        850                 855                 860

Phe Gly Glu Thr Glu Val Asn Leu Ser Glu Leu His Pro Tyr Leu His
865                 870                 875                 880

Asn Met Lys Lys Arg Asp Pro Ser Glu Pro Ser Pro Leu Glu Ala
                885                 890                 895

Glu Phe Gln Arg Leu Pro Ser Tyr Arg Ser Trp Arg Thr Gln His Ile
                900                 905                 910

Gly Asn Gln Glu Glu Asn Lys Ser Lys Asn Arg Asn Ser Asn Val Ile
        915                 920                 925

Pro Tyr Asp Tyr Asn Arg Val Pro Leu Lys His Glu Leu Glu Met Ser
    930                 935                 940

Lys Glu Ser Glu His Asp Ser Asp Glu Ser Ser Asp Asp Ser Asp
945                 950                 955                 960

Ser Glu Glu Pro Ser Lys Tyr Ile Asn Ala Ser Phe Ile Met Ser Tyr
                965                 970                 975

Trp Lys Pro Glu Val Met Ile Ala Ala Gln Gly Pro Leu Lys Glu Thr
                980                 985                 990

Ile Gly Asp Phe Trp Gln Met Ile Phe Gln Arg Lys Val Lys Val Ile
    995                 1000                1005

Val Met Leu Thr Glu Leu Lys His Gly Asp Gln Glu Ile Cys Ala
    1010                1015                1020

Gln Tyr Trp Gly Glu Gly Lys Gln Thr Tyr Gly Asp Ile Glu Val
    1025                1030                1035

Asp Leu Lys Asp Thr Asp Lys Ser Ser Thr Tyr Thr Leu Arg Val
    1040                1045                1050

Phe Glu Leu Arg His Ser Lys Arg Lys Asp Ser Arg Thr Val Tyr
    1055                1060                1065

Gln Tyr Gln Tyr Thr Asn Trp Ser Val Glu Gln Leu Pro Ala Glu
    1070                1075                1080

Pro Lys Glu Leu Ile Ser Met Ile Gln Val Val Lys Gln Lys Leu
    1085                1090                1095

Pro Gln Lys Asn Ser Ser Glu Gly Asn Lys His His Lys Ser Thr
    1100                1105                1110

Pro Leu Leu Ile His Cys Arg Asp Gly Ser Gln Gln Thr Gly Ile
    1115                1120                1125

Phe Cys Ala Leu Leu Asn Leu Leu Glu Ser Ala Glu Thr Glu Glu
    1130                1135                1140

Val Val Asp Ile Phe Gln Val Val Lys Ala Leu Arg Lys Ala Arg
    1145                1150                1155

Pro Gly Met Val Ser Thr Phe Glu Gln Tyr Gln Phe Leu Tyr Asp
```

```
                1160                1165                1170

Val Ile Ala Ser Thr Tyr Pro Ala Gln Asn Gly Gln Val Lys Lys
    1175                1180                1185

Asn Asn His Gln Glu Asp Lys Ile Glu Phe Asp Asn Glu Val Asp
    1190                1195                1200

Lys Val Lys Gln Asp Ala Asn Cys Val Asn Pro Leu Gly Ala Pro
    1205                1210                1215

Glu Lys Leu Pro Glu Ala Lys Glu Gln Ala Glu Gly Ser Glu Pro
    1220                1225                1230

Thr Ser Gly Thr Glu Gly Pro Glu His Ser Val Asn Gly Pro Ala
    1235                1240                1245

Ser Pro Ala Leu Asn Gln Gly Ser
    1250                1255

<210> SEQ ID NO 33
<211> LENGTH: 1107
<212> TYPE: DNA
<213> ORGANISM: Homo sapiens

<400> SEQUENCE: 33 agtattttg gagaagttag taaaaccgaa tctgacatca tcacctagca gttcatgcag       60
ctagcaagtg gtttgttctt agggtaacag aggaggaaat tgttcctcgt ctgataagac      120
aacagtggag aaaggacgca tgctgtttct tagggacacg gctgacttcc agatatgacc      180
atgtatttgt ggcttaaact cttggcattt ggctttgcct ttctggacac agaagtattt      240
gtgacagggc aaagcccaac accttccccc actggtaaga attaatattt atatttttac      300
taatttatt ttcttgttgc aaagtttata tatttaacta caattttcta ttattaacac      360
tgaaattatt tttaaggata aatttataa tcatgagtga ttcttgacat tcacttgttc      420
ttaaactttc tgcttatacg ttatagagtt taataactac ctaaacatgt tattaaattt      480
gtatatatat tttgtgtata aatagtaact tttcccaaac ttgacagtaa atcacacaac      540
aggtttctac tctctttaa tattttaaga ctataaaaaa atgcatttaa attagataac      600
aaaattttat agtctgaaag caggttaaca gctgtctatg tatgttatag atatgtagat      660
aacagatttg catatgtcta tatttcttta agagtatgtt gctttttca atggtatgca      720
aaacctttga gactattgag atatttttaa ataataattt tcaaattcta ctgaacactt      780
caatagtcct tataaatgtc ttaatcatga gataaattta aaacacagag atgctgcaaa      840
taaattcata catagtacat acaaaataag agaaaaaatt aaattgcaga tggttaaata      900
tcacatcact taactgatgt tactgaaaat gtattttcct gcataatcat atggttgaca      960
gtatgcatta agaaggtaag taaaacaatg aagacaattt tgatttaata tggtaatgca     1020
caattccaac taacgtacat tcaacagatc atgaaattgg gttattaaaa tgaatatttt     1080
tgtcattaaa taaaaattcc gtccaaa                                         1107

<210> SEQ ID NO 34
<211> LENGTH: 34
<212> TYPE: PRT
<213> ORGANISM: Homo sapiens

<400> SEQUENCE: 34

Met Tyr Leu Trp Leu Lys Leu Leu Ala Phe Gly Phe Ala Phe Leu Asp
1               5                   10                  15

Thr Glu Val Phe Val Thr Gly Gln Ser Pro Thr Pro Ser Pro Thr Gly
            20                  25                  30
```

Lys Asn

<210> SEQ ID NO 35
<211> LENGTH: 1619
<212> TYPE: DNA
<213> ORGANISM: Homo sapiens

<400> SEQUENCE: 35

| | | | | | |
|---|---|---|---|---|---|
| aacattcctg | caaatggttt | caatatatgc | agatgtctcg | ataggaat gaaattacgt | 60 |
| ctttggaaca | acttaaataa | gtcaaatata | cttggagctt | taaaaattaa aaggagagag | 120 |
| attcgagcac | cttttctgct | gccatgacaa | ccatgcaagg | aatggaacag gccatgccag | 180 |
| gggctggccc | tggtgtgccc | cagctgggaa | acatggctgt | catacattca catctgtgga | 240 |
| aaggattgca | agagaagttc | ttgaagggag | aacccaaagt | ccttggggtt gtgcagattc | 300 |
| tgactgccct | gatgagcctt | agcatgggaa | taacaatgat | gtgtatggca tctaatactt | 360 |
| atggaagtaa | ccctatttcc | gtgtatatcg | ggtacacaat | ttgggggtca gtaatgttta | 420 |
| ttatttcagg | atccttgtca | attgcagcag | gaattagaac | tacaaaaggc ctggtccgag | 480 |
| gtagtctagg | aatgaatatc | accagctctg | tactggctgc | atcagggatc ttaatcaaca | 540 |
| catttagctt | ggcgttttat | tcattccatc | acccttactg | taactactat ggcaactcaa | 600 |
| ataattgtca | tgggactatg | tccatcttaa | tgggtctgga | tggcatggtg ctcctcttaa | 660 |
| gtgtgctgga | attctgcatt | gctgtgtccc | tctctgcctt | tggatgtaaa gtgctctgtt | 720 |
| gtacccctgg | tggggttgtg | ttaattctgc | catcacattc | tcacatggca gaaacagcat | 780 |
| ctcccacacc | acttaatgag | gtttgaggcc | accaaaagat | caacagacaa atgctccaga | 840 |
| aatctatgct | gactgtgaca | caagagcctc | acatgagaaa | ttaccagtat ccaacttcga | 900 |
| tactgataga | cttgttgata | ttattattat | atgtaatcca | attgaact gtgtgtgtat | 960 |
| agagagataa | taaattcaaa | attatgttct | cattttttc | cctggaactc aataactcat | 1020 |
| ttcactggct | ctttatcgag | agtactagaa | gttaaattaa | taataatgc atttaatgag | 1080 |
| gcaacagcac | ttgaaagttt | ttcattcatc | ataagaactt | tatataaagg cattacattg | 1140 |
| gcaaataagg | tttggaagca | gaagagcaaa | aaaagatat | tgttaaaatg aggcctccat | 1200 |
| gcaaaacaca | tacttccctc | ccatttattt | aactttttt | ttctcctacc tatgggacc | 1260 |
| aaagtgcttt | ttccttcagg | aagtggagat | gcatggccat | ctcccctcc ctttttcctt | 1320 |
| ctcctgcttt | tctttcccca | tagaaagtac | cttgaagtag | cacagtccgt ccttgcatgt | 1380 |
| gcacgagcta | tcatttgagt | aaaagtatac | atggagtaaa | aatcatatta agcatcagat | 1440 |
| tcaacttata | ttttctattt | catcttcttc | ctttcccttc | tcccaccttc tactgggcat | 1500 |
| aattatatct | taatcatata | tggaaatgtg | caacatatgg | tatttgttaa atacgtttgt | 1560 |
| ttttattgca | gagcaaaaat | aaatcaaatt | agaagcaata | aaaaaaaaaa aaaaaaaa | 1619 |

<210> SEQ ID NO 36
<211> LENGTH: 220
<212> TYPE: PRT
<213> ORGANISM: Homo sapiens

<400> SEQUENCE: 36

Met Thr Thr Met Gln Gly Met Glu Gln Ala Met Pro Gly Ala Gly Pro
1               5                   10                  15

Gly Val Pro Gln Leu Gly Asn Met Ala Val Ile His Ser His Leu Trp
            20                  25                  30

```
Lys Gly Leu Gln Glu Lys Phe Leu Lys Gly Glu Pro Lys Val Leu Gly
         35                  40                  45
Val Val Gln Ile Leu Thr Ala Leu Met Ser Leu Ser Met Gly Ile Thr
 50                  55                  60
Met Met Cys Met Ala Ser Asn Thr Tyr Gly Ser Asn Pro Ile Ser Val
 65                  70                  75                  80
Tyr Ile Gly Tyr Thr Ile Trp Gly Ser Val Met Phe Ile Ile Ser Gly
                 85                  90                  95
Ser Leu Ser Ile Ala Ala Gly Ile Arg Thr Lys Gly Leu Val Arg
            100                 105                 110
Gly Ser Leu Gly Met Asn Ile Thr Ser Ser Val Leu Ala Ala Ser Gly
            115                 120                 125
Ile Leu Ile Asn Thr Phe Ser Leu Ala Phe Tyr Ser Phe His His Pro
130                 135                 140
Tyr Cys Asn Tyr Tyr Gly Asn Ser Asn Asn Cys His Gly Thr Met Ser
145                 150                 155                 160
Ile Leu Met Gly Leu Asp Gly Met Val Leu Leu Ser Val Leu Glu
                165                 170                 175
Phe Cys Ile Ala Val Ser Leu Ser Ala Phe Gly Cys Lys Val Leu Cys
            180                 185                 190
Cys Thr Pro Gly Gly Val Val Leu Ile Leu Pro Ser His Ser His Met
            195                 200                 205
Ala Glu Thr Ala Ser Pro Thr Pro Leu Asn Glu Val
            210                 215                 220
```

<210> SEQ ID NO 37
<211> LENGTH: 3510
<212> TYPE: DNA
<213> ORGANISM: Homo sapiens

<400> SEQUENCE: 37

```
tcaatcgcct tttatctctg gccctgggac ctttgcctat tttctgattg ataggctttg     60
ttttgtcttt acctccttct ttctggggaa aacttcagtt ttatcgcacg ttcccctttt    120
ccatatcttc atcttccctc tacccagatt gtgaagatgg aaagggtcca accctggaa    180
gagaatgtgg gaaatgcagc caggccaaga ttcgagagga caagctatt gctggtggcc    240
tctgtaattc agggactggg gctgctcctg tgcttcacct acatctgcct gcacttctct    300
gctcttcagg tatcacatcg gtatcctcga attcaaagta tcaaagtaca atttaccgaa    360
tataagaagg agaaaggttt catcctcact tcccaaaagg aggatgaaat catgaaggtg    420
cagaacaact cagtcatcat caactgtgat gggttttatc tcatctccct gaagggctac    480
ttctcccagg aagtcaacat tagccttcat taccagaagg atgaggagcc cctcttccaa    540
ctgaagaagg tcaggtctgt caactccttg atggtggcct ctctgactta caaagacaaa    600
gtctacttga atgtgaccac tgacaatacc tccctggatg acttccatgt gaatggcgga    660
gaactgattc ttatccatca aaatcctggt gaattctgtg tcctttgagg ggctgatggc    720
aatatctaaa accaggcacc agcatgaaca ccaagctggg ggtggacagg gcatggattc    780
ttcattgcaa gtgaaggagc ctcccagctc agccacgtgg gatgtgacaa gaagcagatc    840
ctggccctcc cgccccacc cctcagggat atttaaaact tatttatat accagttaat    900
cttatttatc cttatatttt ctaaattgcc tagccgtcac accccaagat tgccttgagc    960
ctactaggca ccttttgtga aagaaaaaaa tagatgcctc ttcttcaaga tgcattgttt   1020
ctattggtca ggcaattgtc ataataaact tatgtcattg aaaacggtac ctgactacca   1080
```

```
tttgctggaa atttgacatg tgtgtggcat tatcaaaatg aagaggagca aggagtgaag    1140
gagtggggtt atgaatctgc caaggtggt  atgaaccaac ccctggaagc caaagcggcc    1200
tctccaaggt taaattgatt gcagtttgca tattgcctaa atttaaactt tctcatttgg    1260
tgggggttca aagaagaat  cagcttgtga aaaatcagga cttgaagaga gccgtctaag    1320
aaataccacg tgctttttt  ctttaccatt ttgctttccc agcctccaaa catagttaat    1380
agaaatttcc cttcaaagaa ctgtctgggg atgtgatgct ttgaaaaatc taatcagtga    1440
cttaagagag atttttcttgt atacagggag agtgagataa cttattgtga agggttagct    1500
ttactgtaca ggatagcagg gaactggaca tctcagggta aaagtcagta cggatttaa     1560 tagcctgggg aggaaaacac attctttgcc acagacaggc aaagcaacac atgctcatcc    1620
tcctgcctat gctgagatac gcactcagct ccatgtcttg tacacacaga acattgctg     1680 gtttcaagaa atgaggtgat cctattatca aattcaatct gatgtcaaat agcactaaga    1740
agttattgtg ccttatgaaa ataatgatc  tctgtctaga ataccatag  accatatata    1800 gtctcacatt gataattgaa actagaaggg tctaatatca gcctatgcca gggcttcaat    1860
ggaatagtat ccccttatgt ttagttgaaa tgtcccctta acttgatata atgtgttatg    1920
cttatggcgc tgtggacaat ctgattttc  atgtcaactt tccagatgat ttgtaacttc    1980
tctgtgccaa acctttata  aacataaatt tttgagatat gtattttaaa attgtagcac    2040
atgtttccct gacattttca atagaggata caacatcaca gaatcttct  ggatgattct    2100 gtgttatcaa ggaattgtac tgtgctacaa ttatctctag aatctccaga aaggtggagg    2160
gctgttcgcc cttacactaa atggtctcag ttggattttt tttcctgtt  ttctatttcc    2220 tcttaagtac accttcaact atattcccat ccctctattt taatctgtta tgaaggaagg    2280
taaataaaaa tgctaaatag aagaaattgt aggtaaggta agaggaatca agttctgagt    2340
ggctgccaag gcactcacag aatcataatc atggctaaat atttatggag gcctactgt     2400 ggaccaggca ctgggctaaa tacttacatt tacaagaatc attctgagac agatattcaa    2460
tgatatctgg cttcactact cagaagattg tgtgtgtgtt tgtgtgtgtg tgtgtgtgtg    2520
tatttcactt tttgttattg accatgttct gcaaaattgc agttactcag tgagtgatat    2580
ccgaaaaagt aaacgtttat gactataggt aatatttaag aaaatgcatg gttcattttt    2640
aagtttggaa ttttatctta tatttctcac agatgtgcag tgcacatgca ggcctaagta    2700
tatgttgtgt gtgttgtttg tctttgatgt catggtcccc tctcttaggt gctcactcgc    2760
tttgggtgca cctggcctgc tcttcccatg ttggcctctg caaccacaca gggatatttc    2820
tgctatgcac cagcctcact ccaccttcct tccatcaaaa atatgtgtgt gtgtctcagt    2880
ccctgtaagt catgtccttc acagggagaa ttaacccttc gatatacatg gcagagtttt    2940
gtggaaaaag aattgaatga aaagtcagga gatcagaatt ttaaatttga cttagccact    3000
aactagccat gtaaccttgg gaaagtcatt tcccatttct gggtcttgct tttctttctg    3060
ttaaatgaga ggaatgttaa atatctaaca gtttagaatc ttatgcttac agtgttatct    3120
gtgaatgcac atattaaatg tctatgttct tgttgctatg agtcaaggag tgtaaccttc    3180
tcctttacta tgttgaatgt attttttttct ggacaagctt acatcttcct cagccatctt    3240
tgtgagtcct tcaagagcag ttatcaattg ttagttagat attttctatt tagagaatgc    3300
ttaagggatt ccaatcccga tccaaatcat aatttgttct taagtatact gggcaggtcc    3360 cctatttaa  gtcataattt tgtatttagt gctttcctgg ctctcagaga gtattaatat    3420
```

```
tgatattaat aatatagtta atagtaatat tgctatttac atggaaacaa ataaaagatc      3480
tcagaattca ctaaaaaaaa aaaaaaaaaa                                      3510
```

<210> SEQ ID NO 38
<211> LENGTH: 183
<212> TYPE: PRT
<213> ORGANISM: Homo sapiens

<400> SEQUENCE: 38

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Thr Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

<210> SEQ ID NO 39
<211> LENGTH: 2056
<212> TYPE: DNA
<213> ORGANISM: Homo sapiens

<400> SEQUENCE: 39

```
aaagttacat tttctctgga actctcctag gccactccct gctgatgcaa catctgggtt       60
tgggcagaaa ggagggtgct tcggagcccg ccctttctga gcttcctggg ccggctctag      120
aacaattcag gcttcgctgc gactcagacc tcagctccaa catatgcatt ctgaagaaag      180
atggctgaga tggacagaat gctttatttt ggaaagaaac aatgttctag gtcaaactga      240
gtctaccaaa tgcagacttt cacaatggtt ctagaagaaa tctggacaag tcttttcatg      300
tggttttcct acgcattgat tccatgtttg ctcacagatg aagtggccat tctgcctgcc      360
cctcagaacc tctctgtact ctcaaccaac atgaagcatc tcttgatgtg agcccagtg       420 atcgcgcctg gagaaacagt gtactattct gtcgaatacc aggggagta cgagagcctg       480 tacacgagcc acatctggat ccccagcagc tggtgctcac tcactgaagg tcctgagtgt      540
gatgtcactg atgacatcac ggccactgtg ccatacaacc ttcgtgtcag gccacattg       600 ggctcacaga cctcagcctg gagcatcctg aagcatccct taatagaaa ctcaaccatc      660 cttacccgac ctgggatgga gatcaccaaa gatggcttcc acctggttat tgagctggag      720
```

-continued

```
gacctggggc cccagtttga gttccttgtg gcctactgga ggagggagcc tggtgccgag      780
gaacatgtca aaatggtgag gagtgggggt attccagtgc acctagaaac catggagcca      840
ggggctgcat actgtgtgaa ggcccagaca ttcgtgaagg ccattgggag gtacagcgcc      900
ttcagccaga cagaatgtgt ggaggtgcaa ggagaggcca ttcccctggt actggccctg      960
tttgcctttg ttggcttcat gctgatcctt gtggtcgtgc cactgttcgt ctggaaaatg     1020
ggccggctgc tccagtactc ctgttgcccc gtggtggtcc tcccagacac cttgaaaata     1080
accaattcac cccagaagtt aatcagctgc agaagggagg aggtggatgc ctgtgccacg     1140
gctgtgatgt ctcctgagga actcctcagg gcctggatct cataggtttg cggaagggcc     1200
caggtgaagc cgagaacctg gtctgcatga catggaaacc atgaggggac aagttgtgtt     1260
tctgttttcc gccacggaca agggatgaga gaagtaggaa gagcctgttg tctacaagtc     1320
tagaagcaac catcagaggc agggtggttt gtctaacaga acactgactg aggcttaggg     1380
gatgtgacct ctagactggg ggctgccact tgctggctga gcaaccctgg gaaaagtgac     1440
ttcatccctt cggtcctaag ttttctcatc tgtaatgggg gaattaccta cacacctgct     1500
aaacacacac acacagagtc tctctctata tatacacacg tacacataaa tacacccagc     1560
acttgcaagg ctagagggaa actggtgaca ctctacagtc tgactgattc agtgtttctg     1620
gagagcagga cataaatgta tgatgagaat gatcaaggac tctacacact gggtggcttg     1680
gagagcccac tttcccagaa taatccttga gagaaaagga atcatgggag caatggtgtt     1740
gagttcactt caagcccaat gccggtgcag aggggaatgg cttagcgagc tctacagtag     1800
gtgacctgga ggaaggtcac agccacactg aaaatgggat gtgcatgaac acggaggatc     1860
catgaactac tgtaaagtgt tgacagtgtg tgcacactgc agacagcagg tgaaatgtat     1920
gtgtgcaatg cgacgagaat gcagaagtca gtaacatgtg catgtttgtt gtgctccttt     1980
tttctgttgg taaagtacag aattcagcaa ataaaagggg ccaccctggc caaaagcggt     2040
aaaaaaaaaa aaaaaa                                                    2056
```

<210> SEQ ID NO 40
<211> LENGTH: 311
<212> TYPE: PRT
<213> ORGANISM: Homo sapiens

<400> SEQUENCE: 40

```
Met Gln Thr Phe Thr Met Val Leu Glu Glu Ile Trp Thr Ser Leu Phe
1               5                   10                  15

Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Glu Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125
```

-continued

```
His Pro Phe Asn Arg Asn Ser Thr Ile Leu Thr Arg Pro Gly Met Glu
    130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Ile Pro Leu Val Leu Ala Leu Phe Ala Phe
225                 230                 235                 240

Val Gly Phe Met Leu Ile Leu Val Val Pro Leu Phe Val Trp Lys
                245                 250                 255

Met Gly Arg Leu Leu Gln Tyr Ser Cys Cys Pro Val Val Leu Pro
                260                 265                 270

Asp Thr Leu Lys Ile Thr Asn Ser Pro Gln Lys Leu Ile Ser Cys Arg
                275                 280                 285

Arg Glu Glu Val Asp Ala Cys Ala Thr Ala Val Met Ser Pro Glu Glu
    290                 295                 300

Leu Leu Arg Ala Trp Ile Ser
305                 310
```

<210> SEQ ID NO 41
<211> LENGTH: 6475
<212> TYPE: DNA
<213> ORGANISM: Homo sapiens

<400> SEQUENCE: 41

```
ggcgaggcga ggtttgctgg ggtgaggcag cggcgcggcc gggccgggcc gggccacagg      60
cggtggcggc gggaccatgg aggcggcggt cgctgctccg cgtccccggc tgctcctcct     120
cgtgctggcg gcggcggcgg cggcggcggc ggcgctgctc ccggggcga cggcgttaca      180
gtgtttctgc cacctctgta caaaagacaa ttttacttgt gtgacagatg ggctctgctt     240
tgtctctgtc acagagacca cagacaaagt tatacacaac agcatgtgta tagctgaaat     300
tgacttaatt cctcgagata ggccgtttgt atgtgcaccc tcttcaaaaa ctgggtctgt     360
gactacaaca tattgctgca atcaggacca ttgcaataaa atagaacttc caactactgt     420
aaagtcatca cctggccttg gtcctgtgga actggcagct gtcattgctg accagtgtg      480
cttcgtctgc atctcactca tgttgatggt ctatatctgc cacaaccgca ctgtcattca     540
ccatcgagtg ccaaatgaag aggacccttc attagatcgc ccttttattt cagagggtac     600
tacgttgaaa gacttaattt atgatatgac aacgtcaggt tctggctcag gtttaccatt     660
gcttgttcag agaacaattg cgagaactat tgtgttacaa gaaagcattg caaaggtcg      720
atttggagaa gtttggagag aaagtggcg gggagaagaa gttgctgtta agatattctc      780
ctctagagaa gaacgttcgt ggttccgtga ggcagagatt tatcaaactg taatgttacg     840
tcatgaaaac atcctgggat ttatagcagc agacaataaa gacaatggta cttggactca     900
gctctggttg gtgtcagatt atcatgagca tggatccctt tttgattact aaacagata     960
cacagttact gtggaaggaa tgataaaact tgctctgtcc acggcgagcg gtcttgccca    1020
tcttcacatg gagattgttg gtacccaagg aaagccagcc attgctcata gagatttgaa    1080
```

```
atcaaagaat atcttggtaa agaagaatgg aacttgctgt attgcagact taggactggc   1140
agtaagacat gattcagcca cagataccat tgatattgct ccaaaccaca gagtgggaac   1200
aaaaaggtac atggcccctg aagttctcga tgattccata aatatgaaac attttgaatc   1260
cttcaaacgt gctgacatct atgcaatggg cttagtattc tgggaaattg ctcgacgatg   1320
ttccattggt ggaattcatg aagattacca actgccttat tatgatcttg taccttctga   1380
cccatcagtt gaagaaatga gaaaagttgt ttgtgaacag aagttaaggc caaatatccc   1440
aaacagatgg cagagctgtg aagccttgag agtaatggct aaaattatga gagaatgttg   1500
gtatgccaat ggagcagcta ggcttacagc attgcggatt aagaaaacat tatcgcaact   1560
cagtcaacag gaaggcatca aaatgtaatt ctacagcttt gcctgaactc tccttttttc   1620
ttcagatctg ctcctgggtt ttaatttggg aggtcaattg ttctacctca ctgagaggga   1680
acagaaggat attgcttcct tttgcagcag tgtaataaag tcaattaaaa acttcccagg   1740
atttctttgg acccaggaaa cagccatgtg ggtccttttct gtgcactatg aacgcttctt   1800
tcccaggaca gaaaatgtgt agtctaccct tattttttat taacaaaact tgttttttaa   1860
aaagatgatt gctggtctta actttaggta actctgctgt gctggagatc atctttaagg   1920
gcaaaggagt tggattgctg aattacaatg aaacatgtct tattactaaa gaaagtgatt   1980
tactcctggt tagtacattc tcagaggatt ctgaaccact agagtttcct tgattcagac   2040
tttgaatgta ctgttctata gttttttcagg atcttaaaac taacacttat aaaactctta   2100
tcttgagtct aaaaatgacc tcatatagta gtgaggaaca taattcatgc aattgtattt   2160
tgtatactat tattgttctt tcacttattc agaacattac atgccttcaa atgggattg    2220
tactatacca gtaagtgcca cttctgtgtc tttctaatgg aaatgagtag aattgctgaa   2280
agtctctatg ttaaaaccta tagtgtttga attcaaaaag cttatttatc tgggtaaccc   2340
aaacttttttc tgttttgttt ttggaagggt ttttgtggta tgtcatttgg tattctattc   2400
tgaaaatgcc tttctcctac caaaatgtgc ttaagccact aaagaaatga agtggcatta   2460
attagtaaat tattagcatg gtcatgtttg aatattctca catcaagctt ttgcatttta   2520
attgtgttgt ctaagtatac ttttaaaaaa tcaagtggca ctctagatgc ttatagtact   2580
ttaatatttg tagcatacag actaattttt ctaaaaggga aagtctgtct agctgcttgt   2640
gaaaagttat gtggtattct gtaagccatt ttttcttta tctgttcaaa gacttatttt    2700
ttaagacatg aattacattt aaaattagaa tatggttaat attaaataat aggccttttt   2760
ctaggaaggc gaaggtagtt aataatttga atagataaca gatgtgcaag aaagtcacat   2820
ttgttatgta tgtaggagta aacgttcggt ggatcctctg tctttgtaac tgaggttaga   2880
gctagtgtgg ttttgaggtc tcactacact ttgaggaagg cagcttttaa ttcagtgttt   2940
ccttatgtgt gcgtacattg caactgctta catgtaattt atgtaatgca ttcagtgcac   3000
ccttgttact tgggagaggt ggtagctaaa gaacattctg agtataggtt tttctccatt   3060
tacagatgtc tttggtcaaa tattgaaagc aaacttgtca tggtcttctt acattaagtt   3120
gaaactagct tataataact ggttttact tccaatgcta tgaagtctct gcagggcttt    3180
tacagttttc gaagtccttt tatcactgtg atcttattct gagggagaa aaaactatca    3240
tagctctgag gcaagacttc gactttatag tgctatcagt tccccgatac agggtcagag   3300
taacccatac agtattttgg tcaggaagag aaagtggcca tttacactga atgagttgca   3360
ttctgataat gtcttatctc ttatacgtag aataaatttg aaagactatt tgatcttaaa   3420
```

```
accaaagtaa ttttagaatg agtgacatat tacataggaa tttagtgtca atttcatgtg   3480
tttaaaaaca tcatgggaaa aatgcttaga ggttactatt ttgactacaa agttgagttt   3540
ttttctgtag ttaccataat ttcattgaag caaatgaatg agtttgagag gtttgttttt   3600
atagttgtgt tgtattactt gtttaataat aatctctaat tctgtgatca ggtactttt    3660 ttgtgggggt tttttttttg tttttttttt tttgttgttg tttttgggcc atttctaagc   3720
ctaccagatc tgctttatga atccagggg accaatgcat tttatcacta aaactattt    3780 tatataattt taagaatata ccaaaagttg tctgatttaa agttgtaata catgatttct   3840
cactttcatg taaggttatc cacttttgct gaagatattt tttattgaat caagattga    3900 gttacaatta tacttttctt acctaagtgg ataaaatgta cttttgatga atcagggaat   3960
ttttttaaag ttggagtta gttctaaatt gactttacgt attactgcag ttaattcctt    4020
ttttggctag ggatggtttg ataaaccaca attggctgat attgaaaatg aaagaaactt   4080 aaaggtggg atggatcatg attactgtcg ataactgcag ataaatttga ttagagtaat    4140
aattttgtca tttaaaaaca cagttgttta tactgcccat cctaggatgc tcaccttcca   4200
agattcaacg tggctaaaac atcttctggt aaattgtgcg tccatattca ttttgtcagt   4260
agccaggaga atggggatg ggggaaatac gacttagtga ggcatagaca tccctggtcc    4320
atcctttctg tctccagctg tttcttggaa cctgctctcc tgcttgctgg tccctgacgc   4380
agagaccgtt gcctccccca cagccgtttg actgaaggct gctctggaga cctagagtaa   4440
aacggctgat ggaagttgtg ggacccactt ccatttcctt cagtcattag aggtggaagg   4500 gagggtctc caagttggga gattgagcag atgaggcttg ggatgcccct gcttgactt     4560 cagccatgga tgaggagtgg gatggcagca aggtggctcc tgtggcagtg gagttgtgcc   4620
agaaacagtg gccagttgta tcgcctataa gacagggtaa ggtctgaaga gctgagcctg   4680
taattctgct gtaataatga tagtgctcaa gaagtgcctt gagttggtgt acagtgccat   4740
ggccatcaag aatcccagat ttcaggtttt attacaaaat gtaagtggtc acttggcgat   4800
tttgtagtac atgcatgagt tacctttttt ctctatgtct gagaactgtc agattaaaac   4860
aagatggcaa agagatcgtt agagtgcaca acaaaatcac tatcccatta gacacatcat   4920
caaaagctta tttttattct tgcactggaa gaatcgtaag tcaactgttt cttgaccatg   4980
gcagtgttct ggctccaaat ggtagtgatt ccaataatg gttctgttaa cacttttggca   5040 gaaaatgcca gctcagatat tttgagatac taaggattat cttggacat gtactgcagc    5100 ttcttgtctc tgttttggat tactggaata cccatgggcc ctctcaagag tgctggactt   5160
ctaggacatt aagatgattg tcagtacatt aaacttttca atcccattat gcaatcttgt   5220
ttgtaaatgt aaacttctaa aaatatggtt aataacattc aacctgttta ttacaactta   5280
aaaggaactt cagtgaattt gttttttattt tttaacaaga tttgtgaact gaatatcatg   5340
aaccatgttt tgatacccct ttttcacgtt gtgccaacgg aatagggtgt tgatatttc    5400 ttcatatgtt aaggagatgc ttcaaaatgt caattgcttt aaacttaaat tacctctcaa   5460
gagaccaagg tacatttacc tcattgtgta tataatgttc aatatttgtc agagcattct   5520
ccaggtttgc agttttattt ctataaagta tgggtattat gttgctcagt tactcaaatg   5580
gtactgtatt gttatatttt gtaccccaaa taacatcgtc tgtactttct gttttctgta   5640
ttgtatttgt gcaggattct ttaggcttta tcagtgtaat ctctgccttt taagatatgt   5700
acagaaaatg tccatataaa tttccattga agtcgaatga tactgagaag cctgtaaaga   5760
ggagaaaaaa acataagctg tgtttccca taagtttttt taaattgtat attgtatttg    5820
```

```
tagtaatatt ccaaaagaat gtaaatagga aatagaagag tgatgcttat gttaagtcct    5880
aacactacag tagaagaatg gaagcagtgc aaataaatta cattttttccc aagtgccagt    5940 ggcatatttt aaaataaagt gtatacgttg gaatgagtca tgccatatgt agttgctgta    6000
gatggcaact agaaccttttg agttacaaga gtctttagaa gttttctaac cctgcctagt    6060
gcaagttaca atattatagc gtgttcgggg agtgccctcc tgtctgcagg tgtgtctctg    6120
tgcctggggg cttttctcca catgcttagg ggtgtgggtc ttccattggg gcatgatgga    6180
cctgtctaca ggtgatctct gttgcctttg ggtcagcaca tttgttagtc tcctgggggt    6240
gaaaacttgg cttacaagag aactggaaaa atgatgagat gtggtcccca aaccccttgat    6300 tgactctggg gaggggcttt tgaataggga ttgctctcac attaaagata gttacttcaa    6360
tttgaaggct ggatttaggg atttttttttt ttccttataa caaagacatc accaggatat    6420 gaagctttttg ttgaaagttg gaaaaaaagt gaaattaaag acattcccag acaaa         6475
```

<210> SEQ ID NO 42
<211> LENGTH: 503
<212> TYPE: PRT
<213> ORGANISM: Homo sapiens

<400> SEQUENCE: 42

```
Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
    210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255
```

```
Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
    290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Lys Asn Gly Thr Cys Cys Ile Ala Asp Leu
            340                 345                 350

Gly Leu Ala Val Arg His Asp Ser Ala Thr Asp Thr Ile Asp Ile Ala
        355                 360                 365

Pro Asn His Arg Val Gly Thr Lys Arg Tyr Met Ala Pro Glu Val Leu
    370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
        435                 440                 445

Lys Leu Arg Pro Asn Ile Pro Asn Arg Trp Gln Ser Cys Glu Ala Leu
    450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
            500

<210> SEQ ID NO 43
<211> LENGTH: 1542
<212> TYPE: DNA
<213> ORGANISM: Homo sapiens

<400> SEQUENCE: 43
acaattactc tacagctcag aacaccaact gctgaggctg ccttgggaag aggatgatcc      60
taaacaaagc tctgctgctg ggggccctcg ctctgaccac cgtgatgagc ccctgtggag     120
gtgaagacat tgtggctgac cacgttgcct cttgtggtgt aaacttgtac cagtttttacg    180 gtccctctgg ccagtacacc catgaatttg atggagatga gcagttctac gtggacctgg     240
agaggaagga gactgcctgg cggtggcctg agttcagcaa atttggaggt tttgaccccg     300
agggtgcact gagaaacatg gctgtggcaa acacaacttt gaacatcatg attaaacgct     360
acaactctac cgctgctacc aatgaggttc tgaggtcac agtgttttcc aagtctcccg     420
tgacactggg tcagcccaac ccctcatttt gtcttgtgga caacatcttt cctcctgtgg     480
tcaacatcac atggctgagc aatgggcagt cagtcacaga aggtgtttct gagaccagct     540
tcctctccaa gagtgatcat tccttcttca agatcagtta cctcaccttc ctcccttctg     600
ctgatgagat ttatgactgc aaggtggagc actgggccct ggaccagcct cttctgaaac     660
actgggagcc tgagattcca gcccctatgt cagagctcac agagactgtg gtctgtgccc     720
```

```
tggggttgtc tgtgggcctc atgggcattg tggtgggcac tgtcttcatc atccaaggcc    780
tgcgttcagt tggtgcttcc agacaccaag ggccattgtg aatcccatcc tggaagggaa    840
ggtgcatcgc catctacagg agcagaagaa tggacttgct aaatgaccta gcactattct    900
ctggcccgat ttatcatatc ccttttctcc tccaaatatt tctcctctca ccttttctct    960
gggacttaag ctgctatatc ccctcagagc tcacaaatgc ctttacattc tttccctgac   1020
ctcctgattt tttttttctt ttctcaaatg ttacctacaa agacatgcct ggggtaagcc   1080
acccggctac ctaattcctc agtaacctcc atctaaaatc tccaaggaag caataaattc   1140
cttttatgag atctatgtca aatttttcca tctttcatcc agggctgact gaaactatgg   1200
ctaataattg gggtactctt atgtttcaat ccaatttaac ctcatttccc agatcatttt   1260
tcatgtccag taacacagaa gccaccaagt acagtatagc ctgataatat gttgatttct   1320
tagctgacat taatatttct tgcttccttg tgttcccacc cttggcactg ccacccaccc   1380
ctcaattcag gcaacaatga aattaatgga taccgtctgc ccttggccca gaattgttat   1440
agcaaaaatt ttagaaccaa aaaataagtc tgtactaatt tcaatgtggc ttttaaaagt   1500
atgacagaga aataagttag gataaaggaa atttgaatct ca                      1542
```

<210> SEQ ID NO 44
<211> LENGTH: 255
<212> TYPE: PRT
<213> ORGANISM: Homo sapiens

<400> SEQUENCE: 44

```
Met Ile Leu Asn Lys Ala Leu Leu Gly Ala Leu Ala Leu Thr Thr
1               5                  10                  15

Val Met Ser Pro Cys Gly Gly Glu Asp Ile Val Ala Asp His Val Ala
            20                  25                  30

Ser Cys Gly Val Asn Leu Tyr Gln Phe Tyr Gly Pro Ser Gly Gln Tyr
        35                  40                  45

Thr His Glu Phe Asp Gly Asp Glu Gln Phe Tyr Val Asp Leu Glu Arg
    50                  55                  60

Lys Glu Thr Ala Trp Arg Trp Pro Glu Phe Ser Lys Phe Gly Gly Phe
65                  70                  75                  80

Asp Pro Gln Gly Ala Leu Arg Asn Met Ala Val Ala Lys His Asn Leu
                85                  90                  95

Asn Ile Met Ile Lys Arg Tyr Asn Ser Thr Ala Ala Thr Asn Glu Val
            100                 105                 110

Pro Glu Val Thr Val Phe Ser Lys Ser Pro Val Thr Leu Gly Gln Pro
        115                 120                 125

Asn Thr Leu Ile Cys Leu Val Asp Asn Ile Phe Pro Pro Val Val Asn
    130                 135                 140

Ile Thr Trp Leu Ser Asn Gly Gln Ser Val Thr Glu Gly Val Ser Glu
145                 150                 155                 160

Thr Ser Phe Leu Ser Lys Ser Asp His Ser Phe Phe Lys Ile Ser Tyr
                165                 170                 175

Leu Thr Phe Leu Pro Ser Ala Asp Glu Ile Tyr Asp Cys Lys Val Glu
            180                 185                 190

His Trp Gly Leu Asp Gln Pro Leu Leu Lys His Trp Glu Pro Glu Ile
        195                 200                 205

Pro Ala Pro Met Ser Glu Leu Thr Glu Thr Val Val Cys Ala Leu Gly
    210                 215                 220
```

Leu Ser Val Gly Leu Met Gly Ile Val Val Gly Thr Val Phe Ile Ile
225                 230                 235                 240

Gln Gly Leu Arg Ser Val Gly Ala Ser Arg His Gln Gly Pro Leu
                245                 250                 255

<210> SEQ ID NO 45
<211> LENGTH: 2527
<212> TYPE: DNA
<213> ORGANISM: Homo sapiens

<400> SEQUENCE: 45

| | | | | |
|---|---|---|---|---|
| ctcaagctcc | tctacaaaga | ggtggacaga | gaagacagca | gagaccatgg gaccccctc | 60 |
| agcccctccc | tgcagattgc | atgtccctg | gaaggaggtc | ctgctcacag cctcacttct | 120 |
| aaccttctgg | aacccaccca | ccactgccaa | gctcactatt | gaatccacgc cattcaatgt | 180 |
| cgcagagggg | aaggaggttc | ttctactcgc | ccacaacctg | ccccagaatc gtattggtta | 240 |
| cagctggtac | aaaggcgaaa | gagtggatgg | caacagtcta | attgtaggat atgtaatagg | 300 |
| aactcaacaa | gctacccag | ggccgcata | cagtggtcga | gagacaatat accccaatgc | 360 |
| atccctgctg | atccagaacg | tcacccgaa | tgacacagga | ttctataccc tacaagtcat | 420 |
| aaagtcagat | cttgtgaatg | aagaagcaac | cggacagttc | catgtatacc cggagctgcc | 480 |
| caagccctcc | atctccagca | caactccaa | cccgtggag | acaaggatg ctgtggcctt | 540 |
| cacctgtgaa | cctgaggttc | agaacacaac | ctacctgtgg | tgggtaaatg gtcagagcct | 600 |
| cccggtcagt | cccaggctgc | agctgtccaa | tggcaacatg | accctcactc tactcagcgt | 660 |
| caaaaggaac | gatgcaggat | cctatgaatg | tgaaatacag | aacccagcga gtgccaaccg | 720 |
| cagtgaccca | gtcaccctga | atgtcctcta | tgggcccag | tggcccacca tttccccctc | 780 |
| aaaggccaat | taccgtccag | gggaaaatct | gaacctctcc | tgccacgcag cctctaaccc | 840 |
| acctgcacag | tactcttggt | ttatcaatgg | gacgttccag | caatccacac aagagctctt | 900 |
| tatcccccaac | atcactgtga | ataatagcgg | atcctatatg | tgccaagccc ataactcagc | 960 |
| cactggcctc | aataggacca | cagtcacgat | gatcacagtc | tctggaagtg ctcctgtcct | 1020 |
| ctcagctgtg | gccaccgtcg | gcatcacgat | tggagtgctg | gccagggtcg ctctgatata | 1080 |
| gcagccctgg | tgtattttcg | atatttcagg | aagactggca | gattggacca gaccctgaat | 1140 |
| tcttctagct | cctccaatcc | cattttatcc | atggaaccac | taaaaacaag gtctgctctg | 1200 |
| ctcctgaagc | cctatatgct | ggagatggac | aactcaatga | aaatttaaag ggaaaaccct | 1260 |
| caggcctgag | gtgtgtgcca | ctcagagact | tcacctaact | agacacaggc aaactgcaaa | 1320 |
| ccatggtgag | aaattgacga | cttcacacta | tggacagctt | ttcccaagat gtcaaaacaa | 1380 |
| gactcctcat | catgataagg | ctcttacccc | cttttaattt | gtccttgctt atgcctgcct | 1440 |
| ctttcgcttg | gcaggatgat | gctgtcatta | gtattcacaa | gaagtagctt cagagggtaa | 1500 |
| cttaacagag | tatcagattc | tatccttgtca | atcccaacgt | tttacataaa ataagagatc | 1560 |
| ctttagtgca | cccagtgact | gacattagca | gcatctttaa | cacagccgtg tgttcaaatg | 1620 |
| tacagtggtc | ctttttcagag | ttggacttct | agactcacct | gttctcactc cctgttttaa | 1680 |
| tttcaaccca | gccatgcaat | gccaaataat | agaattgctc | cctaccagct gaacagggag | 1740 |
| gagtctgtgc | agtttctgac | acttgttgtt | gaacatggct | aaatacaatg ggtatcgctg | 1800 |
| agactaagtt | gtagaaatta | acaaatgtgc | tgctggtaaa | atggctacac tcatctgact | 1860 |
| cattctttat | tctattttag | ttggtttgta | tcttgcctaa | ggtgcgtagt ccaactcttg | 1920 |
| gtattaccct | cctaatagtc | atactagtag | tcatactccc | tggtgtagtg tattctctaa | 1980 |

```
aagctttaaa tgtctgcatg cagccagcca tcaaatagtg aatggtctct ctttggctgg    2040
aattacaaaa ctcagagaaa tgtgtcatca ggagaacatc ataacccatg aaggataaaa    2100
gccccaaatg gtggtaactg ataatagcac taatgcttaa gatttggtca cactctctca    2160
cctaggtgag cgcattgagc cagtggtgct aaatgctaca tactccaact gaaatgttaa    2220
ggaagaagat agatccaatt aaaaaaaatt aaaaccaatt taaaaaaaaa aagaacacag    2280
gagattccag tctacttgag ttagcataat acagaagtcc cctctacttt aacttttaca    2340
aaaaagtaac ctgaactaat ctgatgttaa ccaatgtatt tatttctgtg gttctgtttc    2400
cttgttccaa tttgacaaaa cccactgttc ttgtattgta ttgccagggg ggagctatca    2460
ctgtacttgt agagtggtgc tgctttaatt cataaatcac aaataaaagc caattagctc    2520
tataact                                                              2527

<210> SEQ ID NO 46
<211> LENGTH: 344
<212> TYPE: PRT
<213> ORGANISM: Homo sapiens

<400> SEQUENCE: 46

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
            260                 265                 270
```

```
Ile Asn Gly Thr Phe Gln Gln Ser Thr Gln Glu Leu Phe Ile Pro Asn
            275                 280                 285

Ile Thr Val Asn Asn Ser Gly Ser Tyr Met Cys Gln Ala His Asn Ser
            290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340

<210> SEQ ID NO 47
<211> LENGTH: 2592
<212> TYPE: DNA
<213> ORGANISM: Homo sapiens

<400> SEQUENCE: 47
aaaaagcagc agaacctgga agtccacggg gagcttggat gccaaaggga ggacggctgg      60
gtcctctgga gaggactact cactggcata tttctgaggt atctgtagaa aaccacagcc     120
tcagatactg ggactttac  agtcccacag aaccgtcctc ccaggaagct gaattcagca     180
agaacaatgg aggccagcgg gaagctcatt tgcagacaaa ggcaagtcct ttttttcctttt   240
ctccttttgg gcttatctct ggcgggcgcg gcggaaccta aagctattc  tgtggtggag     300
gaaactgagg gcagctcctt tgtcaccaat ttagcaaagg acctgggtct ggagcagagg     360
gaattctcca ggcgggggt  tagggttgtt ccagaggga  acaaactaca tttgcagctc     420
aatcaggaga ccgcggattt gttgctaaat gagaaattgg accgtgagga tctgtgcggt     480
cacacagagc cctgtgtgct acgtttccaa gtgttgctag agagtccctt cgagttttt     540
caagctgagc tgcaagtaat agacataaac gaccactctc cagtatttct ggacaaacaa     600
atgttggtga agtatcaga  gagcagtcct cctgggactg cgtttcctct gaagaatgct     660
gaagacttag atataggcca aaacaatatt gagaactata taatcagccc caactcctat     720
tttcgggtcc tcacccgcaa acgcagtgat ggcaggaaat acccagagct ggtgctggac     780
aacgcgctgg accgagagga agaagctgag ctcaggttaa cactcacagc actggatggt     840
ggctctccgc ccagatctgg cactgctcag gtctacattg aagttgtcga tgtcaatgat     900
aatgccctg  aatttcagca gccttttcta  t agggtgcaga tctctgagga cagtccaata    960
agcttcctgg ttgtgaaggt ctctgccacg gatgtagaca caggagtcaa cggagagatt    1020
tcctattcac ttttccaagc ttcagatgag ataagcaaaa cttttaaggt cgatttcttg    1080
acaggagaaa ttcgactaaa gaacaactt  gatttcgaaa aatttcagtc ctatgaagtc    1140
aatatcgagg cgagagatgc tggaggcttt tctggaaaat gcaccgttct gattcaagtg    1200
atagatgtga acgaccatgc cccagaagtt accatgtctg catttaccag cccaatacct    1260
gagaatgcgc ctgaaactgt ggttgcactt tcagtgttt  cagaccttga ttcaggagaa    1320
aatgggaaaa taagttgctc cattcaggag gatctaccct tcctcctgaa atcttctgtg    1380
gggaacttt  acaccctact aacagagaca ccactagaca gagaaagcag agccgagtac    1440
aacgtcacta tcaccgtcac tgacttaggg acacccagc tgacaacaca tctcaatatg    1500
accgtgctgg tgtcggacgt caatgacaac gccccgcct  tcacccaaac ctcctacacc    1560
ctgttcgtcc gcgagaacaa cagccccgcc ctgcacatcg cagcgtcag  cgccacagac    1620
agagactcgg gcaccaacgc ccaggtcacc tactcgctgc tgccgcccca ggatccgcac    1680
```

-continued

```
ctgcccctcg cctccctggt ctccatcaac acagacaacg gccacctgtt cgccctcagg  1740
tcgctggact acgaggccct gcaggcgttc gagttccggg tgggcgcttc agaccgcggc  1800
tccccggctt tgagcagcga ggcgctggtg cgcgtgctgg tgctggacgc caacgacaac  1860
tcgcccttcg tgctgtaccc gctgcagaat ggctccgcgc cctgcaccga gctggtgccc  1920
cgggcggccg agccgggcta cctggtgacc aaggtggtgg cggtgacggc gactcgggc   1980 cagaacgcct ggctgtcgta ccagctgctc aaggccacgg agcccgggct gttcggtgtg  2040
tgggcgcaca atggcgaggt gcgcaccgcc aggctgctga gcgagcgcga cgcggccaag  2100
cagaggctgg tggtgctggt caaggacaat ggcgagcctc cgtgctcggc caccgccacg  2160
ctgcacttgc tcctggtgga cggcttctcc cagccctacc tgccgcttcc ggaggctgcc  2220
ccagcccagg gccaggccga ctctctcacc gtctacctgg tggtggcgtt ggcctcggtg  2280
tcttcgctct tcctcttctc ggtgctcctg ttcgtggcgg tgctgctgtg taggaggagc  2340
agggcggcct cggtgggtcg ctgctcagtg cctgagggcc cctttccagg gcatctggtg  2400
gacgtgaggg gcaccgggag cctgtctcag aactatcagt acgaggtgtg cctggcagga  2460
ggctcaggga cgaatgagtt ccagttcctg aaaccagtat tacctaatat tcagggccat  2520
tcttttgggc cagaaatgga acaaaactct aactttagga atggctttgg tttcagcctt  2580
cagttaaagt aa                                                      2592
```

<210> SEQ ID NO 48
<211> LENGTH: 801
<212> TYPE: PRT
<213> ORGANISM: Homo sapiens

<400> SEQUENCE: 48

Met Glu Ala Ser Gly Lys Leu Ile Cys Arg Gln Arg Gln Val Leu Phe
1               5                   10                  15

Ser Phe Leu Leu Gly Leu Ser Leu Ala Gly Ala Ala Glu Pro Arg
            20                  25                  30

Ser Tyr Ser Val Val Glu Glu Thr Glu Gly Ser Ser Phe Val Thr Asn
        35                  40                  45

Leu Ala Lys Asp Leu Gly Leu Glu Gln Arg Glu Phe Ser Arg Arg Gly
    50                  55                  60

Val Arg Val Val Ser Arg Gly Asn Lys Leu His Leu Gln Leu Asn Gln
65                  70                  75                  80

Glu Thr Ala Asp Leu Leu Leu Asn Glu Lys Leu Asp Arg Glu Asp Leu
                85                  90                  95

Cys Gly His Thr Glu Pro Cys Val Leu Arg Phe Gln Val Leu Leu Glu
            100                 105                 110

Ser Pro Phe Glu Phe Phe Gln Ala Glu Leu Gln Val Ile Asp Ile Asn
        115                 120                 125

Asp His Ser Pro Val Phe Leu Asp Lys Gln Met Leu Val Lys Val Ser
    130                 135                 140

Glu Ser Ser Pro Gly Thr Ala Phe Pro Leu Lys Asn Ala Glu Asp
145                 150                 155                 160

Leu Asp Ile Gly Gln Asn Asn Ile Glu Asn Tyr Ile Ile Ser Pro Asn
                165                 170                 175

Ser Tyr Phe Arg Val Leu Thr Arg Lys Arg Ser Asp Gly Arg Lys Tyr
            180                 185                 190

Pro Glu Leu Val Leu Asp Asn Ala Leu Asp Arg Glu Glu Glu Ala Glu
        195                 200                 205

-continued

```
Leu Arg Leu Thr Leu Thr Ala Leu Asp Gly Gly Ser Pro Arg Ser
    210                 215                 220
Gly Thr Ala Gln Val Tyr Ile Glu Val Val Asp Val Asn Asp Asn Ala
225                 230                 235                 240
Pro Glu Phe Gln Gln Pro Phe Tyr Arg Val Gln Ile Ser Glu Asp Ser
                245                 250                 255
Pro Ile Ser Phe Leu Val Val Lys Val Ser Ala Thr Asp Val Asp Thr
            260                 265                 270
Gly Val Asn Gly Glu Ile Ser Tyr Ser Leu Phe Gln Ala Ser Asp Glu
        275                 280                 285
Ile Ser Lys Thr Phe Lys Val Asp Phe Leu Thr Gly Glu Ile Arg Leu
    290                 295                 300
Lys Lys Gln Leu Asp Phe Glu Lys Phe Gln Ser Tyr Glu Val Asn Ile
305                 310                 315                 320
Glu Ala Arg Asp Ala Gly Gly Phe Ser Gly Lys Cys Thr Val Leu Ile
                325                 330                 335
Gln Val Ile Asp Val Asn Asp His Ala Pro Glu Val Thr Met Ser Ala
            340                 345                 350
Phe Thr Ser Pro Ile Pro Glu Asn Ala Pro Glu Thr Val Val Ala Leu
        355                 360                 365
Phe Ser Val Ser Asp Leu Asp Ser Gly Glu Asn Gly Lys Ile Ser Cys
    370                 375                 380
Ser Ile Gln Glu Asp Leu Pro Phe Leu Leu Lys Ser Ser Val Gly Asn
385                 390                 395                 400
Phe Tyr Thr Leu Leu Thr Glu Thr Pro Leu Asp Arg Glu Ser Arg Ala
                405                 410                 415
Glu Tyr Asn Val Thr Ile Thr Val Thr Asp Leu Gly Thr Pro Arg Leu
            420                 425                 430
Thr Thr His Leu Asn Met Thr Val Leu Val Ser Asp Val Asn Asp Asn
        435                 440                 445
Ala Pro Ala Phe Thr Gln Thr Ser Tyr Thr Leu Phe Val Arg Glu Asn
    450                 455                 460
Asn Ser Pro Ala Leu His Ile Gly Ser Val Ser Ala Thr Asp Arg Asp
465                 470                 475                 480
Ser Gly Thr Asn Ala Gln Val Thr Tyr Ser Leu Leu Pro Pro Gln Asp
                485                 490                 495
Pro His Leu Pro Leu Ala Ser Leu Val Ser Ile Asn Thr Asp Asn Gly
            500                 505                 510
His Leu Phe Ala Leu Arg Ser Leu Asp Tyr Glu Ala Leu Gln Ala Phe
        515                 520                 525
Glu Phe Arg Val Gly Ala Ser Asp Arg Gly Ser Pro Ala Leu Ser Ser
    530                 535                 540
Glu Ala Leu Val Arg Val Leu Val Leu Asp Ala Asn Asp Asn Ser Pro
545                 550                 555                 560
Phe Val Leu Tyr Pro Leu Gln Asn Gly Ser Ala Pro Cys Thr Glu Leu
                565                 570                 575
Val Pro Arg Ala Ala Glu Pro Gly Tyr Leu Val Thr Lys Val Val Ala
            580                 585                 590
Val Asp Gly Asp Ser Gly Gln Asn Ala Trp Leu Ser Tyr Gln Leu Leu
        595                 600                 605
Lys Ala Thr Glu Pro Gly Leu Phe Gly Val Trp Ala His Asn Gly Glu
    610                 615                 620
```

-continued

Val Arg Thr Ala Arg Leu Leu Ser Glu Arg Asp Ala Ala Lys Gln Arg
625                 630                 635                 640

Leu Val Val Leu Val Lys Asp Asn Gly Glu Pro Pro Cys Ser Ala Thr
            645                 650                 655

Ala Thr Leu His Leu Leu Leu Val Asp Gly Phe Ser Gln Pro Tyr Leu
                660                 665                 670

Pro Leu Pro Glu Ala Ala Pro Ala Gln Gly Gln Ala Asp Ser Leu Thr
            675                 680                 685

Val Tyr Leu Val Val Ala Leu Ala Ser Val Ser Ser Leu Phe Leu Phe
    690                 695                 700

Ser Val Leu Leu Phe Val Ala Val Leu Leu Cys Arg Arg Ser Arg Ala
705                 710                 715                 720

Ala Ser Val Gly Arg Cys Ser Val Pro Glu Gly Pro Phe Pro Gly His
                725                 730                 735

Leu Val Asp Val Arg Gly Thr Gly Ser Leu Ser Gln Asn Tyr Gln Tyr
                740                 745                 750

Glu Val Cys Leu Ala Gly Gly Ser Gly Thr Asn Glu Phe Gln Phe Leu
            755                 760                 765

Lys Pro Val Leu Pro Asn Ile Gln Gly His Ser Phe Gly Pro Glu Met
770                 775                 780

Glu Gln Asn Ser Asn Phe Arg Asn Gly Phe Gly Phe Ser Leu Gln Leu
785                 790                 795                 800

Lys

<210> SEQ ID NO 49
<211> LENGTH: 4220
<212> TYPE: DNA
<213> ORGANISM: Homo sapiens

<400> SEQUENCE: 49

| | | | | | |
|---|---|---|---|---|---|
| atgaagacca | gggggttcag | ctttccaaga | caaaggcaag | tcctgtttct | ttttcttttc | 60 |
| tggggagtgt | ccttggcagg | ttctgggttt | ggacgttatt | cggtgactga | ggaaacagag | 120 |
| aaaggatcct | tgtggtcaa | tctggcaaag | gatctgggac | tagcagaggg | ggagctggct | 180 |
| gcaaggggaa | ccagggtggt | ttccgatgat | aacaaacaat | acctgctcct | ggattcacat | 240 |
| accgggaatt | gctcacaaaa | tgagaaactg | accgagaga | agctgtgtgg | ccctaaagag | 300 |
| ccctgtatgc | tgtatttcca | aattttaatg | gatgatccct | ttcagattta | ccgggctgag | 360 |
| ctgagagtca | gggatataaa | tgatcactcg | ccagtgtttc | ggcacaaaga | gatggtctta | 420 |
| aaaatatcag | aaaatacagc | tgaagggaca | gcatttagac | tagaaagagc | acaggatcca | 480 |
| gatgaaggtc | ataacagtat | ccaaaactac | acgatcagct | ccaactcttt | tttccatatt | 540 |
| aaaattagtg | gcagtgatga | aggcatgata | tatccagagc | tagtgttgga | caaagcactg | 600 |
| gatcgggagg | agcaggaaga | gctcagctta | accctcacag | cgctggatgg | tgggtctcca | 660 |
| tccaggtctg | ggacctccac | tatacgcatt | gtggtcttgg | atgtcaatga | caatgcccca | 720 |
| cagtttgccc | aggctctgta | tgagacccag | gctccagaaa | acagtccagt | agggtccctt | 780 |
| attgttaaag | tgtctgcagg | agatgcagac | tcaggagtca | atgcagaagt | atcctattca | 840 |
| ttttttgatg | cttctgaaga | tattttaaca | acgtttcaaa | tcaatccttt | ttctggggaa | 900 |
| atctttctca | gagaattgct | tgattatgag | ttagtaaatt | cttacaaaat | aaatatacag | 960 |
| gcaatggacg | gcggaggcct | ttctgcaaga | tgtacagttt | tgataaaagt | attagattcc | 1020 |
| aatgacaatc | tccctgaact | gatcatatca | tcactttcca | actctgttgc | tgaaaactct | 1080 |

-continued

```
cctgggatag tattggctgt ttttaagatt aaagacagag actccggaga aaatggaaag    1140
acaatttgct atgttcaaga taatctgcct tttttttctga aaccgtctgt tgacaatttt    1200
tacatcctaa tgactgaagg tgcactggac agagagagca aagctgagta caacatcacc    1260
atcaccgtca ctgacttggg gacacccagg ctgaaaaccg agcacagcat aaccctgcag    1320
gtctccgacg tcaatgacaa cgcccccgcc ttcacccaaa cctcctacac cctgttcgtc    1380
cgggagaaca acagccccgc cctgcacatc ggcagtgtca cgccacaga cagagactca    1440 ggcaccaacg cccaggtcac ctactcgctg ctgccgcccc aggacccaca cctgcccctc    1500
gcctccctgg tctccatcaa cgcggacaat ggccacctgt tgccctcag gtcgctggac    1560 tacgaggccc tgcaggcttt cgacttccgc gtgggcgcct cagaccgcgg ctccccggct    1620
ttgagcagcg aggcgctggt gcgcgtactg gtgctgacg ccaacgacaa ctcgcccttc    1680
gtgctgtacc cgctgcagaa cggctccgcg ccctgcaccg agctggtgcc ccgggcggcc    1740
gagccgggct acctggtgac caaggtggtg gcggtggacg gcgactcggg ccagaacgcc    1800
tggctgtcgt accagctgct caaggccacg gagcccgggc tgttcggtgt gtgggcgcac    1860
aatggggagg tgcgcaccgc caggctgctg agcgagcgcg acgcggccaa gcacaggctg    1920
gtggtgcttg tcaaggacaa tggcgagcct cctcgctcgg ccaccgccac gctgcacgtg    1980
ctcctggtgg acggcttctc ccagcccttac ctgcctctcc cggaggcggc cccggcccag    2040
gcccaggccg acttgctcac cgtctacctg gtggtggcgt tggcctcggt gtcttcgctc    2100
ttcctcctct cggtgctcct gttcgtggcg gtgcggctgt gcaggaggag cagggcggcc    2160
tcggtgggtc gctgctcggt gcccgagggt ccttttccag ggcatctggt ggacgtgagc    2220
ggcaccggga ccctgttcca gagctaccag tacgaggtgt gtctgactgg aggttcagag    2280
accggcgagt tcaagttctt gaagccgatt accccccacc tcccgcccca tagggggtggg    2340 aaagaaatag aggaaaattc tactctcccc aatagctttg gatttaatta ttgaaaggaa    2400
cccacttaat aaagacattt acttctttaa tatattcttg ttggctaact aaattgtgta    2460
tgcccaccac aaagaaggta ctattttttg tttgattcat cttcaactttt gcgtattatg    2520 cttaacttca caagttaact ttttcttatt ttgtatcctg atgaggcatt tcttactaga    2580
atcccataag tgaaatataa tatttttcaa agttgatatc atttaaaaat ttttggtcgt    2640
tttaaatgtc tttattgact ttaaattcat tgcctctaca ttattcatta gttcttcttt    2700
tcctaaaact ttttacttgt taaaatagtc tgctgcatgt aatatgtgct tttactatttt    2760 gatatttctt ctattttttct tttgaaaccg gtgttcttat tggtttgcca tccttgttca    2820
ttacaactgt tttttgtttg tttgtttgtt ttttggtttg tttgtttttt ttttttttga    2880
gacggagtct cgctctgtcg cccaggctgg agtgcagtgg cgcgatctca gctcactgca    2940
acctccgcct cccaggttca agcgattctc ctgcctcagc ctccagagta tctgggacta    3000
cagttgcatg tcaccacgtt cggctaattt ttgtatttttc agtagagacg ggtttcatca    3060
tggtggccag gatggtctat ctcttgacct cgtgatccac cccactcagc ctcccaaatt    3120
gctgggattt acaggcatga gccaccgcac ccagcctaca ataattttct taaactttac    3180
cttttatttt aaagttctag ttttcccggca ttgatagttc cctatttgaa atataatgtt    3240
tctcttgtaa gtgatatgat aaataaaccc ctaattagcc ttagaagaaa aaccactgca    3300
agatattaag cgtgtgtaaa tgggctttag tctggaaacc aaaaaaaaaa aaaaattta    3360 gtcattctat aggatcatgt gaaaatattt aatttgctcc ttttaattct gtataaacaa    3420
atcagaggtt cctgaggttc ctgttaaatt tttaatggct aatagcccag tgccatccag    3480
```

-continued

```
ttgaaaaaac aacagcaatc acaaagtaga ggtttatatt gtgcggcttt tatattcagc    3540
tattagagtg ttattggtag tgtctagcct tttcctccac gacattcctt gacttaatcc    3600
atttgggcct attatagaca aaatagagct tctttctaga tataaggtct ttgaggcagg    3660
gctcagtggc tcattcctgt aatcccagca ctttgggagg ccaaggcggg cagatcacct    3720
taggtcacga gtttgagacc agcctgacca acgttaagta accccgtctt tactaaaaat    3780
acaaaattag ccaggcatgg tggcacatgc ttgtaatccc agctactcgg gaggctgagg    3840
caggagaatc gcttgaaccc aggaggtgga agttgctttg agccgagatt gcaccattgt    3900
actccagcct gggcaataag agcaaaactc catcaaaata aaataaaata aaatataaaa    3960
taacttaaaa agaactttga ataaaattct atgaaaaaag acactagaat gctgttctta    4020
attttaatag tgttaagata ggtgttagtg tggtctgttc tttacctccc tttatttggt    4080
gcagagaagt tagatcctgc taaatttcaa ttaagagggg accttaaaat aaggatcaat    4140
ctcttattta accctgtaag ttactttaaa gctaatacaa gaaaacaaa gacaagtgaa    4200 agtaaggaaa cagaaattgc                                                4220
```

<210> SEQ ID NO 50
<211> LENGTH: 797
<212> TYPE: PRT
<213> ORGANISM: Homo sapiens

<400> SEQUENCE: 50

```
Met Lys Thr Arg Gly Phe Ser Phe Pro Arg Gln Arg Gln Val Leu Phe
1               5                   10                  15

Leu Phe Leu Phe Trp Gly Val Ser Leu Ala Gly Ser Gly Phe Gly Arg
            20                  25                  30

Tyr Ser Val Thr Glu Glu Thr Glu Lys Gly Ser Phe Val Val Asn Leu
        35                  40                  45

Ala Lys Asp Leu Gly Leu Ala Glu Gly Glu Leu Ala Ala Arg Gly Thr
    50                  55                  60

Arg Val Val Ser Asp Asp Asn Lys Gln Tyr Leu Leu Leu Asp Ser His
65                  70                  75                  80

Thr Gly Asn Leu Leu Thr Asn Glu Lys Leu Asp Arg Glu Lys Leu Cys
                85                  90                  95

Gly Pro Lys Glu Pro Cys Met Leu Tyr Phe Gln Ile Leu Met Asp Asp
            100                 105                 110

Pro Phe Gln Ile Tyr Arg Ala Glu Leu Arg Val Arg Asp Ile Asn Asp
        115                 120                 125

His Ser Pro Val Phe Arg His Lys Glu Met Val Leu Lys Ile Ser Glu
    130                 135                 140

Asn Thr Ala Glu Gly Thr Ala Phe Arg Leu Glu Arg Ala Gln Asp Pro
145                 150                 155                 160

Asp Glu Gly His Asn Ser Ile Gln Asn Tyr Thr Ile Ser Ser Asn Ser
                165                 170                 175

Phe Phe His Ile Lys Ile Ser Gly Ser Asp Glu Gly Met Ile Tyr Pro
            180                 185                 190

Glu Leu Val Leu Asp Lys Ala Leu Asp Arg Glu Gln Gln Glu Glu Leu
        195                 200                 205

Ser Leu Thr Leu Thr Ala Leu Asp Gly Gly Ser Pro Ser Arg Ser Gly
    210                 215                 220

Thr Ser Thr Ile Arg Ile Val Val Leu Asp Val Asn Asp Asn Ala Pro
225                 230                 235                 240
```

-continued

```
Gln Phe Ala Gln Ala Leu Tyr Glu Thr Gln Ala Pro Glu Asn Ser Pro
                245                 250                 255

Val Gly Ser Leu Ile Val Lys Val Ser Ala Gly Asp Ala Asp Ser Gly
            260                 265                 270

Val Asn Ala Glu Val Ser Tyr Ser Phe Phe Asp Ala Ser Glu Asp Ile
        275                 280                 285

Leu Thr Thr Phe Gln Ile Asn Pro Phe Ser Gly Glu Ile Phe Leu Arg
    290                 295                 300

Glu Leu Leu Asp Tyr Glu Leu Val Asn Ser Tyr Lys Ile Asn Ile Gln
305                 310                 315                 320

Ala Met Asp Gly Gly Gly Leu Ser Ala Arg Cys Thr Val Leu Ile Lys
                325                 330                 335

Val Leu Asp Ser Asn Asp Asn Pro Glu Leu Ile Ile Ser Ser Leu
            340                 345                 350

Ser Asn Ser Val Ala Glu Asn Ser Pro Gly Ile Val Leu Ala Val Phe
            355                 360                 365

Lys Ile Lys Asp Arg Asp Ser Gly Glu Asn Gly Lys Thr Ile Cys Tyr
    370                 375                 380

Val Gln Asp Asn Leu Pro Phe Phe Leu Lys Pro Ser Val Asp Asn Phe
385                 390                 395                 400

Tyr Ile Leu Met Thr Glu Gly Ala Leu Asp Arg Glu Ser Lys Ala Glu
                405                 410                 415

Tyr Asn Ile Thr Ile Thr Val Thr Asp Leu Gly Thr Pro Arg Leu Lys
            420                 425                 430

Thr Glu His Ser Ile Thr Leu Gln Val Ser Asp Val Asn Asp Asn Ala
        435                 440                 445

Pro Ala Phe Thr Gln Thr Ser Tyr Thr Leu Phe Val Arg Glu Asn Asn
    450                 455                 460

Ser Pro Ala Leu His Ile Gly Ser Val Ser Ala Thr Asp Arg Asp Ser
465                 470                 475                 480

Gly Thr Asn Ala Gln Val Thr Tyr Ser Leu Leu Pro Pro Gln Asp Pro
                485                 490                 495

His Leu Pro Leu Ala Ser Leu Val Ser Ile Asn Ala Asp Asn Gly His
            500                 505                 510

Leu Phe Ala Leu Arg Ser Leu Asp Tyr Glu Ala Leu Gln Ala Phe Asp
        515                 520                 525

Phe Arg Val Gly Ala Ser Asp Arg Gly Ser Pro Ala Leu Ser Ser Glu
    530                 535                 540

Ala Leu Val Arg Val Leu Val Leu Asp Ala Asn Asp Asn Ser Pro Phe
545                 550                 555                 560

Val Leu Tyr Pro Leu Gln Asn Gly Ser Ala Pro Cys Thr Glu Leu Val
                565                 570                 575

Pro Arg Ala Ala Glu Pro Gly Tyr Leu Val Thr Lys Val Val Ala Val
            580                 585                 590

Asp Gly Asp Ser Gly Gln Asn Ala Trp Leu Ser Tyr Gln Leu Leu Lys
        595                 600                 605

Ala Thr Glu Pro Gly Leu Phe Gly Val Trp Ala His Asn Gly Glu Val
    610                 615                 620

Arg Thr Ala Arg Leu Leu Ser Glu Arg Asp Ala Ala Lys His Arg Leu
625                 630                 635                 640

Val Val Leu Val Lys Asp Asn Gly Glu Pro Pro Arg Ser Ala Thr Ala
                645                 650                 655
```

-continued

```
Thr Leu His Val Leu Val Asp Gly Phe Ser Gln Pro Tyr Leu Pro
            660                 665                 670

Leu Pro Glu Ala Ala Pro Ala Gln Ala Gln Ala Asp Leu Leu Thr Val
        675                 680                 685

Tyr Leu Val Val Ala Leu Ala Ser Val Ser Ser Leu Phe Leu Leu Ser
    690                 695                 700

Val Leu Leu Phe Val Ala Val Arg Leu Cys Arg Arg Ser Arg Ala Ala
705                 710                 715                 720

Ser Val Gly Arg Cys Ser Val Pro Glu Gly Pro Phe Pro Gly His Leu
                725                 730                 735

Val Asp Val Ser Gly Thr Gly Thr Leu Phe Gln Ser Tyr Gln Tyr Glu
            740                 745                 750

Val Cys Leu Thr Gly Gly Ser Glu Thr Gly Glu Phe Lys Phe Leu Lys
        755                 760                 765

Pro Ile Thr Pro His Leu Pro Pro His Arg Gly Gly Lys Glu Ile Glu
    770                 775                 780

Glu Asn Ser Thr Leu Pro Asn Ser Phe Gly Phe Asn Tyr
785                 790                 795
```

```
<210> SEQ ID NO 51
<211> LENGTH: 19
<212> TYPE: DNA
<213> ORGANISM: Homo sapiens

<400> SEQUENCE: 51
gctgtgcatc tttgaccga                                               19

<210> SEQ ID NO 52
<211> LENGTH: 20
<212> TYPE: DNA
<213> ORGANISM: Homo sapiens

<400> SEQUENCE: 52
gaggcgtctg cttttctgaa                                              20

<210> SEQ ID NO 53
<211> LENGTH: 21
<212> TYPE: DNA
<213> ORGANISM: Homo sapiens

<400> SEQUENCE: 53
cagggtttcc tactgctgtt c                                            21

<210> SEQ ID NO 54
<211> LENGTH: 21
<212> TYPE: DNA
<213> ORGANISM: Homo sapiens

<400> SEQUENCE: 54
acaggacttg cctttgtctt g                                            21

<210> SEQ ID NO 55
<211> LENGTH: 21
<212> TYPE: DNA
<213> ORGANISM: Homo sapiens

<400> SEQUENCE: 55
aggagttgtg gatgcactaa g                                            21

<210> SEQ ID NO 56
```

```
<211> LENGTH: 22
<212> TYPE: DNA
<213> ORGANISM: Homo sapiens

<400> SEQUENCE: 56
ctgctgaaag tctgctctca ta                                          22

<210> SEQ ID NO 57
<211> LENGTH: 20
<212> TYPE: DNA
<213> ORGANISM: Homo sapiens

<400> SEQUENCE: 57
tgggagtctg gcttgttgag                                             20

<210> SEQ ID NO 58
<211> LENGTH: 23
<212> TYPE: DNA
<213> ORGANISM: Homo sapiens

<400> SEQUENCE: 58
ataatgagtg ctacggtggt acc                                         23
```

METHODS OF IDENTIFYING PANCREATIC CANCER CELLS

CROSS REFERENCE TO RELATED APPLICATION

This application claims the benefit of U.S. Provisional Patent Application No. 60/905,120.

STATEMENT REGARDING FEDERALLY SPONSORED RESEARCH

This invention was made under grants from the National Institutes of Health (R33CA959944; and R01CA97360).

BACKGROUND OF THE INVENTION

The invention relates generally to methods of identification of cell types on the basis of identification of specific targets, and more specifically to methods of identifying pancreatic cancer cells on the basis of the expression of a particular combination of specific targets.

The targeting of imaging agents or therapeutic agents to molecular targets on the surface of particular cell types holds considerable promise as a research, diagnostic and therapeutic strategy. Cell surface molecules are often favored because their structural diversity and because agents that target cell surface molecules do not need to cross the plasma membrane to reach their targets. Many targeting agents contain one or more moieties capable of specifically binding a single cell surface protein. Such agents include small molecules and monoclonal antibodies. There have been successes using this approach. In one example, a series of RGD-peptide based ligands coupled with a variety of proteins, small molecules, nucleic acids and radiotracers were developed to deliver therapeutics to tumor vasculature (see reference 18). The 18F-Galacto-RGD ligand was tested in humans and showed desirable pharmacokinetics and good visualization of $\alpha v \beta 3$-integrin expression under PET scan (see references 19 and 20). Additionally, radiolabeled monoclonal antibodies that target cell surface antigens were approved as a treatment of B-cell non-Hodgkin's lymphoma (see reference 21). However, while such monospecific (also termed monomeric or monovalent) agents have demonstrated some utility in targeting and identifying some tumors, their use is limited the rare instance in which a target is expressed at a high level on tumor relative to normal tissue. Moreover, agents capable of binding only a single cell surface target might not be specific enough to differentiate one cell type from another (in one nonlimiting example, differentiation of a tumor cell from a noncancerous cell). As a result, some monospecific agents used as therapeutics often cause substantial side effects. Similarly, only a small proportion of cell surface targets are overexpressed in solid tumors relative to normal tissues. Therefore, monospecific ligands are useful in only a small proportion of the potential cell surface targets on solid tumors.

A multispecific (also termed multimeric or multivalent) ligand, on the other hand, has multiple binding specificities per ligand. Because a multispecific ligand can bind multiple surface targets on a cell, it has a greater overall affinity and avidity to cells expressing a particular combination of targets with minimal binding to cells that express only some or none of the targets. Such a ligand would also be able to select between very similar cell types, indicating new subpopulations of cells. This would have important implications in the fields of research, diagnostics and therapeutics. See references 11, 22-24. Multispecific ligands, then, have great potential. However, the development of such ligands is has been slowed by the difficulty of identifying combinations of targets that, when concurrently expressed, identify a particular cell type. If multispecific ligands are to become a viable treatment option, methods that identify particular cell types using combinations of targets are necessary.

So as to reduce the complexity and length of the Detailed Specification, and to fully establish the state of the art in certain areas of technology, Applicants herein expressly incorporate by reference all of the following materials identified in each numbered paragraph below. The incorporated materials are not necessarily "prior art" and Applicants expressly reserve the right to swear behind any of the incorporated materials.

1. Jemal A et al, Cancer Statistics, *CA Cancer J Clin* 56, 106-130 (March/April, 2006).
2. Hale G, Therapeutic antibodies—Delivering the promise?, *Adv Drug Deliv Rev,* 58 633-639 (May, 2006).
3. Pegram M D et al, Targeted therapy: wave of the future. *J Clin Oncol* 23 1776-1781 (2005).
4. Reichert J M et al, Monoclonal antibody successes in the clinic. *Nat Biotechnol* 23 1073-1078 (2005)
5. Richter M and H Zhang, Receptor-targeted cancer therapy. *DNA Cell Biol* 24 271-282 (2005)
6. Sawyers C, Targeted cancer therapy, *Nature,* 432 294-297 (2004).
7. Vasir J K and Labhasetwar V, Targeted drug delivery in cancer therapy, *Technol Cancer Res Treat,* 4 363-374 (2005)
8. Tang P A, M S Tsao and M J Moore, A review of erlotinib and its clinical use, *Expert Opin Pharmacother* 7 177-193 (February, 2006).
9. Moore M J, Brief communication: a new combination in the treatment of advanced pancreatic cancer, *Semin Oncol* 32 5-6 (2005).
10. Handl H L et al, Hitting multiple targets with multimeric ligands, *Expert Opin Ther Targets,* 8 565-586 (2004).
11. Vagner J et al, Novel targeting strategy based on multimeric ligands for drug delivery and molecular imaging: homooligomers of alpha-MSH, *Bioorg Med Chem Let* 14 211-215 (2004).
12. Son C G et al, Database of mRNA gene expression profiles of multiple human organs, *Genome Res* 15 443-450 (2005).
13. Shyamsundar R et al, A DNA microarray survey of gene expression in normal human tissues, *Genome Biol* 6 R22.1-R22.7 (2005).
14. Kallioniemi O P et al, Tissue microarray technology for high-throughput molecular profiling of cancer, *Hum Mol Genet* 10 657-662 (2001).
15. Nocito A et al, Tissue microarrays (TMAs) for high-throughput molecular pathology research, *Int J Cancer,* 94 1-5 (2001).
16. Torhorst J et al, Tissue microarrays for rapid linking of molecular changes to clinical endpoints, *Am J Pathol* 159 2249-2256 (2001).
17. Kononen J et al, Tissue microarrays for high throughput molecular profiling of tumor specimens, *Nat Med* 4 844-847 (1998).
18. Temming K et al, RGD-based strategies for selective delivery of therapeutics and imaging agents to the tumour vasculature, *Drug Resist Update* 8 381-402 (2005).

19. Haubner R et al, Noninvasive visualization of the activated alphavbeta3 integrin in cancer patients by positron emission tomography and [18F] Galacto-RGD, *PLoS Med,* 2, 0244-0252 (2005).
20. Beer A J et al, PET-based human dosimetry of 18F-galacto-RGD, a new radiotracer for imaging alpha v beta3 expression, *J Nucl Med* 47, 763-769 (May, 2006).
21. Goldenberg D M and Sharkey R M. Novel radiolabeled antibody conjugates, *Oncogene* 26 3734-3744 (May, 2007).
22. Jhanwar Y S and Divgi C, Current status of therapy of solid tumors, *J Nucl Med* 46 141S-150S (2005)
23. Goldenberg D M and Sharkey R M, Advances in cancer therapy with radiolabeled antibodies, *Q J Nucl Med Mol Imaging* 50 248-264 (December, 2006).
24. Boturyn D et al, Template assembled cyclopeptides as multimeric system for integrin targeting and endocytosis, *J Am Chem Soc,* 126 5730-5739 (2004).
25. Handl H L et al, Hitting multiple targets with multimeric ligands, *Expert Opin Ther Targets,* 8 565-586 (2004).
26. Laugel B et al, Design of soluble recombinant T cell receptors for antigen targeting and T cell inhibition, *J Biol Chem* 280 1882-1892 (2005).
27. Garanger E et al, Multivalent RGD synthetic peptides as potent alphaVbeta3 integrin ligands, *Org Biomol Chem,* 4 1958-1965 (April, 2006).
28. Mammen M et al, Polyvalent Interactions in Biological Systems: Implications for Design and Use of Multivalent Ligands and Inhibitors, *Angewandte Chemie* 37 2754-2796 (1998).
29. Boyd R S et al, Proteomic analysis of the cell-surface membrane in chronic lymphocytic leukemia: identification of two novel proteins, BCNP1 and MIG2B, *Leukemia* 17 1605-1612 (2003).
30. Zhao Y et al, Proteomic analysis of integral plasma membrane proteins. Anal Chem, 76 1817-1823 (2004).
31. Loyet K M et al, Proteomic profiling of surface proteins on Th1 and Th2 cells. *J Proteome Res,* 4 400-409 (2005).
32. Tangrea M A et al, Novel proteomic approaches for tissue analysis, *Expert Rev Proteomics* 1 185-92 (2004).
33. Dougherty E R et al, Inference from clustering with application to gene-expression microarrays, *J Comput Biol,* 9 105-126 (2002).
34. Andersen C L et al, Improved procedure for fluorescence in situ hybridization on tissue microarrays, *Cytometry* 45 83-86 (2001).
35. Mousses S et al. Clinical validation of candidate genes associated with prostate cancer progression in the CWR22 model system using tissue microarrays, *Cancer Res* 62 1256-1260 (2002).
36. Watanabe A et al, Tissue microarrays: applications in genomic research, *Expert Rev Mol Diagn,* 5 171-181 (2005).
37. Morse D L et al, Determining suitable internal standards for mRNA quantification of increasing cancer progression in human breast cells by real-time reverse transcriptase polymerase chain reaction, *Anal Biochem* 342 69-77 (2005).
38. Lynch R M et al, Modulation of hexokinase association with mitochondria analyzed with quantitative three-dimensional confocal microscopy, *J Cell Biol* 112 385-395 (1991).
39. Rose A, The sensitivity performance of the human eye on an absolute scale, *J Opt Soc Am* 38 196-208 (1948).
40. Barrett H H and Swindell W, Noise in Images. In: Barrett H H, Swindell W, eds *Radiological Imaging:* Academic Press 494-560 (1981).

Applicants believe that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), applicants will amend the specification to expressly recite the essential material that is incorporated by reference as allowed by the applicable rules.

BRIEF SUMMARY OF THE INVENTION

The present invention provides among other things a method of identifying a cell as a pancreatic cancer cell based on assessing the expression of combinations of targets.

It is an object of the invention to identify a cell as a pancreatic cancer cell by analyzing the expression of a particular combination of at least three targets.

It is an object of the invention to identify a cell as a pancreatic cancer cell by assessing the expression of a particular combination of at least four targets.

It is an object of the invention to identify a cell as a pancreatic cancer cell through microarray analysis of the expression a particular combination of targets.

It is an object of the invention to identify a cell as a pancreatic cancer cell using labeled antibodies to analyze the expression of a particular combination of targets It is an object of the invention to identify a cell as a pancreatic cancer cell through immunohistochemistry analysis of the expression of a particular combination of targets.

It is an object of the invention to identify a cell as a pancreatic cancer cell through immunohistochemistry analysis of the expression of a particular combination of targets expressed on a tissue microarray.

It is an object of the invention to identify a cell as a pancreatic cancer cell using immunocytochemistry analysis of the expression of a particular combination of targets.

It is an object of the invention to identify a cell as a pancreatic cancer cell using a flow cytometer to analyze the expression of a particular combination of targets.

It is an object of the invention to identify a cell as a pancreatic cancer cell by reverse transcriptase polymerase chain reaction (RTPCR).

It is an object of the invention to identify a cell as a pancreatic cancer cell by quantitative real time reverse transcriptase polymerase chain reaction (qRT-RTPCR).

It is an object of the invention to identify a cell as a pancreatic cancer cell using a multispecific targeting agent to analyze the expression of a particular combination of targets.

It is an object of the invention to detect a pancreatic cancer cell using a labeled multispecific targeting agent capable of specifically binding a combination of a set of cell surface proteins that, when expressed in combination, identify a cell as a pancreatic cancer cell.

It is an object of the invention to identify a cell as a pancreatic cancer cell using a multispecific targeting agent that is conjugated with an agent toxic to the cell and is capable of specifically binding a combination of cell surface proteins that identify a cell as a pancreatic cancer cell.

The above and other objects may be achieved using methods involving assessing the expression of PCDHB10, IL1RAP, and SLCO1B3 in combination.

The above and other objects may be achieved using methods involving assessing the expression of PCDHB10, IL1RAP, and PTPRR isoform 1 in combination.

The above and other objects may be achieved using methods involving assessing the expression of PCDHB10, IL1RAP, and PTPRR isoform 2 in combination.

The above and other objects may be achieved using methods involving assessing the expression of PCDHB10, IL1RAP, and SLCA2A13 in combination.

The above and other objects may be achieved using methods involving assessing the expression of PCDHB10, SLC01B3, and FCGR1A in combination.

The above and other objects may be achieved using methods involving assessing the expression of PCDHB10, SLC01B3, and CLEC4A isoform 1 in combination.

The above and other objects may be achieved using methods involving assessing the expression of PCDHB10, SLC01B3, and CLEC4A isoform 2 in combination.

The above and other objects may be achieved using methods involving assessing the expression of PCDHB10, SLC01B3, and CLEC4A isoform 3 in combination.

The above and other objects may be achieved using methods involving assessing the expression of PCDHB10, SLC01B3, and CLEC4A isoform 4 in combination.

The above and other objects may be achieved using methods involving assessing the expression of PCDHB10, TM4SF4, and SLC21A3 in combination.

The above and other objects may be achieved using methods involving assessing the expression of PCDHB10, TM4SF4, and FCGR1A in combination. The above and other objects may be achieved using methods involving assessing the expression of TM4S4, IL1RAP, FCGR1A, and ASGR1 in combination.

The above and other objects may be achieved using methods involving assessing the expression of TM4S4, IL1RAP, PCDHB10, and PCDHB9 in combination.

The above and other objects may be achieved using methods involving assessing the expression of PTPRR isoform 1, SLC01B3, ASGR1, and PTPRC isoform 1 in combination.

The above and other objects may be achieved using methods involving assessing the expression of PTPRR isoform 1, SLC01B3, ASGR1, and PTPRC isoform 2 in combination.

The above and other objects may be achieved using methods involving assessing the expression of PTPRR isoform 1, SLC01B3, ASGR1, and PTPRC isoform 3 in combination.

The above and other objects may be achieved using methods involving assessing the expression of PTPRR isoform 1, SLC01B3, ASGR1, and PTPRC isoform 4 in combination.

The above and other objects may be achieved using methods involving assessing the expression of PTPRR isoform 2, SLC01B3, ASGR1, and PTPRC isoform 1 in combination.

The above and other objects may be achieved using methods involving assessing the expression of PTPRR isoform 2, SLC01B3, ASGR1, and PTPRC isoform 2 in combination.

The above and other objects may be achieved using methods involving assessing the expression of PTPRR isoform 2, SLC01B3, ASGR1, and PTPRC isoform 3 in combination.

The above and other objects may be achieved using methods involving assessing the expression of PTPRR isoform 2, SLC01B3, ASGR1, and PTPRC isoform 4 in combination.

The above and other objects may be achieved using methods involving assessing the expression of PTPRR isoform 1, SLC01B3, ASGR1, and MS4A4A in combination.

The above and other objects may be achieved using methods involving assessing the expression of PTPRR isoform 2, SLC01B3, ASGR1, and MS4A4A in combination.

The above and other objects may be achieved using methods involving assessing the expression of TM4S4, TNFSF4, MGC34293, and TGFBR1 in combination.

The above and other objects may be achieved using methods involving assessing the expression of PCDHB8, HLA-DQA1, PCDHB10, and SLC01B3 in combination.

The above and other objects may be achieved using methods involving assessing the expression of PTPRR isoform 1, CEACAM6, MS4A4A, and SLC01B3 in combination.

The above and other objects may be achieved using methods involving assessing the expression of PTPRR isoform 2, CEACAM6, MS4A4A, and SLC01B3 in combination.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. §112, ¶6. Thus, the use of the words "function," "means" or "step" in the Detailed Description or Description of the Drawings or claims is not intended to somehow indicate a desire to invoke the special provisions of 35 U.S.C. §112, ¶6, to define the invention. To the contrary, if the provisions of 35 U.S.C. §112, ¶6 are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. §112, ¶6. Moreover, even if the provisions of 35 U.S.C. §112, ¶6 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

Figure 1:
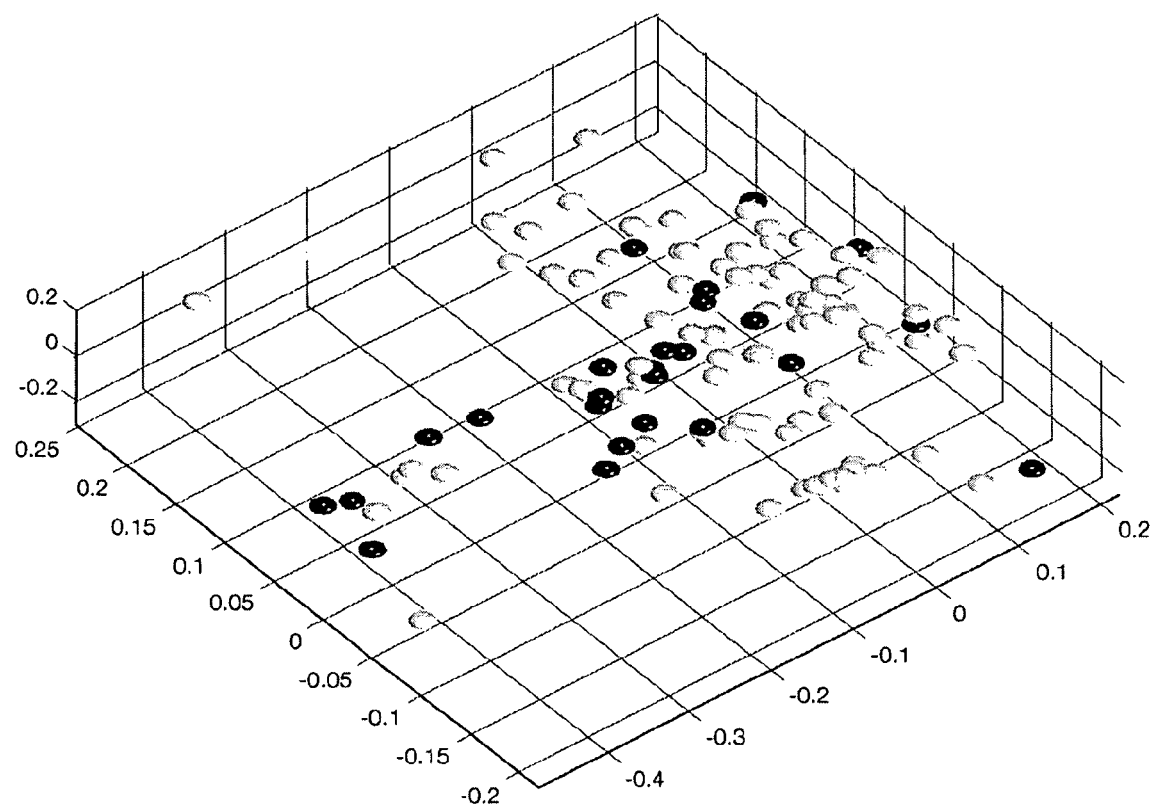
FIG. 1 depicts multidimensional scaling plots of the pancreatic tumor tissues (black dots) and normal tissues (gray dots) based on microarray expression data.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Herein, Applicants describe methods of using combinations of targets expressed by pancreatic cancer cells in order to identify a cell as a pancreatic cancer cell. Targets include any molecular structure produced by a cell and expressed inside the cell, on the cell surface, or secreted by the cell. Targets include proteins, lipids, carbohydrates, nucleic acids, and combinations thereof including subcellular structures, glycoproteins, and viruses. Preferably, the targets include proteins or glycoproteins associated with the cell membrane. A target associated with the cell membrane may achieve said association with the cell membrane by some hydrophobic or other membrane-directing domain such as a membrane-spanning domain. Alternatively, a target may be associated with the cell membrane by as part of a complex of two or more proteins, one of which is directly associated with the cell membrane.

Expression encompasses all processes through which specific molecules may be derived from a nucleic acid template. Expression thus includes RNA transcription, mRNA splicing, protein translation, protein folding, post-translational modification, membrane transport, associations with other molecules, addition of carbohydrate moeties to proteins, phosphorylation, protein complex formation and any other process through which specific biological material may be made from a nucleic acid template. Expression also encompasses all processes through which the production of material derived from a nucleic acid template may be actively or passively suppressed. Such processes include all aspects of transcriptional and translational regulation. Examples include heterochromatic silencing, transcription factor inhibition, any form of RNAi silencing, alternative splicing, protease digestion, post-translational modification, and alternative protein folding. Expression is an integral process of a target in that without expression of the target, there would be no target.

Expression may be assessed by any of a number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, RTPCR, and QRTPCR. Other examples include any process of detecting expression that uses an antibody including the following nonlimiting examples, flow cytometry, immunohistochemistry, ELISA, Western blot, and immunoaffinity chromatograpy. Antibodies may be monoclonal, polyclonal, or any antibody fragment including an Fab, $F(ab)_2$, Fv, scFv, phage display antibody, peptibody, multispecific ligand, or any other reagent with specific binding to a target. Such methods also include direct methods used to assess protein expression including the following nonlimiting examples: HPLC, mass spectrometry, protein microarray analysis, PAGE analysis, isoelectric focusing, 2-D gel electrophoresis, and enzymatic assays. Samples from which expression may be detected include single cells, whole organs or any fraction of a whole organ, whether in vitro, ex vivo, in vivo, or post-mortem. Preferably the sample includes cells derived from human pancreas.

Methods to detect targets may include the use of a ligand with specificity for the target. Ligands may be monospecific (also termed monomeric or monovalent) as well as multispecific (also termed multimeric or multivalent). Monospecific ligands have at least one target binding site, but only one specificity per ligand while multispecific ligands have at least two target binding sites per ligand. While all binding sites on monospecific ligands are equivalent, multispecific ligands include at least two different types of binding site per ligand. Such binding sites on a multispecific ligand may have specificity for different targets or for different epitopes on the same target. Ligands (whether monospecific or multispecific) include antibodies, antibody complexes, conjugates, natural ligands, small molecules, nanoparticles, any combination of molecules that includes one or more of the above, or any other molecular entity capable of specific binding to a target existing now or developed in the future. Monospecific and multispecific ligands may be associated with a label such as a radioactive isotope or chelate thereof, dye (fluorescent or nonfluorescent,) stain, enzyme, nonradioactive metal, or any other substance capable of aiding a machine or a human eye from differentiating a cell expressing a target from a cell not expressing a target whether in existence now or developed in the future. Additionally, expression may be assessed by monospecific or multispecific ligands associated with substances capable of killing the cell. Such substances include protein or small molecule toxins, cytokines, pro-apoptotic substances, pore forming substances, radioactive isotopes, or any other substance toxic to a cell that may be delivered to a cell by a ligand.

Positive expression includes any difference between a cell expressing a specific target and a cell that does not express a specific target. The exact nature of positive expression varies by the method, but is well known to those skilled in the art of practicing a particular method. Positive expression may be assessed by a detector, an instrument containing a detector, or by aided or unaided human eye. Examples include but are not limited to specific staining of cells expressing a target in an IHC slide, binding of RNA from a sample to a microarray and detection by said microarray, a high rate of dye incorporation in real-time RTPCR, detection of fluorescence on a cell expressing a target by a flow cytometer, the presence of radiolabeled bands on film in a Northern blot, detection of labeled blocked RNA by RNAse protection assay, cell death measured by apoptotic markers, cell death measured by shrinkage of a tumor, or any other signal for the expression of a target in existence now or yet to be developed.

A specific target may be identified by the sequence of a nucleic acid from which it can be derived (see Table 8). Examples of such nucleic acids include mRNA, cDNA, or genomic sequences. Alternatively, a specific target may be identified by a protein sequence. However, the specific target is not limited to the products of the exact nucleic acid sequence or protein sequence by which it may be identified. Rather, a specific target encompasses all sequences that yield positive expression when the expression of the specific target is assessed. Examples of sequences encompassed by a specific target identified by a nucleic acid molecule include point mutations, silent mutations, deletions, frameshift mutations, translocations, alternative splicing derivatives, differentially methylated sequences, differentially modified protein sequences, and any other variation that results in a product that may be identified as the specific target. The following nonlimiting example is included for the purposes of illustrating the concept of what is encompassed by a target: if expression of a specific target in a sample is assessed by immunohistochemistry, and if the sample expresses a sequence different from the sequence used to identify the specific target (e.g. a variation of one or more nucleic acid molecules,) but positive expression is still determined, then the target encompasses the sequence expressed by the sample.

In one aspect of the invention, target expression may be assessed by microarray. The following protocol is included solely to illustrate one example of this aspect of the invention. This aspect also encompasses any variation the following protocol including any method that assesses the expression of a target through the binding of a complimentary nucleic acid probe. In addition, the following protocol describes the methodology used in identifying combinations of targets that identify cells as prostate cancer cells. Total RNA is isolated from tissues using the NucleoSpin RNA II isolation kit (BD Biosciences, Palo Alto, Calif.) following manufacturer's instructions hereby incorporated by reference. The microarray analysis including target labeling and chip hybridization and processing are carried out by following the protocols recommended by the manufacturer, (Agilent Technologies, Palo Alto, Calif.), hereby incorporated by reference. Briefly, 1 µg of total RNA is used to generate CY5 cRNA targets using the Agilent low input RNA fluorescent linear amplification kit, using manufacturer's protocol, hereby incorporated by reference. A total RNA sample isolated from normal pancreas is labeled with CY3 to serve as a reference. The concentration and integrity of fluorescent cRNA as well as the incorporation efficiency of cyanine dyes are analyzed using the Agilent 2100 Bioanalyzer RNA microfluidics chip following manufacturer's protocols, hereby incorporated by reference. Equal amounts of labeled cRNA targets from the tissue sample and the universal reference are hybridized onto Agilent Human 1A and Agilent Human 1A (V2) oligonucleotide arrays. The hybridization signals are acquired and normalized using Agilent's Feature Extraction Image Analysis software (v.7.1).

To obtain targets useful in detecting cells as pancreatic cancer cells, DNA microarray expression data was assessed in three pancreatic cell lines, all of which were obtained from the American Type Tissue Collection (ATCC), were generated using the same procedure using total RNA isolated from cells grown to ~80% confluent. The arrays include 18,778 and 22,073 individual 160-mer probes, respectively. Microarray data was obtained from the 105 normal tissue/cell samples representing 28 different organ sites/cell types. In addition, microarray data was obtained from 28 pancreatic adenocarcinoma tissue samples. The feature intensities derived from each sample were first normalized by the median intensity value of the array in order to cross compare different samples run on different chips. Multidimensional scaling (MDS) analysis was used to test the internal consistency of the data set by checking the clustering of the individual samples. As shown in FIG. 1, despite the fact that the tissues were obtained from different sources and represent diverse ethnic, age and sex groups, normal tissue samples belonging to the same organ type tend to cluster together. In contrast to this observation, the pancreatic tumor samples were not always clustered, indicating more heterogeneous expression patterns in the pancreatic tumors.

Applicants focused upon targets expressing putative cell surface molecules included in the Agilent Human 1A and 1A V2 oligonucleotide array, with cell surface or transmembrane regions. A total of 2133 targets met their criteria. Applicants then manually examined the cellular localization of each target by browsing through information in databases (Genecard, Harvester, Entrez, Protein Database, UniProt and PubMed) and literature (PubMed). Targets encoding proteins with putative cell-surface or transmembrane regions were also included. The final list consists of 2,133 targets, including GPCRs, integral membrane proteins and other cell surface proteins. Each category was followed through the hierarchy to the lowest possible level in order to select lists containing targets with cell-surface epitopes, while excluding lists that were sure to not include cell-surface proteins. A list was compiled from all of the selected lists containing 6,389 targets. Since Applicants intended to use this list to assess expression using the Agilent Human 1A (V2) oligonucleotide array chips, Applicants removed targets from our cell-surface list that were not represented on the Agilent array. The resulting new list contained 4,407 targets. Each target on the master list was then checked using information from existing databases (Genecard, Harvester, Entrez, Protein Database, UniProt and PubMed) to determine if it encodes a cell surface protein, if it is predicted to encode one by similarity or homology, if it is a non cell-surface target, or if the sub-cellular localization is not determinable. Non cell-surface targets were removed from the list. The resulting list was thus enriched with targets expected to encode proteins that have epitopes exposed on the cell surface. Our final list contains a total of 2177 targets covered by the Agilent Human 1A V2 and 1928 targets covered by the 1A (V1).

Hierarchical clustering (agglomerative procedure) was used to form clusters using the median normalized microarray expression data of the cell surface targets of the tissue samples. The object of this clustering analysis is to compute a dendrogram that assembles all tissue samples into a single tree based on their similarities in cell surface target expression (see FIG. 3). The clustering algorithm used is based on the average-linkage method as described in reference 17. Since our tissue samples had 29 distinct types (28 different normal tissue/cell types plus the pancreatic tumor tissue group), the repetitive clustering process was stopped when it formed 29 groups.

Figure 2:
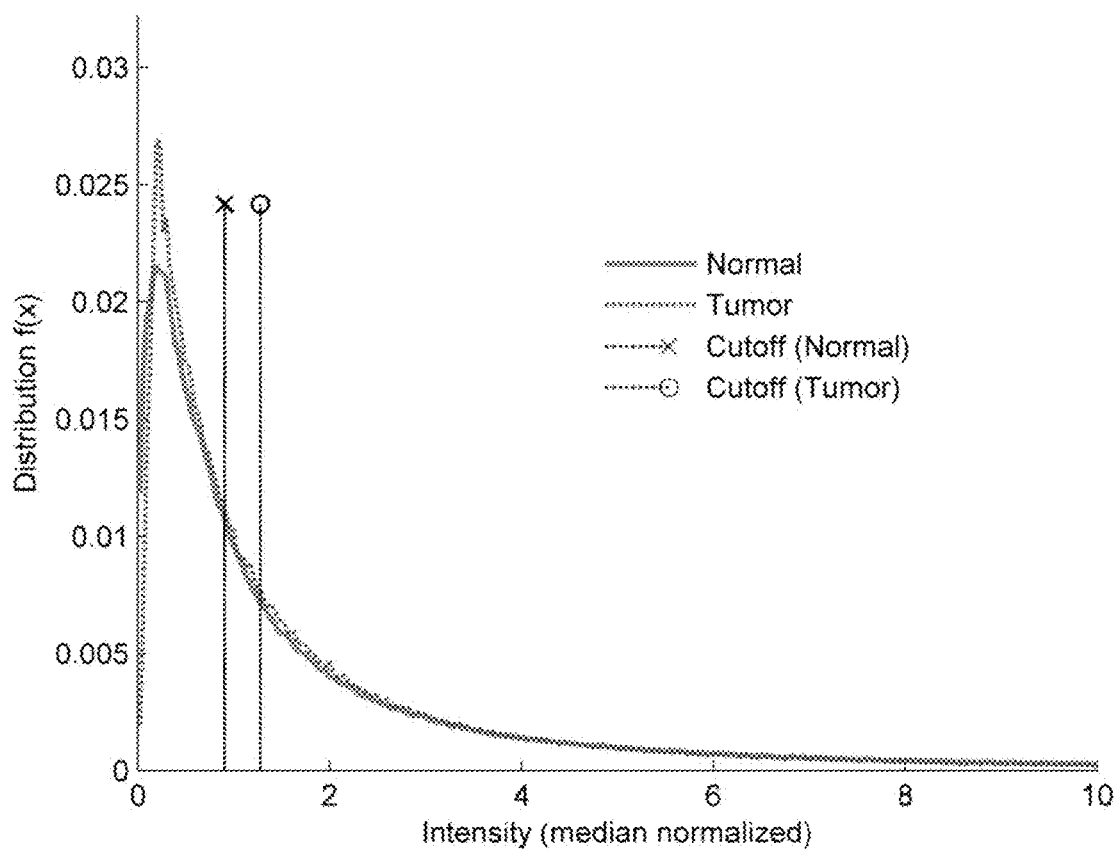
FIG. 2 depicts microarray intensity distribution plots of pancreatic tumor samples (dashed line) and normal tissue samples (solid line). Vertical lines show cutoff values demarcate a target as either "positively expressed" in a given tumor sample (dashed line with a circle) or "not expressed" in a given normal sample (dashed line with a cross).

Referring now to FIG. 2, the frequency histogram of mRNA abundance follows a pseudo-power law. Thus, an important component of the effort includes assessing RNA expression from non-expression when using microarray analysis. Because the level of mRNA expression is not always linearly related to the level of protein translation and subsequent localization to the cell surface, Applicants determined the relationship between assessing the expression of targets through microarray and assessing the expression of targets through methods that measure protein at the cell surface. The normal and tumor threshold values (indicated in the vertical lines in FIG. 2) were adjusted in order to provide the target combinations with the maximum stringency of the coverage analyses. DNA array intensities below the value of normalized normal tissue threshold values are considered not to have positive expression. Intensities above tumor tissue threshold values displayed positive expression. Setting a normal tissue based threshold value of 0.35, provided no combinations while using any higher tumor cutoff setting. Setting a tumor area based threshold value of 0.75, provided no combinations while using any lower normal cutoff setting. Area based cutoffs that provided target combinations ranged from 0.35 to 0.55 in normal tissues, and 0.55 to 0.75 in tumor tissues. Combinations that provided the highest coverage amongst tumor tissues with the most stringent cutoff values were selected.

To further demarcate positive expression from non-expression, Applicants quantified the expression of common CD (Cluster of Differentiation) targets using Europium-labeled antibodies binding to three different cell lines (Mia PaCa-2, BxPC-3 and Capan-2) with varying RNA expression as determined by microarray of the CD targets. Results are summarized in Table 7. Binding was quantified on whole cells using time resolved fluorescence and indicated that median normalized intensities of 0.55 as measured in microarray analysis corresponded to the minimum detectable protein level above the background signal. However, CD antibody binding data also showed that higher microarray intensity does not necessarily indicate a high binding signal. Applicants used a median microarray intensity ratio of 0.45 non-expression cutoff in normal tissue samples. Applicants used microarray intensity levels from 0.55 to 0.85 as a positive expression cutoff in pancreatic tumor tissue samples. Microarray data were parsed with these varying levels of upper cutoff to generate binarized data with a value of 1 to signify positive expression and 0 to signify non-expression.

Microarray data were generated using eleven pancreatic adenocarcinoma cell lines. From these data, five lines (AsPC-1, Capan-1, HPAFII, PSN-1 and SU86.86) were selected that may express all three targets in at least one of the validated three-target combinations. Expression of the four validated targets (IL1RAP, PCDHB10, PTPRR and SLC1A13) was determined quantitatively at the level of mRNA by qRT-PCR, and qualitatively at the level of protein by immunocytochemistry (ICC) (results summarized in Table 7). Cell lines were identified that express all three targets in both validated combinations, e.g. AsPC-1 and Capan-1 cells express targets in both combinations at relatively high levels. When expression of the IL1RAP-PCDHB10-PTPRR combination was assessed, Capan-1 cells expressed mRNA ranging from 0.006-0.05 the level of β-actin (ACTB) mRNA and demonstrated relatively high staining of all three targets by ICC.

When assessing the expression of cells with a multispecific targeting agent, the binding avidity to a cell is determined by the binding affinities of the individual ligands that make up the agent to the respective target receptors as well as by the presence and concentration of each target receptor on the cell surface. The cellular specificity of a multispecific targeting agent is largely determined by differences in the expression of each target protein between normal and tumor tissues. In the following nonlimiting example: a multispecific ligand that binds to 3 different target proteins in a tumor and only 1 protein in a normal tissue (difference of 2 in the number of proteins it binds) will have a higher specificity than a ligand that binds to 3 proteins in a tumor and 2 proteins in a normal tissue (difference of 1 in the number of proteins).

Based on the results of empirical studies, Rose and others have determined that detection of an image detail by the human eye requires a signal intensity to background noise ratio (SNR) of at least 2 to 3 (see references 39 and 40). Thus, in the case of imaging, a 3-fold signal enhancement in a target tissue relative to background enhancement is generally required. Further, it is estimated that in the case of targeted therapies, a 100-fold increase in binding to target tissue relative to normal tissues is required (see reference 25). Vagner and others have reported that ligands exhibiting heterobivalent binding interactions demonstrate an ~50-fold increase in binding relative to monovalent interactions (see reference 11). An ~100-fold increase in homotrivalent binding interactions relative to monovalent interactions was also demonstrated (see references 11 and 28).

From these observations of cooperative affinity, Applicants selected combinations of targets with a difference of 2 in the number of targets in tumor tissue relative to normal tissue. That is, if a combination contains N targets and the tumor expresses all N targets, no more than N-2 targets may be expressed in any given normal tissue by microarray. In the case of two-target combinations, neither target may be expressed in normal tissue. To identify target combinations that meet this rule, the expression of the cell surface targets was binarized to non-expression or positive expression in each tissue sample using area-based cutoff values with the highest possible stringency To rank the target combinations by their coverage of tumor samples, a coverage flag '1' was assigned to a tumor sample if positive expression of a given target combination was at least N-2 greater than in all normal samples. Otherwise, the tumor sample was assigned '0'. This process is repeated with each individual tumor sample and the combination was ordered based on the coverage ('average coverage flag') obtained from all the tumor samples. Thus, the highest ranked combinations covered the most tumors with low to no avidity to most, if not all, normal tissues. Because higher dimensional combinations might be computed, it is possible that the same tumor samples could be covered by lower dimensional combinations. In order to only select combinations that cover more tumor samples than any lower dimension combinations Applicants introduced the Coverage Measurement ($\Psi$) to quantify each combination. If $\Psi_q$ is the Coverage Measurement of the qth dimension, then a combination with q+1 dimensions is said to have an improvement in coverage over a combination with q dimensions only if: $\Psi_{q+1} > \Psi_q$. Only combinations with a higher Coverage Measurement than all combinations with lower dimensions ($\Psi_{q+1} > v\{\Psi_1, \Psi_2, \ldots, \Psi_q\}$) were selected as valid target combinations.

To identify single targets, Applicants assessed the expression of each of the targets in the final list (above) in both pancreatic tumors and normal pancreas. Using a median normalized ratio of 0.45 as the non-expression cutoff in normal pancreas and 0.85 as the positive expression cutoff in pancreatic tumor tissues, Applicants produced a list of targets non-expressed in normal pancreas but expressed in at least 20% of the pancreatic cancer patient samples. Targets with positive expression in normal liver, heart, kidney, lung and pancreas, or in two or more other normal tissue types were eliminated from further consideration.

Figure 3:
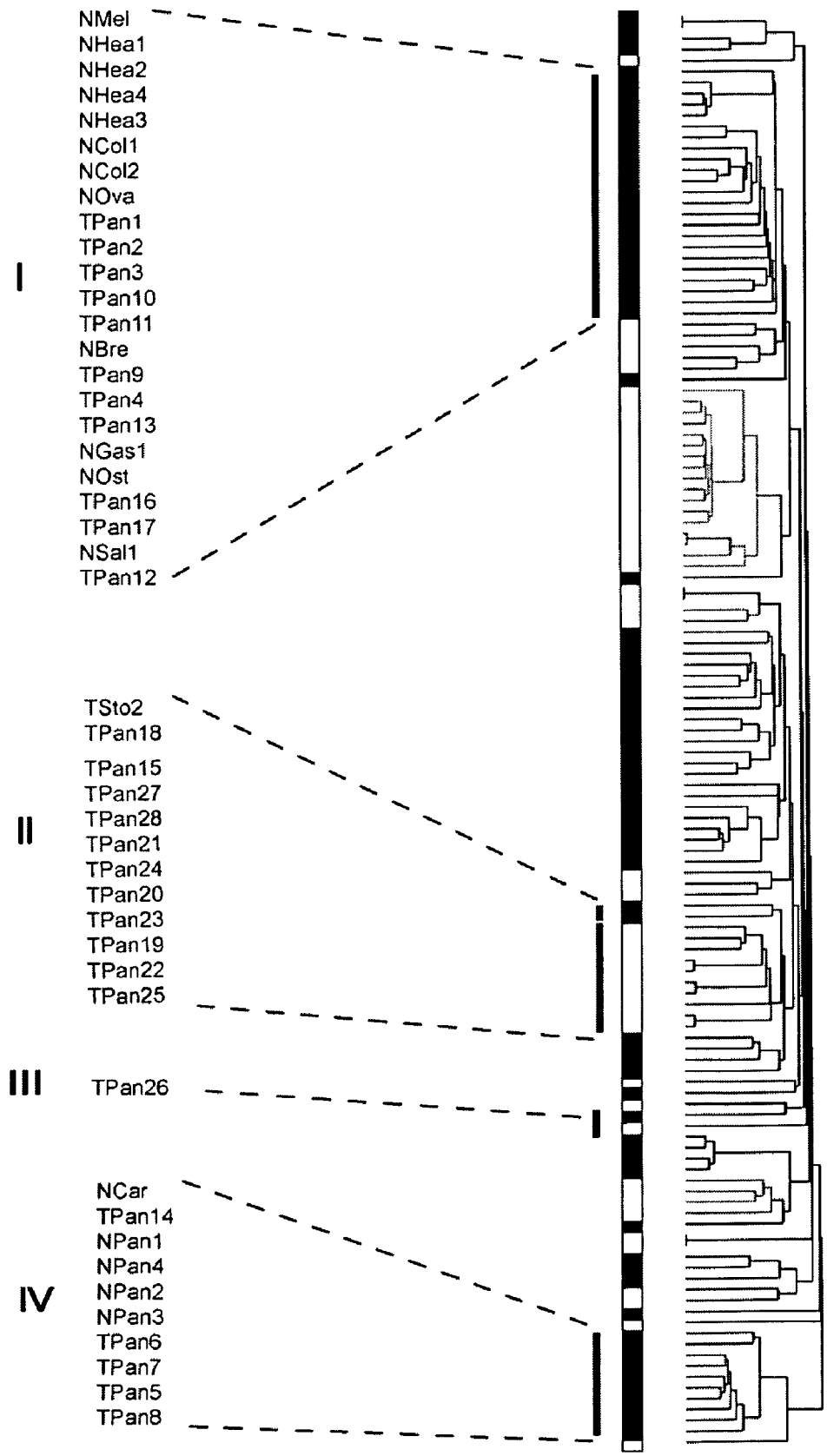
FIG. 3 depicts a dendrogram of pancreatic tumor tissue groupings with normal tissues based on expression of cell-surface targets. NMel: normal melanocytes; Nhea: Normal heart; NCol: Normal colon; NBre: Normal breast; NOva: Normal ovary; NOst: Normal osteoblasts; NSal: Normal salivary gland; NSke: Normal skeletal muscle; NAdi: Normal adipose tissue; NAdr: Normal Adrenal gland; NSto: Normal stomach; NCar: Normal cartilage tissue; NPan: Normal pancreas; TPan: Pancreatic tumor samples.

The analysis resulted in a set of three-target and four-target combinations that each cover at least 3 out of 28 (11%) of pancreatic tumor samples assessed. The three-target combinations are listed in Table 2 and the four-target combinations are listed in Table 3. Combinations containing more than four targets may be assembled using the three- and four-target combinations, and other aspects of the invention encompass these combinations as well. FIG. 3 is a dendrogram that reveals a clustering of pancreatic tumor tissues into four groupings by expression of cell-surface targets, with 96% of the tumor tissues being divided between three major groupings (I, II and IV). Group II contains two very close clusters (the Nsto2/TPan18 cluster and the TPan16/TPan19-TPan25/TPan27-TPan28 cluster). Group IV tumors clustered with the normal pancreas tissue, indicating that these tumors may be difficult to distinguish from normal pancreatic tissue by cell-surface expression, or that the tumor biopsy samples in group IV contain a high percentage of normal tissue. Groups I and II each contain 39% of the tumor samples. The three- and four-target combinations that were identified as having the broadest tumor coverage, predominantly covers tumors in group II, with three of the seven 3-target combinations also covering the single tumor in group III, one of the seven 4-target combinations covered the single tumor in group III and three of the seven covered one tumor in group I. Together, the combinations identified cover 100% of the group II tumors.

Figure 4:
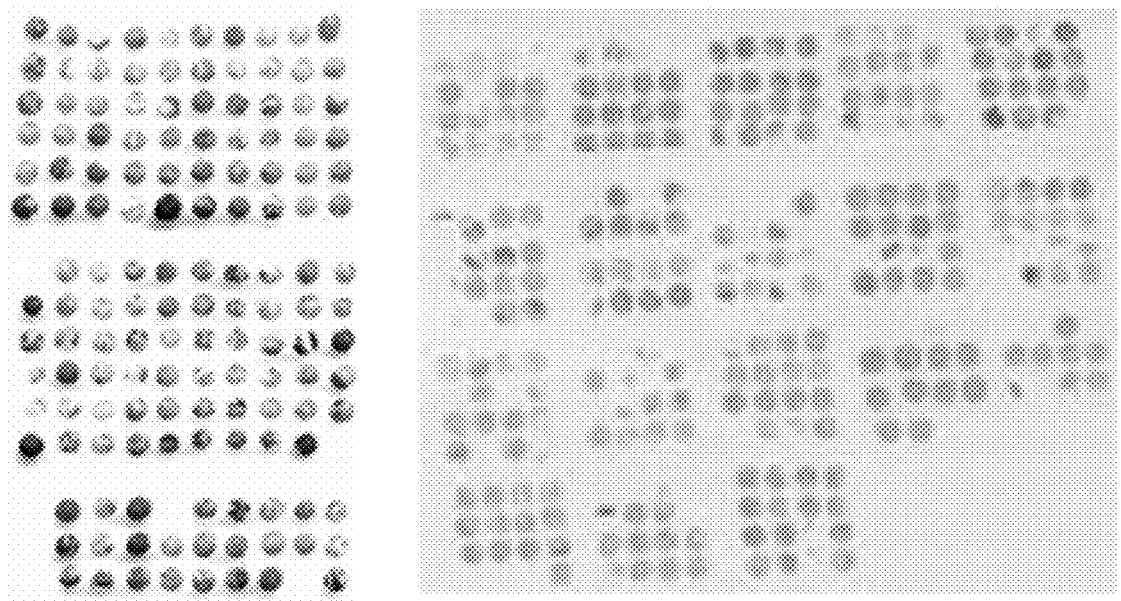
FIG. 4 depicts validation of target combinations by tissue microarray (TMA) based immunohistochemistry. The pancreatic tumor TMA (left) was constructed by Applicants and the normal tissue microarray (right) was obtained from NCI's cooperative tissue network.

In one aspect of the invention, expression of a target may be assessed within the context of a tissue. The following protocol is included solely to illustrate one example of this aspect of the invention. This aspect of the invention encompasses all variations on the protocol and any other protocol that results in a set of one or more tissues that facilitates assessing the expression of a target. Such tissues include whole, excised, post mortem, frozen or paraffin embedded sections, or tissues presented in the context of a tissue microarray (TMA.) To construct a tissue microarray, morphologically representative areas of tumors were selected from formalin fixed tissue samples embedded in paraffin blocks. Two 1.5 mm diameter cores per case were re-embedded in a tissue microarray using a tissue arrayer according to Kononen's method (see reference Number 17). An average of 200 sections can be cut from one tissue microarray block. Using this procedure, Applicants examined two pancreatic tissue microarrays (shown in FIG. 4). To construct a TMA, formalin-fixed paraffin embedded tissues were examined with H&E staining of whole sections to identify pathological distinct areas of interest. With each tissue block, areas representative of tumor, borderline and normal were selected to punch 1.0 mm-diameter discs (two discs per tumor, one disc per border line normal and one disc per normal) used in TMA construction. The discs were re-embedded into a new paraffin block using a tissue arrayer (See references 17 and 34-36). A total of 52 pancreatic ductal adenocarcinoma cases, 38 of which also included a disc from adjacent normal region, 2 cases of pancreatitis and 2 cases of normal pancreas samples were included in the array. After the completion of the block, 5-µm sections were cut with a microtome. The TMA slides were dipped in paraffin in order to achieve uniform epitope preservation. The entire TMA block was sectioned with H & E staining every 50 sections to assess retention of desired tissue targets. TMA slides containing normal tissues were obtained from the Corporative Human Tissue Network of the National Cancer Institute, National Institutes of Health, Bethesda Md. (Version CHTN2002N1). This normal tissue TMA series contains 66 human tissue types in 0.6 mm spot sizes (chtn.nci.nih.gov).

In one aspect of the invention, target expression may be assessed by immunohistochemistry. The following protocol is included solely to illustrate one example of this aspect of the invention. This aspect of the invention encompasses all variations on the protocol and any other protocols that may assess the expression of a target using an agent capable of specifically binding the target in the context of a section of tissue. Antibodies capable of specifically binding to one of the targets are titrated against regular tissue sections and 'tester' TMA slides that contain a variety of tumor and normal counterpart tissues in order to optimize the binding conditions. TMA slides are subjected to antigen retrieval by heating at 100° C. in citrate buffer (0.1 M, pH 6.0) for 5-30 min, depending on the antibody used. The slides are incubated with the primary antibodies at the optimized dilutions for 30 minutes at room temperature. Biotinylated secondary antibodies are applied to the tissues, as is streptavidin-peroxidase complex. Binding is resolved with diaminobenzidine (DAB). Slides are evaluated using light microscopy and scored (0=negative, to 3+=intensely positive). Examples of primary antibodies, their sources, and the dilutions used in TMA staining include: rabbit anti-PTPRR (Orbigen Inc, San Diego, Calif.), 1:100; rabbit anti-SLC2A13 (Unites States Biological, Swampscott, Mass.), 1:300; mouse anti-PCDHB10 (Abnova corporation, Teipei, ROC), 1:75; and rabbit anti-IL1RAP (Abcam Inc., Cambridge, Mass.), 1:150. These antibodies cover of two of the three-target combinations listed in Table 2 in their entirety and contain at least one target in the remaining three target combinations listed in Table 2. In addition, these antibodies cover two targets in one of the four-target combinations listed in Table 3 and at least one target in five of the four-target combinations listed in Table 3.

Scoring results are summarized in Table 4. In brief, defining positive expression as a score of 2+ or above, all four targets displayed positive expression in most tumor tissues and non-expression in the normal, non-diseased tissues. The target PTPRR was positively expressed in 75% of the tumor cases assessed, the target PCDHB 10 was positively expressed in 37% of the tumor cases assessed, the target IL1RAP was positively expressed in 48% of the tumor cases assessed, and the target SLC2A13 was positively expressed in 47% of the tumor cases assessed. Non-expression was seen in all normal pancreas assessed.

In addition, expression of two target combinations on normal non-pancreatic tissue was assessed. The results obtained from the combination of PTPRR, IL1RAP and PCDHB10 are summarized in Table 5, while the results obtained from the combination of IL1RAP, PCDHB10, and SLC2A13 are summarized in Table 6. Positive expression (score of greater than 2+) of PTPRR was seen in the gastric mucosa, fallopian tube, adrenal gland and kidney. Positive expression of IL1RAP was seen in small intestine, fallopian tube, and bladder epithelium, positive expression of PCDHB10 was seen in the adrenal gland and kidney, and positive expression of ELC2A13 was not seen in any of the tissues assessed in Table 6. So the PTPRR, IL1RAP, and PCDHB10 combination displays positive expression of two of the targets in fallopian tube, adrenal gland, and kidney. The IL1RAP, PCDHB10, and SLC2A13 combination displays positive expression in fallopian tube only.

In another aspect of the invention, expression may be assessed by quantitative real-time reverse-transcriptase PCR (qRT-RTPCR.) The following protocol is included solely to illustrate one example of this aspect of the invention. This aspect of the invention encompasses all variations of the following protocol including any protocol through which target RNA expression may be assessed through a PCR or other nucleic acid amplification. Additionally, this aspect of the invention encompasses assessing target RNA in any sample including whole tissue, biopsy samples, necropsy samples, punches, cells removed by laser-capture microdissection, or any other samples that may contain one or more mRNA molecule in a condition that allows amplification by any method. The protocol is based upon the qRT-RTPCR protocol in reference 22, but with the following alterations. Primer sets are designed to amplify fragments derived from ACTB (β-actin), IL1RAP, PCDHB10, PTPRR, and SLC2A13 mRNA, and PCR conditions are determined (summarized in Table 1). Real-time RT-PCR is conducted using a Smart Cycler® (Cephid, Sunnyvale, Calif.)—the operations manual of which is herein incorporated by reference—and the QuantiTect SYBR Green RT-PCR Kit (Qiagen, Valencia, Calif.)—manufacturers protocol hereby incorporated by reference. Reverse transcriptase (RT) conversion of RNA into cDNA may be performed during a 20 min (HotStarTaq) incubation at 50° C., followed by a 15 min incubation at 95° C. followed by 35 of the following cycles (15 seconds at 94° C., 30 seconds at a primer-set specific annealing temperature, and 20 seconds at 72° C.).

Melt curves ranging from 60 to 90° C. yielded a single melt-peak in all template reactions and a minimal melt peaks in the no-template control reaction. Raw mRNA expression values were determined as being $2^{-C_T}$, where $C_T$ is the second derivative of the fluorescence curve. Target expression was normalized to ACTB expression. Target expression was assessed in the AsPC-1, Capan-1, HPAFII, PSN-1 and SU86.86 cell lines, summarized in Table 7 using three extracts per cell line (to determine mean and standard error.) Reproducibility of measurements by this method is high (Cronbach's alpha of 0.93 (see reference 37)) so only one run per primer set per extract was performed. Results are reported in Table 7 as the mean and error is reported as standard error of the mean (sem).

In another aspect of the invention, expression may be assessed by immunocytochemistry (ICC.) The following protocol is included solely to illustrate one example of this aspect of the invention. This aspect includes all variations on the protocol as well as any protocol that may be used to assess expression of a target using fluorescently labeled ligands capable of specifically binding to one or more targets, including assessment of expression in a flow cytometer. The protocol is based upon that reported by Lynch, et al (see reference 38) and uses the same primary antibodies capable of specifically binding IL1RAP, PTPRR, and SLC2A13 used in the immunohistochemistry example above. The secondary antibody used to stain IL1RAP, PTPRR and SLC2A13 antibodies in this example is Molecular Probes® AlexaFluor488 Goat Anti Rabbit (Invitrogen, San Diego, Calif.), and the secondary antibody used to stain PCDHB10 antibody is Molecular Probes® AlexaFluor488 Goat Anti-mouse (Invitrogen, San Diego, Calif.). Primary antibodies are diluted 1:50 and secondary antibodies are diluted 1:200. Cells are grown to 80% confluence on glass coverslips in 6-well plates. ICC was performed in duplicate on each cell-line and primary antibody combination. Control experiments are performed on each cell line by not including eliminating the primary antibody incubation. Following incubation, coverslips are mounted on slides using Vectashield fluorescence mounting medium (Vector Laboratories, Burlingame, Calif.) and slides stored in the dark at −20° C. until scoring. Scoring is performed using an A.G. Heinze™ Precision MicroOptics TS100 inverted microscope with fluorescence and mounted digital camera (A.G. Heinze, Inc., Lake Forest, Calif.). Positive expression was assessed as ++ or above and non-expression as + or below. Results are summarized in Table 7.

In one aspect of the invention, expression is assessed using a multispecific (also known in the art as multimeric) targeting agent. Multispecific targeting agents may be comprised of more than one binding domain tethered together via a linker or scaffold. Other examples of multispecific targeting agents include bispecific antibodies, complexes that include binding sites capable of binding to multiple targets or multiple epitopes on the same target or any other agent capable of more than one binding specificity whether in existence now or yet to be developed. The specificity of a multispecific targeting agent with regard to a cell may be determined by the difference in the number of targets expressed by the cell the multispecific targeting agent is designed to identify and the number of targets expressed by other cells. In the following nonlimiting example: one multispecific targeting agent capable of binding with three or more different targets in a tumor cell, but only a single target in a normal cell in the same tissue will have a higher specificity than a multispecific targeting agent that is capable of binding with three or more targets in a tumor cell and two or more different targets in a normal cell in the same tissue. A multispecific targeting agent should be capable of specifically binding at least two more targets expressed on the cell type it is designed to target than the number expressed on other similar tissue. While this two-or-more target excess is optimal, this aspect of the invention also encompasses an excess of one target.

TABLE 1

| Target Sequence | Accession No. | Primer | Sequence (5'-3') | Product Length (bp) | Annealing T (° C.) |
| --- | --- | --- | --- | --- | --- |
| IL1RAP mRNA/cDNA | NM_002182 | forward | gct gtg cat ctt tga ccg a (SEQ ID NO: 51) | 86 | 53 |
| | | reverse | gag gcg tct gct ttt ctg aa (SEQ ID NO: 52) | | |
| PCDHB10 mRNA/cDNA | NM_018930 | forward | cag ggt ttc cta ctg ctg ttc (SEQ ID NO: 53) | 121 | 53 |
| | | reverse | aca gga ctt gcc ttt gtc ttg (SEQ ID NO: 54) | | |

TABLE 1-continued

| Target Sequence | Accession No. | Primer | Sequence (5'-3') | Product Length (bp) | Annealing T (° C.) |
|---|---|---|---|---|---|
| PTPRR mRNA/cDNA | NM_002849 | forward | agg agt tgt gga tgc act aag (SEQ ID NO: 55) | 127 | 53 |
| | | reverse | ctg ctg aaa gtc tgc tct cat a (SEQ ID NO: 57) | | |
| SLC2A13 mRNA/cDNA | NM_052885 | forward | tgg gag tct ggc ttg ttg ag (SEQ ID NO: 56) | 82 | 53 |
| | | reverse | ata atg agt gct acg gtg gta cc (SEQ ID NO: 58) | | |

TABLE 2

| Combination | Target Symbols | | | Tumor Coverage by Cluster Analysis Grouping (See FIG. 3) |
|---|---|---|---|---|
| 1 | TM4SF4 | PCDHB10 | FCGR1A | Group II: TPan21, TPan22, TPan24, and TPan 25 |
| 2 | IL1RAP | PCDHB10 | SLCO1B3 | Group II: TPan21, TPan22, TPan24, and TPan25 |
| 3 | PTPRR | IL1RAP | PCDHB10 | Group II: TPan22 and TPan25. Group III: TPan26. |
| 4 | IL1RAP | PCDHB10 | SLC2A13 | Group II: TPan22 and TPan25. Group III: TPan26 |
| 5 | TM4SF4 | PCDHB10 | SLC2A13 | Group II: TPan22 and TPan25. Group III: TPan26 |
| 6 | PCDHB10 | FCGR1A | SLCO1B3 | Group II: TPan21, TPan22, TPan24 and TPan25 |
| 7 | CLEC4A | PCDHB10 | SLCO1B3 | Group II: TPan21, TPan22, TPan24 and TPan25 |

TABLE 3

| Combination | Target Symbols | | | | Tumor Coverage by Cluster Analysis Group See FIG. 3 |
|---|---|---|---|---|---|
| 1 | TM4SF4 | FCGR1A | ASGR1 | IL1RAP | Group II: TPan19, TPan21, TPan22, TPan24, TPan25 and TPan27. |
| 2 | TM4SF4 | PCDHB10 | PCDHB9 | IL1RAP | Group II: TPan21, TPan22, TPan24 and TPan25 Group III: TPan26. |
| 3 | TNFSF4 | TM4SF4 | MGC34923 | TGFBR1 | Group II: TPan15, TPan19, TPan22, TPan25 and TPan27 |
| 4 | PCDHB8 | HLA-DQA1 | PCDHB10 | SLCO1B3 | Group II: TPan18, TPan21, TPan22, TPan24 and TPan25 |
| 5 | PTPRR | PTPRC | SLCO1B3 | ASGR1 | Group I: TPan10. Group II: TPan20, TPan22, TPan23, TPan25 and TPan28 |
| 6 | PTPRR | MS4A4A | SLCO1B3 | ASGR1 | Group I: TPan10. Group II: TPan20, TPan22, TPan23, TPan25 and TPan28 |
| 7 | PTPRR | CEACAM6 | MS4A4A | SLCO1B3 | Group I: TPan10. Group II: TPan20, TPan22, TPan23, TPan25 and TPan28 |

TABLE 4

| Target | Sample classification | Score | | | | | % of cases with ≧2+ |
|---|---|---|---|---|---|---|---|
| | | 0 | 1+ | 2+ | 3+ | N/E | |
| PTPRR | Normal | 2 | 2 | 0 | 0 | 0 | 0 |
| | Tumor | 0 | 12 | 28 | 8 | 4 | 75 |
| PCDHB10 | Normal | 3 | 1 | 0 | 0 | 0 | 0 |
| | Tumor | 1 | 21 | 22 | 4 | 4 | 37 |
| IL1RAP | Normal | 4 | 0 | 0 | 0 | 0 | 0 |
| | Tumor | 6 | 19 | 18 | 5 | 4 | 48 |
| SLC2A13 | Normal | 2 | 0 | 0 | 0 | 2 | 0 |
| | Tumor | 7 | 18 | 18 | 4 | 5 | 47 |

TABLE 5

| Target | Tissue | | |
|---|---|---|---|
| | PTPRR | IL1RAP | PCDHB10 |
| Gastric Mucosa | 3+ | 1+ | 1+ |
| Small Intestine | 0 | 2+ | 1+ |
| Epididymis | 1+ | 1+ | 1+ |
| Seminiferous tubules | 1+ | 0 | 2+ |
| Gallbladder | 1+ | 1+ | 0 |
| Salivary gland | 1+ | 0 | 1+ |
| Hair follicle | 0 | 1+ | 1+ |
| Fallopian tube | 2+ | 2+ | 1+ |
| Adrenal gland | 2+ | 0 | 3+ |

TABLE 5-continued

|  | Tissue | | |
|---|---|---|---|
| Target | PTPRR | IL1RAP | PCDHB10 |
| Bronchial cartilage | 1+ | 0 | 1+ |
| Uterus, smooth muscle | 1+ | 0 | 1+ |
| Ovary, corpus luteum | 1+ | 1+ | 1+ |
| Placenta | 1+ | 1+ | 1+ |
| Appendix | 0 | 1+ | 1+ |
| Bronchial epithelium | 1+ | 0 | 1+ |
| Kidney | 2+ | 0 | 2+ |
| Bladder epithelium | 1+ | 2+ | 1+ |

TABLE 6

|  | Target | | |
|---|---|---|---|
| Tissue | IL1RAP | PCDHB10 | SLC2A13 |
| Gastric mucosa | 1+ | 1+ | 1+ |
| Epididymis | 1+ | 1+ | 0 |
| Small Intestine | 2+ | 1+ | 0 |
| Hair follicles | 1+ | 1+ | 0 |
| Fallopian Tube | 2+ | 1+ | 0 |
| Adrenal gland | 0 | 3+ | 1+ |
| Ovary, corpus luteum | 1+ | 1+ | 0 |
| Placenta | 1+ | 1+ | 0 |
| Appendix | 1+ | 1+ | 1+ |
| Kidney | 0 | 2+ | 1+ |
| Bladder epithelium | 2+ | 1+ | 1+ |

TABLE 7

| | Target | | | | | | | |
|---|---|---|---|---|---|---|---|---|
| Cell Line | IL1RAP mRNA (sem)# | IL1RAP Protein† | PCDHB10 mRNA (sem)# | PCDHB10 Protein† | PTPRR mRNA (sem)# | PTPRR Protein† | SLC2A13 mRNA (sem)# | SLC2A13 Protein† |
| AsPC-1 | 1.9 (0.1) | +++ | 13 (3) | +++ | 57 (10) | +++ | 90 (10) | +++ |
| Capan-1 | 12 (2) | +++ | 5.5 (0.8) | +++ | 46 (8) | +++ | 1.5 (0.8) | +++ |
| HPAFII | 0.63 (0.1) | +++ | 2.0 (0.3) | ++ | 26 (5) | +++ | 5.9 (4) | +++ |
| PSN-1 | 0.70 (0.1) | +++ | 0.044 (0.004) | ++ | 0.1 (0.09) | ++ | 11 (0.6) | ++ |
| SU86.86 | 0.62 (0.1) | + | 0.009 (0.005) | ++ | 2.3 (0.1) | ++ | 0.39 (0.1) | ++ |

Normalized to β-actin (ACTB) expression [(target $2^{-CT}$/ACTB $2^{-CT}$) * 1000]. Data are the mean of 3 samples and error values are the standard error of the mean (sem).

†Relative staining intensity as compared to no 1° Ab control: +++ = high, ++ = moderate, + = low. Controls had no staining.

TABLE 8

| Target | Designation |
|---|---|
| PCDHB10 | SEQ ID NO 01 |
| PCDHB10 protein | SEQ ID NO 02 |
| IL1RAP | SEQ ID NO 03 |
| IL1RAP protein | SEQ ID NO 04 |
| SLC01B3 | SEQ ID NO 05 |
| SLC01B3 protein | SEQ ID NO 06 |
| PTPRR isoform 1 | SEQ ID NO 07 |
| PTPRR isoform 1 protein | SEQ ID NO 08 |
| PTPRR isoform 2 | SEQ ID NO 09 |
| PTPRR isoform 2 protein | SEQ ID NO 10 |
| SLC2A13 | SEQ ID NO 11 |
| SLC2A13 protein | SEQ ID NO 12 |
| FCGR1A | SEQ ID NO 13 |
| FCGR1A protein | SEQ ID NO 14 |
| CLEC4A isoform 1 | SEQ ID NO 15 |
| CLEC4A isoform 1 protein | SEQ ID NO 16 |
| CLEC4A isoform 2 | SEQ ID NO 17 |
| CLEC4A isoform 2 protein | SEQ ID NO 18 |
| CLEC4A isoform 3 | SEQ ID NO 19 |
| CLEC4A isoform 3 protein | SEQ ID NO 20 |
| CLEC4A isoform 4 | SEQ ID NO 21 |
| CLEC4A isoform 4 protein | SEQ ID NO 22 |
| TM4SF4 | SEQ ID NO 23 |
| TM4SF4 protein | SEQ ID NO 24 |
| ASGR1 | SEQ ID NO 25 |
| ASGR1 protein | SEQ ID NO 26 |
| PTPRC isoform 1 | SEQ ID NO 27 |
| PTPRC isoform 1 protein | SEQ ID NO 28 |
| PTPRC isoform 2 | SEQ ID NO 29 |
| PTPRC isoform 2 protein | SEQ ID NO 30 |
| PTPRC isoform 3 | SEQ ID NO 31 |
| PTPRC isoform 3 protein | SEQ ID NO 32 |
| PTPRC isoform 4 | SEQ ID NO 33 |
| PTPRC isoform 4 protein | SEQ ID NO 34 |
| MS4A4A | SEQ ID NO 35 |
| MS4A4A protein | SEQ ID NO 36 |
| TNFSF4 | SEQ ID NO 37 |
| TNFSF4 protein | SEQ ID NO 38 |
| MGC34293 | SEQ ID NO 39 |
| MGC34293 protein | SEQ ID NO 40 |
| TGFBR1 | SEQ ID NO 41 |
| TGFBR1 protein | SEQ ID NO 42 |
| HLADQA1 | SEQ ID NO 43 |
| HLADQA1 protein | SEQ ID NO 44 |
| CEACAM6 | SEQ ID NO 45 |
| CEACAM6 protein | SEQ ID NO 46 |
| PCDHB8 | SEQ ID NO 47 |
| PCDHB8 protein | SEQ ID NO 48 |
| PCDHB9 | SEQ ID NO 49 |
| PCDHB9 protein | SEQ ID NO 50 |

We claim:

1. A method of detecting a pancreatic tumor group comprising:
   obtaining a sample comprising a cell from a human subject;
   extracting nucleic acid from the sample;
   assessing the expression of a first RNA molecule comprising SEQ ID NO 01;
   assessing the expression of a second RNA molecule comprising SEQ ID NO 03;
   assessing the expression of a third RNA molecule comprising a sequence selected from a set consisting of SEQ ID NO 05, and SEQ ID NO 11; and
   comparing the expression of the first RNA molecule, the second RNA molecule, and the third RNA molecule to a normal pancreatic cell.

2. The method of claim 1 wherein assessing the expression comprises microarray analysis.

3. The method of claim 1 wherein assessing the expression comprises reverse transcriptase polymerase chain reaction.

4. The method of claim 1 wherein assessing the expression comprises quantitative real-time reverse transcriptase polymerase chain reaction.

5. The method of claim 1 wherein the nucleic acid comprises mRNA.

* * * * *